United States Patent
Keetman et al.

(10) Patent No.: US 7,345,216 B2
(45) Date of Patent: Mar. 18, 2008

(54) EXPRESSION CASSETTES FOR MERISTEM-PREFERENTIAL EXPRESSION IN PLANTS

(75) Inventors: Ulrich Keetman, Quedlinburg (DE); Ute Linemann, Gatersleben (DE); Karin Herbers, Neustadt (DE); Helke Hillebrand, Mannheim (DE)

(73) Assignee: SunGene GmbH & Co. KGaA (DE)

( * ) Notice: Subject to any disclaimer, the term of this patent is extended or adjusted under 35 U.S.C. 154(b) by 0 days.

(21) Appl. No.: 11/297,315

(22) Filed: Dec. 8, 2005

(65) Prior Publication Data

US 2006/0130178 A1 Jun. 15, 2006

(30) Foreign Application Priority Data

Dec. 11, 2004 (EP) .................................. 04029407
Feb. 3, 2005 (EP) .................................. 05002265
Feb. 11, 2005 (EP) .................................. 05002847

(51) Int. Cl.
*C12N 15/82* (2006.01)
*A01H 5/10* (2006.01)
*C07H 21/04* (2006.01)

(52) U.S. Cl. .................. 800/287; 536/24.1; 435/320.1; 435/419; 435/468; 800/298

(58) Field of Classification Search ..................... None
See application file for complete search history.

(56) References Cited

U.S. PATENT DOCUMENTS

| 5,589,583 A | 12/1996 | Klee et al. |
| 5,880,330 A | 3/1999 | Weigel et al. |
| 2003/0140378 A1 | 7/2003 | Bradley et al |

FOREIGN PATENT DOCUMENTS

WO WO-2005/108587 A1 11/2005

OTHER PUBLICATIONS

Ito et al. 1994, Plant Mol. Biol. 24:863-878.*
Jordan et al. 2000, Genbank accession: AL138657.*
NM_114425, 2002, Genbank accession.*
Padgette et al 1995, Crop Sci. 35:1451-1461.*
An et al 1986, Plant Physiol. 81:301-305.*
Fourgoux-Nicol et al. 1999, Plant Molecular Biology 40 :857-872.*
Kim et al. 1994, Plant Molecular Biology 24: 105-117.*
Oommenn et al 1994, The Plant Cell 6:1789-1803.*
"*Arabidopsis thaliana* TOM3 AT2G02180 (TOM3) mRNA, complete cds", Nov. 4, 2005, GenBank Accession No. NM_126278.
"TOM3 (*Arabidopsis thaliana*)", Nov. 4, 2005, GenBank Accession No. NP_027422.
"*Arabidopsis thaliana* DFL1 (Dwarf in Light 1) AT5G54510 (DFL1) mRNA, complete cds", Nov. 4, 2005, GenBank Accession No. NM_124831.
DFL1 (Dwarf in Light 1) [*Arabidopsis thaliana*], Nov. 4, 2005, GenBank Accession No. NP_200262.
"*Arabidopsis thaliana* exonuclease AT2G26970 transcript variant AT2G26970.1 mRNA, complete cds", Nov. 4, 2005, GenBank Accession No. NM_179759.
"Exonuclease [*Arabidopsis thaliana*]", Nov. 4, 2005, GenBank Accession No. NP_850090.
"*Arabidopsis thaliana* ATPAP1 (Phosphatidic Acid Phosphatase 1); phosphatidate phosphatase AT2G01180 (ATPAP1) transcript variant AT2G01180.2 mRNA, complete cds", Nov. 4, 2005, GenBank Accession No. NM_201660.
"ATPAP1 (Phosphatidic Acid Phosphatase 1); phosphatidate phosphatase [*Arabidopsis thaliana*]", Nov. 4, 2005, GenBank Accession No. NP_973389.
"*Arabidopsis thaliana* ubiquitin-protein ligase/ zinc ion binding AT3G45560 mRNA, complete cds", Nov. 4, 2005, GenBank Accession No. NM_114425.
"Ubiquitin-protein ligase/ zinc ion binding [*Arabidopsis thaliana*]", Nov. 4, 2005, GenBank Accession No. NP_190142.
"*Arabidopsis thaliana* unknown protein AT4G00580 mRNA, complete cds", Nov. 4, 2005, GenBank Accession No. NM_116282.
"Unknown protein [*Arabidopsis thaliana*]", Nov. 4, 2005, GenBank Accession No. NP_191967.
"*Arabidopsis thaliana* protein binding AT1G54480 mRNA, complete cds", Nov. 4, 2005, GenBank Accession No. NM_104326.
"Protein binding [*Arabidopsis thaliana*]", Nov. 4, 2005, GenBank Accession No. NP_175850.
"*Arabidopsis thaliana* kinase AT4G11490 mRNA, complete cds", Nov. 4, 2005, GenBank Accession No. NM_117220.
"Kinase [*Arabidopsis thaliana*]", Nov. 5, 2005, GenBank Accession No. NP_192888.

* cited by examiner

*Primary Examiner*—Ashwin Mehta
*Assistant Examiner*—Li Zheng
(74) *Attorney, Agent, or Firm*—Connolly Bove Lodge & Hutz LLP

(57) ABSTRACT

The present invention relates to expression cassettes comprising transcription regulating sequences with meristem-preferential or meristem-specific expression profiles in plants obtainable from *Arabidopsis thaliana* genes At2g02180, At5g54510, At2g26970, At2g01180, At3g45560, At4g00580, At1g54480, or At4g11490, or the *Arabidopsis thaliana* genomic sequences as described by SEQ ID NO: 35 or 36.

18 Claims, No Drawings

EXPRESSION CASSETTES FOR MERISTEM-PREFERENTIAL EXPRESSION IN PLANTS

RELATED APPLICATIONS

This application claims benefit to European Application 04029407.6 filed Dec. 11, 2004, to European Application 05002265.6 filed Feb. 3, 2005, and to European Application 05002847.1 filed Feb. 11, 2005.

FIELD OF THE INVENTION

The present invention relates to expression cassettes comprising transcription regulating nucleotide sequences with meristem-preferential or meristem-specific expression profiles in plants obtainable from *Arabidopsis thaliana* genes At2g02180, At5g54510, At2g26970, At2g01180, At3g45560, At4g00580, At1g54480, or At4g11490, or the *Arabidopsis thaliana* genomic sequences as described by SEQ ID NO: 35 or 36.

SUBMISSION ON COMPACT DISC

The contents of the following submission on compact discs are incorporated herein by reference in its entirety: A compact disc copy of the Sequence Listing (COPY 1) (file name: Final sequence list-13173-00021-US, date recorded: Dec. 7, 2005, size: 149 KB); a duplicate compact disc copy of the Sequence Listing (COPY 2) (file name: Final sequence list-13173-00021-US, date recorded: Dec. 7, 2005, size: 149 KB); a computer readable form copy of the Sequence Listing (CRF COPY) (file name: Final sequence list-13173-00021-US, date recorded: Dec. 7, 2005, size: 149 KB).

BACKGROUND OF THE INVENTION

Manipulation of plants to alter and/or improve phenotypic characteristics (such as productivity or quality) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant.

The plant meristem is the source from which new tissues and organs of a plant are produced. The meristem-preferential or meristem-specific promoters are useful for regulating plant development and other relevant agronomic traits. However, the number of promoters with meristem-preferential or meristem-specific expression profiles is very limited.

There is, therefore, a great need in the art for the identification of novel sequences that can be used for expression of selected transgenes in economically important plants. It is thus an objective of the present invention to provide new and alternative expression cassettes for meristem-preferential or meristem-specific expression of transgenes in plants. The objective is solved by the present invention.

SUMMARY OF THE INVENTION

Accordingly, a first embodiment of the invention relates to an expression cassette for meristem-specific or meristem-preferential transcription of an operatively linked nucleic acid sequence in plants comprising i) at least one transcription regulating nucleotide sequence of a plant gene, said plant gene selected from the group of genes described by the GenBank *Arabidopsis thaliana* genome loci At2g02180, At5g54510, At2g26970, At2g01180, At3g45560, At4g00580, At1g54480, or At4g11490, or the *Arabidopsis thaliana* genomic sequences as described by SEQ ID NO: 35 or 36, or a functional equivalent thereof, and functionally linked thereto ii) at least one nucleic acid sequence which is heterologous in relation to said transcription regulating nucleotide sequence.

Preferably, the transcription regulating nucleotide sequence (or the functional equivalent thereof) is selected from the group of sequences consisting of i) the sequences described by SEQ ID NOs: 1, 2, 3, 6, 7, 8, 11, 12, 15, 16, 17, 20, 21, 24, 25, 28, 31, 32, 35, and 36, ii) a fragment of at least 50 consecutive bases of a sequence under i) which has substantially the same promoter activity as the corresponding transcription regulating nucleotide sequence described by SEQ ID NO: 1, 2, 3, 6, 7, 8, 11, 12, 15, 16, 17, 20, 21, 24, 25, 28, 31, 32, 35, or 36;

iii) a nucleotide sequence having substantial similarity (e.g., with a sequence identity of at least 40, 50, 60, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91%, 92%, 93%, 94%, 95%, 96%, 97%, to 98% and 99%) to a transcription regulating nucleotide sequence described by SEQ ID NO: 1, 2, 3, 6, 7, 8, 11, 12, 15, 16, 17, 20, 21, 24, 25, 28, 31, 32, 35, or 36;

iv) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a transcription regulating nucleotide sequence described by SEQ ID NO: 1, 2, 3, 6, 7, 8, 11, 12, 15, 16, 17, 20, 21, 24, 25, 28, 31, 32, 35, or 36, or the complement thereof;

v) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C. (more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 6, 7, 8, 11, 12, 15, 16, 17, 20, 21, 24, 25, 28, 31, 32, 35, and 36, or the complement thereof;

vi) a nucleotide sequence which is the complement or reverse complement of any of the previously mentioned nucleotide sequences under i) to v).

The functional equivalent of the transcription regulating nucleotide sequence is obtained or obtainable from plant genomic DNA from a gene encoding a polypeptide which has at least 70% amino acid sequence identity to a polypeptide selected from the group described by SEQ ID NO: 5, 10, 14, 19, 23, 27, 30, and 34, respectively. The expression cassette may be employed for numerous expression purposes such as for example expression of a protein, or expression of a antisense RNA, sense or double-stranded RNA. Preferably, expression of the nucleic acid sequence confers to the plant an agronomically valuable trait.

Other embodiments of the invention relate to vectors comprising an expression cassette of the invention, and transgenic host cell or non-human organism comprising an expression cassette or a vector of the invention. Preferably the organism is a plant.

Another embodiment of the invention relates to a method for identifying and/or isolating a sequence with meristem-specific or meristem-preferential transcription regulating activity characterized that said identification and/or isolation utilizes a nucleic acid sequence encoding a amino acid sequence as described by SEQ ID NO: 5, 10, 14, 19, 23, 27, 30, or 34 or a part of at least 15 bases thereof. Preferably the nucleic acid sequences is described by SEQ ID NO: 4, 9, 13, 18, 22, 26, 29, or 33 or a part of at least 15 bases thereof. More preferably, identification and/or isolation is realized by a method selected from polymerase chain reaction, hybridization, and database screening.

Another embodiment of the invention relates to a method for providing a transgenic expression cassette for meristem-specific or meristem-preferential expression comprising the steps of:

I. isolating of a meristem-preferential or meristem-specific transcription regulating nucleotide sequence utilizing at least one nucleic acid sequence or a part thereof, wherein said sequence is encoding a polypeptide described by SEQ ID NO: 5, 10, 14, 19, 23, 27, 30, or 34, or a part of at least 15 bases thereof, and II. functionally linking said meristem-preferential or meristem-specific transcription regulating nucleotide sequence to another nucleotide sequence of interest, which is heterologous in relation to said meristem-preferential or meristem-specific transcription regulating nucleotide sequence.

Definitions

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 per-cent up or down (higher or lower).

As used herein, the word "or" means any one member of a particular list and also includes any combination of members of that list.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i.e., a cell not having a known mutation.

A "marker gene" encodes a selectable or screenable trait.

The term "chimeric gene" refers to any gene that contains
1) DNA sequences, including regulatory and coding sequences, that are not found together in nature, or
2) sequences encoding parts of proteins not naturally adjoined, or
3) parts of promoters that are not naturally adjoined.

Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

The terms "protein," "peptide" and "polypeptide" are used interchangeably herein. The nucleotide sequences of the invention can be introduced into any plant. The genes to be introduced can be conveniently used in expression cassettes for introduction and expression in any plant of interest. Such expression cassettes will comprise the transcriptional initiation region of the invention linked to a nucleotide sequence of interest. Preferred promoters include constitutive, tissue-specific, developmental-specific, inducible and/or viral promoters, most preferred are the meristem-specific or meristem-preferential promoters of the invention. Such an expression cassette is provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens,* such, as the octopine synthase and nopaline synthase termination regions (see also, Guerineau 1991; Proudfoot 1991; Sanfacon 1991; Mogen 1990; Munroe 1990; Ballas 1989; Joshi 1987).

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Transcription regulating nucleotide sequence", transcription regulating nucleotide sequence "regulatory sequences", and "suitable regulatory sequences", each refer to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' non-coding sequences) of the sequence to be transcribed (e.g., a coding sequence). The transcription regulating nucleotide sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences. As is noted above, the term "transcription regulating nucleotide sequence" is not limited to promoters. However, preferably a transcription regulating nucleotide sequence of the invention comprises at least one promoter sequence (e.g., a sequence localized upstream of the transcription start of a gene capable to induce transcription of the downstream sequences). In one preferred embodiment the transcription regulating nucleotide sequence of the invention comprises the promoter sequence of the corresponding gene and—optionally and preferably—the native 5'-untranslated region of said gene. Furthermore, the 3'-untranslated region and/or the polyadenylation region of said gene may also be employed.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner 1995).

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide. The term "transit peptide" as used herein refers part of a expressed polypeptide (preferably the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably-linked" or "functionally linked" refers preferably to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates.

The rate of degradation can however be considered to proceed at a fixed rate when the transcribed sequences are identical, and thus this value can serve as a measure of synthesis rates. When promoters are compared in this way techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription.

A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression.

Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Overexpression" refers to the level of expression in transgenic cells or organisms that exceeds levels of expression in normal or untransformed (non-transgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species. homologous to the affected genes (English 1996). Gene silencing includes virus-induced gene silencing (Ruiz et al. 1998).

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents of *Arabidopsis* sequences disclosed herein.

In its broadest sense, the term "substantially similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. For example, altered nucleotide sequences which simply reflect the degeneracy of the genetic code but nonetheless encode amino acid sequences that are identical to a particular amino acid sequence are substantially similar to the particular sequences. The term "substantially similar" also includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide.

In its broadest sense, the term "substantially similar" when used herein with respect to polypeptide means that the polypeptide has substantially the same structure and function as the reference polypeptide. In addition, amino acid sequences that are substantially similar to a particular sequence are those wherein overall amino acid identity is at least 65% or greater to the instant sequences. Modifications that result in equivalent nucleotide or amino acid sequences are well within the routine skill in the art. The percentage of amino acid sequence identity between the substantially similar and the reference polypeptide is at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99%, wherein the reference polypeptide is an *Arabidopsis* polypeptide encoded by a gene with a promoter having any one of SEQ ID NOs: 1, 2, 3, 6, 7, 8, 11, 12, 15, 16, 17, 20, 21, 24, 25, 28, 31, 32, 35, or 36, a nucleotide sequence comprising an open reading frame having any one of SEQ ID NOs: 4, 9, 13, 18, 22, 26, 29, or 33, which encodes one of SEQ ID NOs: 5, 10, 14, 19, 23, 27, 30, or 34. One indication that two polypeptides are substantially similar to each other, besides having substantially the same function, is that an agent, e.g., an antibody, which specifically binds to one of the polypeptides, also specifically binds to the other.

Sequence comparisons maybe be carried out using a Smith-Waterman sequence alignment algorithm (see e.g., Waterman (1995)). The locals program, version 1.16, is preferably used with following parameters: match: 1, mismatch penalty: 0.33, open-gap penalty: 2, extended-gap penalty: 2.

Moreover, a nucleotide sequence that is "substantially similar" to a reference nucleotide sequence is said to be "equivalent" to the reference nucleotide sequence. The skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

What is meant by "substantially the same activity" when used in reference to a polynucleotide or polypeptide fragment is that the fragment has at least 65%, 66%, 67%, 68%, 69%, 70%, e.g., 71%, 72%, 73%, 74%, 75%, 76%, 77%, 78%, 79%, 80%, 81%, 82%, 83%, 84%, 85%, 86%, 87%, 88%, 89%, and even 90% or more, e.g., 91%, 92%, 93%, 94%, 95%, 96%, 97%, 98%, up to at least 99% of the activity of the full length polynucleotide or full length polypeptide.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a transgenic plant relative to the wild-type or non-transgenic plant host.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include *Agrobacterium*-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as *Agrobacterium*-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as *Agrobacterium*-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "TO generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

"Genome" refers to the complete genetic material of an organism.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly-encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

The nucleic acid molecules of the invention can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass, sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art (see, for example, Stemmer 1994; Stemmer 1994; Crameri 1997; Moore 1997; Zhang 1997; Crameri 1998; and U.S. Pat. Nos. 5,605,793 and 5,837,458).

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art (see, for example, Kunkel 1985; Kunkel 1987; U.S. Pat. No. 4,873,192; Walker & Gaastra, 1983 and the references cited therein). Guidance as to appropriate amino acid substitutions that do not affect biological activity of the protein of interest may be found in the model of Dayhoff et al. (1978). Conservative substitutions, such as exchanging one amino acid with another having similar properties, are preferred.

Individual substitutions deletions or additions that alter, add or delete a single amino acid or a small percentage of amino acids (typically less than 5%, more typically less than 1%) in an encoded. sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development (e.g., the meristem-specific or meristem-preferential promoters of the invention).

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul, supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (B) of 10, and the BLOSUM62 scoring matrix (see Henikoff & Henikoff 1989). Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" or "substantial similarity" of polynucleotide sequences (preferably for a protein encoding sequence) means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. The term "substantial identity" or "substantial similarity" of polynucleotide sequences (preferably for promoter sequence) means (as described above for variants) that a polynucleotide comprises a sequence that has at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 70%, 71%, 72%, 73%, 74%, 75%, 76%, 77%, 78%, or 79%, preferably 80%, 81%, 82%, 83%, 84%, 85%, 86%, 87%, 88%, or 89%; more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970) An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m = 81.5° \text{C.} + 16.6(\log_{10}M) + 0.41(\% \text{ GC}) - 0.61(\% \text{ form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule" is a combination of DNA sequences that are joined together using recombinant DNA technology and procedures used to join together DNA sequences as described, for example, in Sambrook et al., 1989.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same.

The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae.

Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (*hepaticas*) and Musci (mosses); pteridophytes such as ferns, horsetail and clubmosses; gymnosperms such as conifers, cycads, ginkgo and Gnetaeae;

algae such as Chlorophyceae, Phaeophpyceae, Rhodophyceae, Myxophyceae, Xanthophyceae, Bacillariophyceae (diatoms) and Euglenophyceae.

Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as Drachaena, Moraceae such as ficus, Araceae such as philodendron and many others.

The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species *carota* (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others.

The transgenic plants according to the invention may be selected among monocotyledonous crop plants, such as, for example, cereals such as wheat, barley, sorghum and millet, rye, triticale, maize, rice or oats, and sugarcane. Further preferred are trees such as apple, pear, quince, plum, cherry, peach, nectarine, apricot, papaya, mango, and other woody species including coniferous and deciduous trees such as poplar, pine, sequoia, cedar, oak, etc. Especially preferred are *Arabidopsis thaliana, Nicotiana tabacum*, oilseed rape, soybean, corn (maize), wheat, linseed, potato and tagetes.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

DETAILED DESCRIPTION OF THE INVENTION

The present invention thus provides for isolated nucleic acid molecules comprising a plant nucleotide sequence that directs meristem-preferential or meristem-specific transcription of an operably linked nucleic acid fragment in a plant cell.

Specifically, the present invention provides transgenic expression cassettes for regulating meristem-preferential or meristem-specific expression in plants comprising i) at least one transcription regulating nucleotide sequence of a plant gene, said plant gene selected from the group of genes described by the GenBank *Arabidopsis thaliana* genome locii At2g02180, At5g54510, At2g26970, At2g01180, At3g45560, At4g00580, At1g54480, or At4g11490, or the *Arabidopsis thaliana* genomic sequences as described by SEQ ID NO: 35 or 36, or a functional equivalent thereof, and functionally linked thereto ii) at least one nucleic acid sequence which is heterologous in relation to said transcription regulating nucleotide sequence.

The term "meristem" in the context of the invention means the usually group of undifferentiated cells from which new tissues and organs are produced. Meristems are characterized by active cell division. Meristems are plant tissues composed of dividing cells and giving rise to organs such as leaves, flowers, xylem, phloem, roots. Meristems are regions of a plant in which cells are not fully differentiated and which are capable of repeated mitotic divisions. Most plants have apical meristems which give rise to the primary tissues of plants. The main meristematic areas within the plant are the apical meristems of the terminal and lateral shoots, the vascular cambium, the root apex, and the marginal meristems (active during the growth of leaves). Lateral meristems exist near root and shoot tips causing vertical plant growth. Higher plants produce most organs post-embryonically, including stems, leaves and roots. These organs develop from meristems at the tip of the stem and the root that are called the shoot apical meristem (SAM) and the root apical meristem, respectively. In dicots, the SAM serves as source of pluripotent stem cells and plays a central role in shoot organ formation.

Meristem specific promoters are useful for regulation of expression of several genes in meristematic cells, especially in meristems of leaf axils and abscission zones of flowers, fruits, siliques or pods. Beside the more general applications described below, the meristem specific or preferential promoters of the invention are useful for one or more of the following applications:

a) specific expression in shoot meristem of genes involved in regulating development. Such genes include those involved in flowering, as well genes that protect against pathogens by encoding toxins (see e.g., U.S. Pat. No. 5,880,330)

b) expression of insect resistance or tolerance, herbicide resistance or tolerance, disease resistance or tolerance (e.g. resistance to viruses or fungal pathogens), stress tolerance (increased salt tolerance) and improved food content or increased yield (see e.g., WO01/18211)

c) expression of genes for reducing formation of lateral shoots particularly e.g. in tomato, tobacco, wine, cereals and lumber. Lateral shoots are sink organs and reduce the yield of main shoots. Wild or great branching systems are difficult to harvest with machines. Fruits on main and lateral sprouts are ripening to different time points. This prevents a concurrent harvest. Undesired nods in lumber has to be removed (see e.g., WO02/06487).

d) expression of genes like cell wall invertases to accelerate flowering resulting in an increase in seed yield. (Heyer A G et al. (2004) Plant J. 39 (2):161-169.

e) expression of genes controlling the transition to flowering, or genes to reduce losses due to pests and stresses damaging plant apical meristems.

f) By inhibiting/over expression of proteins that modulate meristem development, and specifically increases meristem cell proliferation, enlargement of meristems in plants can be induced. This is useful for increasing meristem cell proliferation that causes increased row number in maize and is useful for manipulating meristem growth, organ development, seed number, inflorescence development and arrangement, development and embryogenesis, to increase yield, health and stability of plants. (see e.g., WO 2001070987).

e) expression of transgenes that regulate cytokinin response. These approaches are useful for a variety of agricultural and commercial purposes including improving and enhancing photosynthesis, promoting cell proliferation, shoot meristem formation, promoting leaf developing, increasing crop yields, improving crop and ornamental quality and reducing agricultural production costs (see e.g., WO 02/099079).

g) expression of genes encoding RALF polypeptides which are known to stimulate the growth of plant meristems (see. e.g., WO 01/60972). The yield of edible material from a crop plant and the yield of one or more desired chemical products produced by a plant, depends, in part, on the size of the plant. The size of the plant is determined, at least in part, by the rate of growth of the plant meristems.

h) expression of enzymes to manipulate genomic DNA and ensure that said manipulation is transmitted to the next cell and to the progeny. For example, nucleases or recombinases can be fused to said promoters. In consequence, nucleases or recombinases are expressed in meristems and act on their target sequences in the genome. Nucleases or recombinases can induce recombination at their respective target site(s) (e.g. for marker excision or site-specific integration. Various methods are known in the art for marker excision [e.g. WO03004659; WO93/01283] and site-specific integration [e.g. WO96/14408; WO 00/11155]).

i) Meristem specific promoters operably linked to target sequences are useful for conditional or regulated gene silencing in plants. Recombinase inversion or excision yields double-stranded RNA, which thereby functions to trigger endogenous gene silencing mechanism. By combination meristem specific promoters with recombinase systems, transcriptional stop fragments or introns and target sequences, gene silencing of virtually any target sequences may be modulated at any plant development stage or in any plant generation. This is especially useful, when genes responsible for gene silencing are down regulated to permit expression of particular transgenes at levels greater than permitted when gene silencing is activated (see. e.g., WO 2004/003180)

i) Meristem specific promoters are useful to confer virus induced gene silencing across meristematic tissue for altering the phenotype of a plant which involves silencing the target gene. e.g. an unwanted trait in a plant (see e.g., CA 2297616).

"Meristem-specific transcription" in the context of this invention means the transcription of a nucleic acid sequence by a transcription regulating element in a way that transcription of said nucleic acid sequence in the meristem contribute to more than 90%, preferably more than 95%, more preferably more than 99% of the entire quantity of the RNA transcribed from said nucleic acid sequence in the entire plant during any of its developmental stage. The transcription regulating nucleotide sequences designated pSUH415, pSUH415L, pSUH415GB, pSUH416, pSUH416GB, pSUH431, pSUH431GB, pSUH417, pSUH417GB, and pSUH432 and their respective shorter and longer variants are considered to be meristem-specific transcription regulating nucleotide sequences.

"Meristem-preferential transcription" in the context of this invention means the transcription of a nucleic acid sequence by a transcription regulating element in a way that transcription of said nucleic acid sequence in the meristem contribute to more than 50%, preferably more than 70%, more preferably more than 80% of the entire quantity of the RNA transcribed from said nucleic acid sequence in the entire plant during any of its developmental stage. The transcription regulating nucleotide sequences designated pSUH413, pSUH413GB, pSUH438, pSUH438v, pSUH438GB, pSUH433, pSUH433GB, pSUH436, pSUH436S, and pSUH436GB and their respective shorter and longer variants are considered to be meristem-preferential transcription regulating nucleotide sequences.

Preferably a transcription regulating nucleotide sequence of the invention comprises at least one promoter sequence of the respective gene (e.g., a sequence localized upstream of the transcription start of the respective gene capable to induce transcription of the downstream sequences). The transcription regulating nucleotide sequence may comprise the promoter sequence of said genes but may further comprise other elements such as the 5'-untranslated sequence, enhancer, introns etc. Preferably, said promoter sequence directs meristem-preferential or meristem-specific transcription of an operably linked nucleic acid segment in a plant or plant cell e.g., a linked plant DNA comprising an open reading frame for a structural or regulatory gene. The following Table 1 illustrates the genes from which the promoters of the invention are preferably isolated, the function of said genes, the cDNA encoded by said genes, and the protein (ORF) encoded by said genes.

TABLE 1

Genes from which the promoters of the invention are preferably isolated, putative function of said genes, cDNA and the protein encoded by said genes.

| Gene Locus | Putative function | Promoter SEQ ID | mRNA locus ID cDNA SEQ ID | Proteine ID Protein SEQ ID |
|---|---|---|---|---|
| At2g02180 | tobamovirus multiplication protein 3 (TOM3) | SEQ ID NO: 1, 2, 3 | NM_126278 SEQ ID NO: 4 | NP_027422 SEQ ID NO: 5 |
| At5g54510 | auxin-responsive GH3 protein | SEQ ID NO: 6, 7, 8 | NM_124831 SEQ ID NO: 9 | NP_200262 SEQ ID NO: 10 |
| At2g26970 | exonuclease family protein | SEQ ID NO: 11, 12 | NM_179759 SEQ ID NO: 13 | NP_850090 SEQ ID NO: 14 |
| At2g01180 | putative phosphatidic acid phosphatase | SEQ ID NO: 15, 16, 17 | NM_201660 SEQ ID NO: 18 | NP_973389 SEQ ID NO: 19 |

TABLE 1-continued

Genes from which the promoters of the invention are preferably isolated, putative function of said genes, cDNA and the protein encoded by said genes.

| Gene Locus | Putative function | Promoter SEQ ID | mRNA locus ID cDNA SEQ ID | Proteine ID Protein SEQ ID |
|---|---|---|---|---|
| At3g45560 | zinc finger (C3HC4-type RING finger) family | SEQ ID NO: 20, 21 | NM_114425 SEQ ID NO: 22 | NP_190142 SEQ ID NO: 23 |
| At4g00580 | COP1-interacting protein-related | SEQ ID NO: 24, 25 | NM_116282 SEQ ID NO: 26 | NP_191967 SEQ ID NO: 27 |
| At1g54480 | leucine-rich repeat family protein | SEQ ID NO: 28 | NM_104326 SEQ ID NO: 29 | NP_175850 SEQ ID NO: 30 |
| At4g11490 | serin/threonin kinase like protein | SEQ ID NO: 31, 32 | NM_117220 SEQ ID NO: 33 | NP_192888 SEQ ID NO: 34 |
| | no EST correlation sequence is positioned downstream and in opposite direction to ORF of gene At2g31160 | SEQ ID NO: 35, 36 | | |

Preferably the transcription regulating nucleotide sequence (or the functional equivalent thereof) is selected from the group of sequences consisting of
i) the sequences described by SEQ ID NOs: 1, 2, 3, 6, 7, 8, 11, 12, 15, 16, 17, 20, 21, 24, 25, 28, 31, 32, 35, and 36;
ii) a fragment of at least 50 consecutive bases of a sequence under i) which has substantially the same promoter activity as the corresponding transcription regulating nucleotide sequence described by 1, 2, 3, 6, 7, 8, 11, 12, 15, 16, 17, 20, 21, 24, 25, 28, 31, 32, 35, or 36;
iii) a nucleotide sequence having substantial similarity (e.g., with a sequence identity of at least 40, 50, 60, to 70%, e.g., preferably 71%, 72%, 73%, 74%, 75%, 76%, 77%, 78%, to 79%, generally at least 80%, e.g., 81% to 84%, at least 85%, e.g., 86%, 87%, 88%, 89%, 90%, 91.%, 92%, 93%, 94%, 95%, 96%, 97%, to 98% and 99%) to a transcription regulating nucleotide sequence described by SEQ ID NO: 1, 2, 3, 6, 7, 8, 11, 12, 15, 16, 17, 20, 21, 24, 25, 28, 31, 32, 35, or 36;
iv) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C. (more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a transcription regulating nucleotide sequence described by SEQ ID NO: 1, 2, 3, 6, 7, 8, 11, 12, 15, 16, 17, 20, 21, 24, 25, 28, 31, 32, 35, or 36, or the complement thereof;
v) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C. (more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 6, 7, 8, 11, 12, 15, 16, 17, 20, 21, 24, 25, 28, 31, 32, 35, or 36, or the complement thereof;
vi) a nucleotide sequence which is the complement or reverse complement of any of the previously mentioned nucleotide sequences under i) to v).

A functional equivalent of the transcription regulating nucleotide sequence can also be obtained or is obtainable from plant genomic DNA from a gene encoding a polypeptide which is substantially similar and preferably has at least 70%, preferably 80%, more preferably 90%, most preferably 95% amino acid sequence identity to a polypeptide encoded by an *Arabidopsis thaliana* gene comprising any one of SEQ ID NOs: 5, 10, 14, 19, 23, 27, 30, or 34, respectively, or a fragment of said transcription regulating nucleotide sequence which exhibits promoter activity in a meristem-preferential or meristem-specific fashion.

The activity of a certain transcription regulating nucleotide sequence is considered equivalent if transcription is initiated preferentially or specifically in the same tissue (i.e. meristematic tissue) than the original promoter. Such expression profile is preferably demonstrated using reporter genes operably linked to said transcription regulating nucleotide sequence. Preferred reporter genes (Schenborn 1999) in this context are green fluorescence protein (GFP) (Chui 1996; Leffel 1997), chloramphenicol transferase, luciferase (Millar 1992), β-glucuronidase or β-galactosidase. Especially preferred is β-glucuronidase (Jefferson 1987).

Beside this the transcription regulating activity of a function equivalent may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences which—in comparison with its parent sequence—does not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase my at least 50%, more preferably by at least 100%, most preferably by at least 500%.

Preferably functional equivalent of the transcription regulating nucleotide sequence can be obtained or is obtainable from plant genomic DNA from a gene expressing a mRNA described by a cDNA which is substantially similar and preferably has at least 70%, preferably 80%, more preferably 90%, most preferably 95% sequence identity to a sequence described by any one of SEQ ID NOs: 4, 9, 13, 18, 22, 26, 29, or 33, respectively, or a fragment of said transcription regulating nucleotide sequence which exhibits promoter activity in a meristem-preferential or meristem-specific fashion.

Such functional equivalent of the transcription regulating nucleotide sequence may be obtained from other plant species by using the meristem-preferential or meristem-specific *Arabidopsis* promoter sequences described herein as probes to screen for homologous structural genes in other plants by hybridization under low, moderate or stringent hybridization conditions. Regions of the meristem-preferential or meristem-specific promoter sequences of the present invention which are conserved among species could also be used as PCR primers to amplify a segment from a species other than *Arabidopsis,* and that segment used as a hybridization probe (the latter approach permitting higher stringency screening) or in a transcription assay to determine promoter activity. Moreover, the meristem-preferential or meristem-specific promoter sequences could be employed to identify structurally related sequences in a database using computer algorithms.

More specifically, based on the *Arabidopsis* nucleic acid sequences of the present invention, orthologs may be identified or isolated from the genome of any desired organism, preferably from another plant, according to well known techniques based on their sequence similarity to the *Arabidopsis* nucleic acid sequences, e.g., hybridization, PCR or computer generated sequence comparisons. For example, all or a portion of a particular *Arabidopsis* nucleic acid sequence is used as a probe that selectively hybridizes to other gene sequences present in a population of cloned genomic DNA fragments or cDNA fragments (i.e., genomic or cDNA libraries) from a chosen source organism. Further, suitable genomic and cDNA libraries may be prepared from any cell or tissue of an organism. Such techniques include hybridization screening of plated DNA libraries (either plaques or colonies; see, e.g., Sambrook 1989) and amplification by PCR using oligonucleotide primers preferably corresponding to sequence domains conserved among related polypeptide or subsequences of the nucleotide sequences provided herein (see, e.g., Innis 1990). These methods are particularly well suited to the isolation of gene sequences from organisms closely related to the organism from which the probe sequence is derived. The application of these methods using the *Arabidopsis* sequences as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least 40% to 50%, about 60% to 70% and even about 80% 85%, 90%, 95% to 98% or more identity with the disclosed sequences. That is, the sequence similarity of sequences may range, sharing at least about 40% to 50%, about 60% to 70%, and even about 80%, 85%, 90%, 95% to 98% sequence similarity.

The nucleic acid molecules of the invention can also be identified by, for example, a search of known databases for genes encoding polypeptides having a specified amino acid sequence identity or DNA having a specified nucleotide sequence identity. Methods of alignment of sequences for comparison are well known in the art and are described hereinabove.

Hence, the isolated nucleic acid molecules of the invention include the orthologs of the *Arabidopsis* sequences disclosed herein, i.e., the corresponding nucleotide sequences in organisms other than *Arabidopsis*, including, but not limited to, plants other than *Arabidopsis,* preferably dicotyledonous plants, e.g., *Brassica napus,* alfalfa, sunflower, soybean, cotton, peanut, tobacco or sugar beet, but also cereal plants such as corn, wheat, rye, turfgrass, sorghum, millet, sugarcane, barley and banana. An orthologous gene is a gene from a different species that encodes a product having the same or similar function, e.g., catalyzing the same reaction as a product encoded by a gene from a reference organism. Thus, an ortholog includes polypeptides having less than, e.g., 65% amino acid sequence identity, but which ortholog encodes a polypeptide having the same or similar function. Databases such GenBank may be employed to identify sequences related to the *Arabidopsis* sequences, e.g., orthologs in other dicotyledonous plants such as *Brassica napus* and others. Alternatively, recombinant DNA techniques such as hybridization or PCR may be employed to identify sequences related to the *Arabidopsis* sequences or to clone the equivalent sequences from different *Arabidopsis* DNAs.

The transcription regulating nucleotide sequences of the invention or their functional equivalents can be obtained or isolated from any plant or non-plant source, or produced synthetically by purely chemical means. Preferred sources include, but are not limited to the plants defined in the DEFINITION section above.

Thus, another embodiment of the invention relates to a method for identifying and/or isolating a sequence with meristem-preferential or meristem-specific transcription regulating activity utilizing a nucleic acid sequence encoding a amino acid sequence as described by SEQ ID NO: 5, 10, 14, 19, 23, 27, 30, or 34 or a part thereof. Preferred are nucleic acid sequences described by SEQ ID NO: 4, 9, 13, 18, 22, 26, 29, or 33 or parts thereof. "Part" in this context means a nucleic acid sequence of at least 15 bases preferably at least 25 bases, more preferably at least 50 bases. The method can be based on (but is not limited to) the methods described above such as polymerase chain reaction, hybridization or database screening. Preferably, this method of the invention is based on a polymerase chain reaction, wherein said nucleic acid sequence or its part is utilized as oligonucleotide primer. The person skilled in the art is aware of several methods to amplify and isolate the promoter of a gene starting from part of its coding sequence (such as, for example, part of a cDNA). Such methods may include but are not limited to method such as inverse PCR ("iPCR") or "thermal asymmetric interlaced PCR" ("TAIL PCR").

Another embodiment of the invention is related to a method for providing a transgenic expression cassette for meristem-preferential or meristem-specific expression comprising the steps of:

I. isolating of a meristem-preferential or meristem-specific transcription regulating nucleotide sequence utilizing at least one nucleic acid sequence or a part thereof, wherein said sequence is encoding a polypeptide described by SEQ ID NO: 5, 10, 14, 19, 23, 27, 30, or 34, or a part of at least 15 bases thereof, and II. functionally linking said meristem-preferential or meristem-specific transcription regulating nucleotide sequence to another nucleotide sequence of interest, which is heterologous in relation to said meristem-preferential or meristem-specific transcription regulating nucleotide sequence.

Preferably, the nucleic acid sequence employed for the isolation comprises at least 15 base, preferably at least 25 bases, more preferably at least 50 bases of a sequence described by SEQ ID NO: 4, 9, 13, 18, 22, 26, 29, or 33. Preferably, the isolation of the meristem-preferential or meristem-specific transcription regulating nucleotide sequence is realized by a polymerase chain reaction utilizing said nucleic acid sequence as a primer. The operable linkage can be realized by standard cloning method known in the art such as ligation-mediated cloning or recombination-mediated cloning.

Preferably, the transcription regulating nucleotide sequences and promoters of the invention include a consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 6, 7, 8, 11, 12, 15, 16, 17, 20, 21, 24, 25, 28, 31, 32, 35, and 36, or the promoter orthologs thereof, which include the minimal promoter region.

In a particular embodiment of the invention said consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, has at least 75%, preferably 80%, more preferably 90% and most preferably 95%, nucleic acid sequence identity with a corresponding consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 6, 7, 8, 11, 12, 15, 16, 17, 20, 21, 24, 25, 28, 31, 32, 35, and 36, or the promoter orthologs thereof, which include the minimal promoter region. The above defined stretch of contiguous nucleotides preferably comprises one or more promoter motifs selected from the group consisting of TATA box, GC-box, CAAT-box and a transcription start site.

The transcription regulating nucleotide sequences of the invention or their functional equivalents are capable of driving meristem-preferential or meristem-specific expression of a coding sequence in a target cell, particularly in a plant cell. The promoter sequences and methods disclosed herein are useful in regulating meristem-preferential or meristem-specific expression, respectively, of any heterologous nucleotide sequence in a host plant in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences.

The transcription regulating nucleotide sequences and promoters of the invention are useful to modify the phenotype of a plant. Various changes in the phenotype of a transgenic plant are desirable, i.e., modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in an alteration in the phenotype of the transformed plant.

Generally, the transcription regulating nucleotide sequences and promoters of the invention may be employed to express a nucleic acid segment that is operably linked to said promoter such as, for example, an open reading frame, or a portion thereof, an anti-sense sequence, a sequence encoding for a double-stranded RNA sequence, or a transgene in plants.

An operable linkage may—for example—comprise an sequential arrangement of the transcription regulating nucleotide sequence of the invention (for example a sequence as described by SEQ ID NO: 1, 2, 3, 6, 7, 8, 11, 12, 15, 16, 17, 20, 21, 24, 25, 28, 31, 32, 35, or 36 ) with a nucleic acid sequence to be expressed, and—optionally—additional regulatory elements such as for example polyadenylation or transcription termination elements, enhancers, introns etc, in a way that the transcription regulating nucleotide sequence can fulfill its function in the process of expression the nucleic acid sequence of interest under the appropriate conditions. the term "appropriate conditions" mean preferably the presence of the expression cassette in a plant cell. Preferred are arrangements, in which the nucleic acid sequence of interest to be expressed is placed down-stream (i.e., in 3'-direction) of the transcription regulating nucleotide sequence of the invention in a way, that both sequences are covalently linked. Optionally additional sequences may be inserted in-between the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the nucleic acid sequence of interest to be expressed and the transcription regulating nucleotide sequence of the invention is not more than 200 base pairs, preferably not more than 100 base pairs, more preferably no more than 50 base pairs.

An operable linkage in relation to any expression cassette or of the invention may be realized by various methods known in the art, comprising both in vitro and in vivo procedure. Thus, an expression cassette of the invention or an vector comprising such expression cassette may by realized using standard recombination and cloning techniques well known in the art (see e.g., Maniatis 1989; Silhavy 1984; Ausubel 1987).

An expression cassette may also be assembled by inserting a transcription regulating nucleotide sequence of the invention (for example a sequence as described by SEQ ID NO: 1, 2, 3, 6, 7, 8, 11, 12, 15, 16, 17, 20, 21, 24, 25, 28, 31, 32, 35, or 36 ) into the plant genome. Such insertion will result in an operable linkage to a nucleic acid sequence of interest which as such already existed in the genome. By the insertion the nucleic acid of interest is expressed in a meristem-preferential or meristem-specific way due to the transcription regulating properties of the transcription regulating nucleotide sequence. The insertion may be directed or by chance. Preferably the insertion is directed and realized by for example homologous recombination. By this procedure a natural promoter may be exchanged against the transcription regulating nucleotide sequence of the invention, thereby modifying the expression profile of an endogenous gene. The transcription regulating nucleotide sequence may also be inserted in a way, that antisense mRNA of an endogenous gene is expressed, thereby inducing gene silencing.

Similar, a nucleic acid sequence of interest to be expressed may be inserted into a plant genome comprising the transcription regulating nucleotide sequence in its natural genomic environment (i.e. linked to its natural gene) in a way that the inserted sequence becomes operably linked to the transcription regulating nucleotide sequence, thereby forming an expression cassette of the invention.

The open reading frame to be linked to the transcription regulating nucleotide sequence of the invention may be obtained from an insect resistance gene, a disease resistance gene such as, for example, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a positive selectable marker, a gene affecting plant agronomic characteristics, i.e., yield, standability, and the like, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like. By "resistant" is meant a plant which exhibits substantially no phenotypic changes as a consequence of agent administration, infection with a pathogen, or exposure to stress. By "tolerant" is meant a plant which, although it may exhibit some phenotypic changes as a consequence of infection, does not have a substantially decreased reproductive capacity or substantially altered metabolism.

Meristem-preferential or meristem-specific transcription regulating nucleotide sequences (e.g., promoters) are useful for expressing a wide variety of genes including those which alter metabolic pathways, confer disease resistance, for protein production, e.g., antibody production, or to improve nutrient uptake and the like. Meristem-preferential or meristem-specific transcription regulating nucleotide sequences (e.g., promoters) may be modified so as to be regulatable, e.g., inducible. The genes and transcription regulating nucleotide sequences (e.g., promoters) described hereinabove can be used to identify orthologous genes and their transcription regulating nucleotide sequences (e.g., promoters) which are also likely expressed in a particular tissue and/or development manner. Moreover, the orthologous transcription regulating nucleotide sequences (e.g., promoters) are useful to express linked open reading frames. In addition, by aligning the transcription regulating nucleotide sequences (e.g., promoters) of these orthologs, novel cis elements can be identified that are useful to generate synthetic transcription regulating nucleotide sequences (e.g., promoters).

The expression regulating nucleotide sequences specified above may be optionally operably linked to other suitable regulatory sequences, e.g., a transcription terminator sequence, operator, repressor binding site, transcription factor binding site and/or an enhancer.

The present invention further provides a recombinant vector containing the expression cassette of the invention, and host cells comprising the expression cassette or vector, e.g., comprising a plasmid. The expression cassette or vector may augment the genome of a transformed plant or may be maintained extra chromosomally. The expression cassette or vector of the invention may be present in the nucleus, chloroplast, mitochondria and/or plastid of the cells of the plant. Preferably, the expression cassette or vector of the invention is comprised in the chromosomal DNA of the plant nucleus. The present invention also provides a transgenic plant prepared by this method, a seed from such a plant and progeny plants from such a plant including hybrids and inbreds. The expression cassette may be operatively linked to a structural gene, the open reading frame thereof, or a portion thereof. The expression cassette may further comprise a Ti plasmid and be contained in an *Agrobacterium tumefaciens* cell; it may be carried on a microparticle, wherein the microparticle is suitable for ballistic transformation of a plant cell; or it may be contained in a plant cell or protoplast. Further, the expression cassette or vector can be contained in a transformed plant or cells thereof, and the plant may be a dicot or a monocot. In particular, the plant may be a dicotyledonous plant. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

The invention also provides a method of plant breeding, e.g., to prepare a crossed fertile transgenic plant. The method comprises crossing a fertile transgenic plant comprising a particular expression cassette of the invention with itself or with a second plant, e.g., one lacking the particular expression cassette, to prepare the seed of a crossed fertile transgenic plant comprising the particular expression cassette. The seed is then planted to obtain a crossed fertile transgenic plant. The plant may be a monocot or a dicot. In a particular embodiment, the plant is a dicotyledonous plant. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The transcription regulating nucleotide sequences of the invention further comprise sequences which are complementary to one (hereinafter "test" sequence) which hybridizes under stringent conditions with a nucleic acid molecule as described by SEQ ID NO: 1, 2, 3, 6, 7, 8, 11, 12, 15, 16, 17, 20, 21, 24, 25, 28, 31, 32, 35, or 36 as well as RNA which is transcribed from the nucleic acid molecule. When the hybridization is performed under stringent conditions, either the test or nucleic acid molecule of invention is preferably supported, e.g., on a membrane or DNA chip. Thus, either a denatured test or nucleic acid molecule of the invention is preferably first bound to a support and hybridization is effected for a specified period of time at a temperature of, e.g., between 55 and 70° C., in double strength citrate buffered saline (SC) containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one-tenth strength SC containing 0.1% SDS. More preferably hybridization is carried out under high stringency conditions (as defined above).

Virtually any DNA composition may be used for delivery to recipient plant cells, e.g., dicotyledonous cells, to ultimately produce fertile transgenic plants in accordance with the present invention. For example, DNA segments or fragments in the form of vectors and plasmids, or linear DNA segments or fragments, in some instances containing only the DNA element to be expressed in the plant, and the like, may be employed. The construction of vectors which may be employed in conjunction with the present invention will be known to those of skill of the art in light of the present disclosure (see, e.g., Sambrook 1989; Gelvin 1990).

Vectors, plasmids, cosmids, YACs (yeast artificial chromosomes), BACs (bacterial artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment, fragment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki 1991). These vectors are capable of autonomous replication in maize cells as well as *E. coli,* and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs 1990) that transposition of these elements within the maize genome requires DNA replication. It is also contemplated that transposable elements would be useful for introducing DNA segments or fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells. The use of a transposable element such as Ac, Ds, or Mu may actively promote integration of the DNA of interest and hence increase the frequency of stably transformed cells. Transposable elements may be useful to allow separation of genes of interest from elements necessary for selection and maintenance of a plasmid vector in bacteria or selection of a transformant. By use of a transposable element, desirable and undesirable DNA sequences may be transposed apart from each other in the genome, such that through genetic segregation in progeny, one may identify plants with either the desirable undesirable DNA sequences.

The nucleotide sequence of interest linked to one or more of the transcription regulating nucleotide sequences of the invention can, for example, code for a ribosomal RNA, an antisense RNA or any other type of RNA that is not translated into protein. In another preferred embodiment of the invention, said nucleotide sequence of interest is translated into a protein product. The transcription regulating nucleotide sequence and/or nucleotide sequence of interest linked thereto may be of homologous or heterologous origin with respect to the plant to be transformed. A recombinant DNA molecule useful for introduction into plant cells includes that which has been derived or isolated from any source, that may be subsequently characterized as to structure, size and/or function, chemically altered, and later introduced into plants. An example of a nucleotide sequence or segment of interest "derived" from a source, would be a nucleotide sequence or segment that is identified as a useful fragment within a given organism, and which is then chemically synthesized in essentially pure form. An example of such a nucleotide sequence or segment of interest "isolated" from a source, would be nucleotide sequence or segment that is excised or removed from said source by chemical means, e.g., by the use of restriction endonucleases, so that it can be further manipulated, e.g., amplified, for use in the invention, by the methodology of genetic engineering. Such a nucleotide sequence or segment is commonly referred to as "recombinant."

Therefore a useful nucleotide sequence, segment or fragment of interest includes completely synthetic DNA, semisynthetic DNA, DNA isolated from biological sources, and DNA derived from introduced RNA. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced recombinant DNA molecule includes but is not limited to, DNA from plant genes, and non-plant genes such as those from bacteria, yeasts, animals or viruses. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the resultant plant. Generally, the introduced recombinant DNA molecule will be relatively small, i.e., less than about 30 kb to minimize any susceptibility to physical, chemical, or enzymatic degradation which is known to increase as the size of the nucleotide molecule increases. As noted above, the number of proteins, RNA transcripts or mixtures thereof which is introduced into the plant genome is preferably preselected and defined, e.g., from one to about 5-10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

It is specifically contemplated by the inventors that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment encoding a promoter sequence of the current invention are well-known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids also are routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein; the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Rarnstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences which are shared among promoters with similar expression patterns are likely candidates for the binding of transcription factors and are thus likely elements which confer expression patterns. Confirmation of these putative regulatory elements can be achieved by deletion analysis of each putative regulatory region followed by functional analysis of each deletion construct by assay of a reporter gene which is functionally attached to each construct. As such, once a starting promoter sequence is provided, any of a number of different deletion mutants of the starting promoter could be readily prepared.

Functionally equivalent fragments of a transcription regulating nucleotide sequence of the invention can also be obtained by removing or deleting non-essential sequences without deleting the essential one. Narrowing the transcription regulating nucleotide sequence to its essential, transcription mediating elements can be realized in vitro by trial-and-arrow deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the BIOBASE database "Transfac" (Biologische Datenbanken GmbH, Braunschweig; Wingender 2001) or the database PlantCARE (Lescot 2002).

Preferably, functional equivalent fragments of one of the transcription regulating nucleotide sequences of the invention comprises at least 100 base pairs, preferably, at least 200 base pairs, more preferably at least 500 base pairs of a transcription regulating nucleotide sequence as described by SEQ ID NO: 1, 2, 3, 6, 7, 8, 11, 12, 15, 16, 17, 20, 21, 24, 25, 28, 31, 32, 35, or 36 . More preferably this fragment is starting from the 3'-end of the indicated sequences.

Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating nucleotide sequences of the invention are equivalent fragments of other sequences (see Table 2 below).

TABLE 2

Relationship of transcription regulating nucleotide sequences of the invention

| Transcription regulating sequence | Equivalent sequence | Equivalent fragment |
| --- | --- | --- |
| SEQ ID NO: 1 (1630 bp) | SEQ ID NO: 2 (1631 bp) | SEQ ID NO: 3 (1200 bp) |
| SEQ ID NO: 6 (510 bp) | SEQ ID NO: 7 (511 bp) | SEQ ID NO: 8 (396 bp) |
| SEQ ID NO: 11 (2552 bp) | SEQ ID NO: 12 (2552 bp) | — |
| SEQ ID NO: 17 (2658 bp) | — | SEQ ID NO: 15 (2193 bp) |
|  |  | SEQ ID NO: 16 (2192 bp) |
| SEQ ID NO: 20 (2219 bp) | SEQ ID NO: 21 (2218 bp) | — |
| SEQ ID NO: 24 (2042 bp) | SEQ ID NO: 25 (2044 bp) | — |
| SEQ ID NO: 28 (2092 bp) | — | — |
| SEQ ID NO: 31 (2512 bp) | SEQ ID NO: 32 (2512 bp) | — |
| SEQ ID NO: 35 (1854 bp) | SEQ ID NO: 36 (1855 bp) | — |

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter or intron construct which contains a deleted segment to a selectable or screenable marker, and to isolate only those cells expressing the marker gene. In this way, a number of different, deleted promoter constructs are identified which still retain the desired, or even enhanced, activity. The smallest segment which is required for activity is thereby identified through comparison of the selected constructs. This segment may then be used for the construction of vectors for the expression of exogenous genes.

An expression cassette of the invention may comprise further regulatory elements. The term in this context is to be understood in the a broad meaning comprising all sequences which may influence construction or function of the expression cassette. Regulatory elements may for example modify transcription and/or translation in prokaryotic or eukaryotic organism. In an preferred embodiment the expression cassette of the invention comprised downstream (in 3'-direction) of the nucleic acid sequence to be expressed a transcription termination sequence and—optionally additional regulatory elements—each operably liked to the nucleic acid sequence to be expressed (or the transcription regulating nucleotide sequence).

Additional regulatory elements may comprise additional promoter, minimal promoters, or promoter elements, which may modify the expression regulating properties. For example the expression may be made depending on certain stress factors such water stress, abscisin (Lam 1991) or heat stress (Schoffl 1989). Furthermore additional promoters or promoter elements may be employed, which may realized expression in other organisms (such as E.coli or Agrobacterium). Such regulatory elements can be find in the promoter sequences or bacteria such as amy and SPO2 or in the promoter sequences of yeast or fungal promoters (such as ADC1, MFa, AC, P-60, CYC1, GAPDH, TEF, rp28, and ADH).

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters which are useful for plant transgene expression include those that are inducible, viral, synthetic, constitutive (Odell 1985), temporally regulated, spatially regulated, tissue-specific, and spatial-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens,* and the 3' end of the protease inhibitor I or II genes from potato or tomato, although other 3' elements known to those of skill in the art can also be employed. Alternatively, one also could use a gamma coixin, oleosin 3 or other terminator from the genus *Coix.*

Preferred 3' elements include those from the nopaline synthase gene of *Agrobacterium tumefaciens* (Bevan 1983), the terminator for the T7 transcript from the octopine synthase gene of *Agrobacterium tumefaciens,* and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Preferred regulatory elements also include the 5'-untranslated region, introns and the 3'-untranslated region of genes. Such sequences that have been found to enhance gene expression in transgenic plants include intron sequences (e.g., from Adh1, bronze1, actin1, actin 2 (WO 00/760067), or the sucrose synthase intron; see: The Maize Handbook, Chapter 116, Freeling and Walbot, Eds., Springer, New York (1994)) and viral leader sequences (e.g., from TMV, MCMV and AMV; Gallie 1987). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie 1987; Skuzeski 1990). Other leaders known in the art include but are not limited to: Picornavirus leaders, for example, EMCV leader (Encephalomyocarditis 5' noncoding region) (Elroy-Stein 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak 1991); Untranslated leader from the coat protein mRNA of alfalfa mosaic virus (AMV RNA 4), (Jobling 1987; Tobacco mosaic virus leader (TMV), (Gallie 1989; and Maize Chlorotic Mottle Virus leader (MCMV) (Lommel 1991. See also, Della-Cioppa 1987. Regulatory elements such as Adh intron 1 (Callis 1987), sucrose synthase intron (Vasil 1989) or TMV omega element (Gallie 1989), may further be included where desired. Especially preferred are the 5'-untranslated region, introns and the 3'-untranslated region from the genes described by the GenBank *Arabidopsis thaliana* genome locii At2g02180, At5g54510, At2g26970, At2g01180, At3g45560, At4g00580, At1g54480, or At4g11490, or the *Arabidopsis thaliana* genomic sequences as described by SEQ ID NO: 35 or 36, or of functional equivalent thereof.

Additional preferred regulatory elements are enhancer sequences or polyadenylation sequences. Preferred polyadenylation sequences are those from plant genes or *Agrobacterium* T-DNA genes (such as for example the terminator sequences of the OCS (octopine synthase) or NOS (nopaline synthase) genes).

Examples of enhancers include elements from the CaMV 35S promoter, octopine synthase genes (Ellis el al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Vectors for use in accordance with the present invention may be constructed to include the ocs enhancer element. This element was first identified as a 16 bp palindromic enhancer from the octopine synthase (ocs) gene of ultilane (Ellis 1987), and is present in at least 10 other promoters (Bouchez 1989). The use of an enhancer element, such as the ocs elements and particularly multiple copies of the element, will act to increase the level of transcription from adjacent promoters when applied in the context of plant transformation.

An expression cassette of the invention (or a vector derived therefrom) may comprise additional functional elements, which are to be understood in the broad sense as all elements which influence construction, propagation, or function of an expression cassette or a vector or a transgenic organism comprising them. Such functional elements may include origin of replications (to allow replication in bacteria; for the ORI of pBR322 or the P15A ori; Sambrook 1989), or elements required for *Agrobacterium* T-DNA transfer (such as for example the left and/or rights border of the T-DNA).

Ultimately, the most desirable DNA segments for introduction into, for example, a dicot genome, may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the expression of a gene in a meristem-preferential or meristem-specific manner.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and will then be posttranslationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site specific integration. For example, it would be useful to have an gene introduced through transformation replace an existing gene in the cell. Other elements include those that can be regulated by endogenous or exogenous agents, e.g., by zinc finger proteins, including naturally occurring zinc finger proteins or chimeric zinc finger proteins (see, e.g., U.S. Pat. No. 5,789, 538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences which bind to a specific DNA sequence (the zinc finger) and amino acid sequences that activate (e.g., GAL 4 sequences) or repress the transcription of the sequences linked to the specific DNA sequence.

It is one of the objects of the present invention to provide recombinant DNA molecules comprising a nucleotide sequence according to the invention operably linked to a nucleotide segment of interest.

A nucleotide segment of interest is reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of nucleotides of interest include, for example, genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences which may be linked to the gene of interest which encodes a polypeptide are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used. For examples of plastid organelle targeting sequences (see WO 00/12732). Plastids are a class of plant organelles derived from proplastids and include chloroplasts, leucoplasts, amyloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular, genome, most of the proteins localized to the plastids are encoded by the nuclear genome and are imported into the organelle from the cytoplasm.

Transgenes used with the present invention will often be genes that direct the expression of a particular protein or polypeptide product, but they may also be nonexpressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of transformation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or colinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male: sterility, drydown, standability, prolificacy, starch properties, oil quantity and quality, or those increasing yield or nutritional quality may be employed as desired.

1. Exemplary Transgenes 1.1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes. The deh gene encodes the enzyme dalapon dehalogenase and confers resistance to the herbicide dalapon. The bxn gene codes for a specific nitrilase enzyme that converts bromoxynil to a non-herbicidal degradation product.

1.2 Insect Resistance

An important aspect of the present invention concerns the introduction of insect resistance-conferring genes into plants. Potential insect resistance genes which can be introduced include *Bacillus thuringiensis* crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CrylA(b) and CrylA(c) genes. Endotoxin genes from other species of *B. thuringiensis* which affect insect growth or development may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes which encode inhibitors of the insects' digestive system, or those that encode enzymes or co-factors that facilitate the production of inhibitors, may also be useful. This group may be exemplified by cystatin and amylase inhibitors, such as those from wheat and barley.

Also, genes encoding lectins may confer additional or alternative insecticide properties. Lectins (originally termed phytohemagglutinins) are multivalent carbohydrate-binding proteins which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987) which may be used as a rootworm deterrent; genes encoding avermectin (Campbell 1989; Ikeda 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

1.3 Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically-active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loomis 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes which are not sugars include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive or tissue-specific expression of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from *Myoxocephalus scorpius* (WO 00/00512), *Myoxocephalus octodecemspinosus,* the *Arabidopsis thaliana* transcription activator CBF1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREBLA factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

1.4 Disease Resistance

It is proposed that increased resistance to diseases may be realized through introduction of genes into plants period. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are beta-1,3-glucanases, chitinases, and osmotin and other proteins that are believed to function in plant resistance to disease organisms. Other genes have been identified that have antifungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P-450 (CYP79) protein from *Sorghum bicolor* (GenBank Acc. No.: U32624), or functional equivalents of these.

The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77). The expression of synthetic crylA(b) and crylA(c) genes, which encode lepidoptera-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164).

1.5 Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plant of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field. Delay of late season vegetative senescence would increase the flow of assimilate into the grain and thus increase yield. Overexpression of genes within plants that are associated with "stay green" or the expression of any gene that delays senescence would be advantageous. For example, a non-yellowing mutant has been identified in *Festuca pratensis* (Davies 1990). Expression of this gene as well as others may prevent premature breakdown of chlorophyll and thus maintain canopy function.

1.6 Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

1.7. Non-Protein-Expressing Sequences 1.7.1 RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA or double-stranded RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Expression of antisense-RNA or double-stranded RNA by one of the expression cassettes of the invention is especially preferred. Also expression of sense RNA can be employed for gene silencing (co-suppression). This RNA is preferably a non-translatable RNA. Gene regulation by double-stranded RNA ("double-stranded RNA interference"; dsRNAi) is well known in the arte and described for various organism including plants (e.g., Matzke 2000; Fire A et al 1998; WO 99/32619; WO 99/53050; WO 00/68374; WO 00/44914; WO 00/44895; WO 00/49035; WO 00/63364).

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants which possess them. The transgenic plants may possess reduced levels of polypeptides including but not limited to the polypeptides cited above that may be affected by antisense RNA.

It is also possible that genes may be introduced to produce novel transgenic plants which have reduced expression of a native gene product by a mechanism of cosuppression. It has been demonstrated in tobacco, tomato, and petunia (Goring 1991; Smith 1990; Napoli 1990; van der Krol 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

1.7.2 Non-RNA-Expressing

For example, DNA elements including those of transposable elements such as Ds, Ac, or Mu, may be, inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element which may be introduced is a matrix attachment region element (MAR), such as the chicken lysozyme A element (Stief 1989), which can be positioned around an expressible gene of interest to effect an increase in overall expression of the gene and diminish position dependant effects upon incorporation into the plant genome (Stief 1989; Phi-Van 1990).

Further nucleotide sequences of interest that may be contemplated for use within the scope of the present invention in operable linkage with the promoter sequences according to the invention are isolated nucleic acid molecules, e.g., DNA or RNA, comprising a plant nucleotide sequence according to the invention comprising an open reading frame that is preferentially expressed in a specific tissue, i.e., meristem-, root, green tissue (leaf and stem), panicle-, or pollen, or is expressed constitutively.

2. Marker Genes

In order to improve the ability to identify transformants, one may desire to employ a selectable or screenable marker gene as, or in addition to, the expressible gene of interest.

"Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel 1990) molecule is well characterized in terms of molecular biology, expression and protein structure. However, any one of a variety of ultilane and/or glycine-rich wall proteins (Keller 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

2.1 Selectable Markers

Various selectable markers are known in the art suitable for plant transformation. Such markers may include but are not limited to:

2.1.1 Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide) which suppresses growth of an untransformed wild type tissue. Especially preferred negative selection markers are those which confer resistance to herbicides. Examples which may be mentioned are:

Phosphinothricin acetyltransferases (PAT; also named Bialophos®resistance; bar; de Block 1987; Vasil 1992, 1993; Weeks 1993; Becker 1994; Nehra 1994; Wan & Lemaux 1994; EP 0 333 033; U.S. Pat. No. 4,975,374). Preferred are the bar gene from *Streptomyces hygroscopicus* or the pat gene from *Streptomyces viridochromogenes*. PAT inactivates the active ingredient in the herbicide bialaphos, phosphinothricin (PPT). PPT inhibits glutamine synthetase, (Murakami 1986; Twell 1989) causing rapid accumulation of ammonia and cell death.

altered 5-enolpyruvylshikimate-3-phosphate synthase (EPSPS) conferring resistance to Glyphosate® (N-(phosphonomethyl)glycine) (Hinchee 1988; Shah 1986; Della-Cioppa 1987). Where a mutant EPSP synthase gene is employed, additional benefit may be realized through the incorporation of a suitable chloroplast transit peptide, CTP (EP-A1 0 218 571).

Glyphosate® degrading enzymes (Glyphosate® oxidoreductase; gox),

Dalapon® inactivating dehalogenases (deh)

sulfonylurea- and/or imidazolinone-inactivating acetolactate synthases (ahas or ALS; for example mutated ahas/ALS variants with, for example, the S4, XI12, XA17, and/or Hra mutation (EP-A1 154 204)

Bromoxynil® degrading nitrilases (bxn; Stalker 1988)

Kanamycin- or geneticin (G418) resistance genes (NPTII; NPT or neo; Potrykus 1985) coding e.g., for neomycin phosphotransferases (Fraley 1983; Nehra 1994)

2-Desoxyglucose-6-phosphate phosphatase ($DOG^R1$-Gene product; WO 98/45456; EP 0 807 836) conferring resistance against 2-desoxyglucose (Randez-Gil 1995).

hygromycin phosphotransferase (HPT), which mediates resistance to hygromycin (Vanden Elzen 1985).

altered dihydrofolate reductase (Eichholtz 1987) conferring resistance against methotrexat (Thillet 1988);

mutated anthranilate synthase genes that confers resistance to 5-methyl tryptophan.

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the daol gene (EC: 1.4.3.3 : GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3. 1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinotricin resistance gene (bar) as the selective marker, phosphinotricin at a concentration of from about 1 to 50 mg/l may be included in the medium. For example, with the daol gene as the selective marker, D-serine or D-alanine at a concentration of from about 3 to 100 mg/l may be included in the medium. Typical concentrations for selection are 20 to 40 mg/l. For example, with the mutated ahas genes as the selective marker, PURSUIT™ at a concentration of from about 3 to 100 mg/l may be included in the medium. Typical concentrations for selection are 20 to 40 mg/l.

2.1.2 Positive Selection Marker

Furthermore, positive selection marker can be employed. Genes like isopentenyltransferase from *Agrobacterium tumefaciens* (strain:PO22; Genbank Acc.-No.: AB025109) may—as a key enzyme of the cytokinin biosynthesis—facilitate regeneration of transformed plants (e.g., by selection on cytokinin-free medium). Corresponding selection methods are described (Ebinuma 2000a,b). Additional positive selection markers, which confer a growth advantage to a transformed plant in comparison with a non-transformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2.1.3 Counter-Selection Marker

Counter-selection markers are especially suitable to select organisms with defined deleted sequences comprising said marker (Koprek 1999). Examples for counter-selection marker comprise thymidin kinases (TK), cytosine deaminases (Gleave 1999; Perera 1993; Stougaard 1993), cytochrom P450 proteins (Koprek 1999), haloalkan dehalogenases (Naested 1999), iaaH gene products (Sundaresan 1995), cytosine deaminase codA (Schlaman & Hooykaas 1997), tms2 gene products (Fedoroff & Smith 1993), or α-naphthalene acetamide (NAM; Depicker 1988). Counter selection markers may be useful in the construction of transposon tagging lines. For example, by marking an autonomous transposable element such as Ac, Master Mu, or En/Spn with a counter selection marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

2.2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta 1988); a beta-lactamase gene (Sutcliffe 1978), which encodes an enzyme for which various chromogenic substrates are known (e.g., PADAC, a chromogenic cephalosporin); a xylE gene (Zukowsky 1983) which encodes a catechol dioxygenase that can convert chromogenic catechols; an α-amylase gene (Ikuta 1990); a tyrosinase gene (Katz 1983) which encodes an enzyme capable of oxidizing tyrosine to DOPA and dopaquinone which in turn condenses to form the easily detectable compound melanin; β-galactosidase gene, which encodes an enzyme for which there are chromogenic substrates; a luciferase (lux) gene (Ow 1986), which allows for bioluminescence detection; or even an aequorin gene (Prasher 1985), which may be employed in calcium-sensitive bioluminescence detection, or a green fluorescent protein gene (Niedz 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is dominant for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

3. Exemplary DNA Molecules

The invention provides an isolated nucleic acid molecule, e.g., DNA or RNA, comprising a plant nucleotide sequence comprising an open reading frame that is preferentially expressed in a specific plant tissue, i.e., in seeds, roots, green tissue (leaf and stem), panicles or pollen, or is expressed constitutively, or a promoter thereof.

These promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the Ptac promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of transformed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

Regulated expression of the chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the transacting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. 1997. Again, either the chimeric tRNA suppressor gene, the chimeric transacting replication gene, or both can be under the control of tissue- and developmental-specific or inducible promoters.

Frequently it is desirable to have continuous or inducible expression of a DNA sequence throughout the cells of an organism in a tissue-independent manner. For example, increased resistance of a plant t6 infection by soil- and airborne-pathogens might be accomplished by genetic manipulation of the plant's genome to comprise a continuous promoter operably linked to a heterologous pathogen-resistance gene such that pathogen-resistance proteins are continuously expressed throughout the plant's tissues.

Alternatively, it might be desirable to inhibit expression of a native DNA sequence within the seeds of a plant to achieve a desired phenotype. In this case, such inhibition might be accomplished with transformation of the plant to comprise a promoter operably linked to an antisense nucleotide sequence, such that meristem-preferential or meristem-specific expression of the antisense sequence produces an RNA transcript that interferes with translation of the mRNA of the native DNA sequence.

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins which are easily measured, including, but not limited to, chloramphenicol acetyl transferase (CAT), beta-glucuronidase (GUS), green fluorescent protein (GFP), beta-galactosidase (beta-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, such as by Northern blot analysis.

Once activity is detected, mutational and/or deletional analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

In one embodiment, the promoter may be a gamma zein promoter, an oleosin ole16 promoter, a globulins promoter, an actin I promoter, an actin cl promoter, a sucrose synthetase promoter, an INOPS promoter, an EXM5 promoter, a globulin2 promoter, a b-32, ADPG-pyrophosphorylase promoter, an Ltp1 promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter, an anther-specific gene RTS2 promoter, a pollen-specific gene promoter, a tapeturn-specific gene promoter, tapeturn-specific gene RAB24 promoter, a anthranilate synthase alpha subunit promoter, an alpha zein promoter, an anthranilate synthase beta subunit promoter, a dihydrodipicolinate synthase promoter, a Thil promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an atubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 34S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

4. Transformed (Transgenic) Plants of the Invention and Methods of Preparation

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems; axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) plant cell, in planta or ex planta, including a transformed plastid or other organelle, e.g., nucleus, mitochondria or chloroplast. The present invention may be used for transformation of any plant species, including, but not limited to, cells from the plant species specified above in the DEFINITION section. Preferably, transgenic plants of the present invention are crop plants and in particular cereals (for example, corn, alfalfa, sunflower, rice, *Brassica*, canola, soybean, barley, soybean, sugarbeet, cotton, safflower, peanut, sorghum, wheat, millet, tobacco, etc.), and even more preferably corn, rice and soybean. Other embodiments of the invention are related to cells, cell cultures, tissues, parts (such as plants organs, leaves, roots, etc.) and propagation material (such as seeds) of such plants.

The transgenic expression cassette of the invention may not only be comprised in plants or plant cells but may advantageously also be containing in other organisms such for example bacteria. Thus, another embodiment of the invention relates to transgenic cells or non-human, transgenic organisms comprising an expression cassette of the invention. Preferred are prokaryotic and eukaryotic organism. Both microorganism and higher organisms are comprised. Preferred microorganism are bacteria, yeast, algae, and fungi. Preferred bacteria are those of the genus *Escherichia, Erwinia, Agrobacterium, Flavobacterium, Alcaligenes, Pseudomonas, Bacillus* or *Cyanobacterim* such as—for example—*Synechocystis* and other bacteria described in Brock Biology of Microorganisms Eighth Edition (pages A-8, A-9, A10 and A11).

Especially preferred are microorganisms capable to infect plants and to transfer DNA into their genome, especially bacteria of the genus *Agrobacterium*, preferably *Agrobacterium tumefaciens* and *rhizogenes*. Preferred yeasts are *Candida, Saccharomyces, Hansenula* and *Pichia*. Preferred Fungi are *Aspergillus, Trichoderma, Ashbya, Neurospora, Fusarium,* and *Beauveria*. Most preferred are plant organisms as defined above.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art. Of particular relevance are the recently described methods to transform foreign genes into commercially important crops, such as rapeseed (De Block 1989), sunflower (Everett 1987), soybean (McCabe 1988; Hinchee 1988; Chee 1989; Christou 1989; EP 301749), rice (Hiei 1994), and corn (Gordon-Kamm 1990; Fromm 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway 1986), electroporation (Riggs 1986), *Agrobacterium*-mediated transformation (Hinchee 1988), direct gene transfer (Paszkowski 1984), and ballistic particle acceleration using devices available from Agracetus, Inc., Madison, Wis. And BioRad, Hercules, Calif. (see, for example, U.S. Pat. No. 4,945,050; and McCabe 1988). Also see, Weissinger 1988; Sanford 1987 (onion); Christou 1988 (soybean); McCabe 1988 (soybean); Datta 1990 (rice); Klein 1988 (maize); Klein 1988 (maize); Klein 1988 (maize); Fromm 1990 (maize); and Gordon-Kamm 1990 (maize); Svab 1990 (tobacco chloroplast); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab 1990; Staub 1992). This resulted in stable homoplasmic transformants at a frequency of approximately one per 100 bombardments of target leaves. The presence of cloning sites between these markers allowed creation of a plastid targeting vector for introduction of foreign genes (Staub 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3N-adenyltransferase (Svab 1993). Other selectable markers useful for plastid transformation are known in the art and encompassed within the scope of the invention. Typically, approximately 15-20 cell division cycles following transformation are required to reach a homoplastidic state. Plastid expression, in which genes are inserted by orthologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid targeting vector and transformed into the plastid genome of a desired plant host. Plants homoplastic for plastid genomes containing a nucleotide sequence of the present invention are obtained, and are preferentially capable of high expression of the nucleotide sequence.

*Agrobacterium tumefaciens* cells containing a vector comprising an expression cassette of the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known.

Various *Agrobacterium* strains can be employed, preferably disarmed *Agrobacterium tumefaciens* or *rhizogenes* strains. In a preferred embodiment, *Agrobacterium* strains for use in the practice of the invention include octopine strains, e.g., LBA4404 or agropine strains, e.g., EHA101 or EHA105. Suitable strains of *A. tumefaciens* for DNA transfer are for example EHA101[pEHA101] (Hood 1986), EHA105[pEHA105] (Li 1992), LBA4404[pAL4404] (Hoekema 1983), C58C1[pMP90] (Koncz & Schell 1986), and C58C1[pGV2260] (Deblaere 1985). Other suitable strains are *Agrobacterium tumefaciens* C58, a nopaline strain. Other suitable strains are *A. tumefaciens* C58C1 (Van Larebeke 1974), A136 (Watson 1975) or LBA4011 (Klapwijk 1980). In another preferred embodiment the soil-borne bacterium is a disarmed variant of *Agrobacterium rhizogenes* strain K599 (NCPPB 2659). Preferably, these strains are comprising a disarmed plasmid variant of a Ti- or Ri-plasmid providing the functions required for T-DNA transfer into plant cells (e.g., the vir genes). In a preferred embodiment, the *Agrobacterium* strain used to transform the plant tissue pre-cultured with the plant phenolic compound contains a L,L-succinamopine type Ti-plasmid, preferably disarmed, such as pEHA101. In another preferred embodiment, the *Agrobacterium* strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular *Agrobacterium* strains, to further increase the transformation efficiency, such as *Agrobacterium* strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of *Agrobacterium tumefaciens* strain LBA4404 (Hiei 1994) with super-virulent plasmids. These are preferably pTOK246-based vectors (Ishida 1996).

A binary vector or any other vector can be modified by common DNA recombination techniques, multiplied in *E. coli*, and introduced into *Agrobacterium* by e.g., electroporation or other transformation techniques (Mozo & Hooykaas 1991).

*Agrobacterium* is grown and used in a manner similar to that described in Ishida (1996). The vector comprising *Agrobacterium* strain may, for example, be grown for 3 days on YP medium (5 g/l yeast extract, 10 g/l peptone, 5 g/l NaCl, 15 g/l agar, pH 6.8) supplemented with the appropriate antibiotic (e.g., 50 mg/l spectinomycin). Bacteria are collected with a loop from the solid medium and resuspended. In a preferred embodiment of the invention, *Agrobacterium* cultures are started by use of aliquots frozen at −80° C.

The transformation of the target tissue (e.g., an immature embryo) by *Agrobacterium* may be carried out by merely contacting the target tissue with *Agrobacterium*. The concentration of *Agrobacterium* used for infection and co-cultivation may need to be varied. For example, a cell suspension of the *Agrobacterium* having a population density of approximately from $10^5$-$10^{11}$, preferably $10^6$ to $10^{10}$, more preferably about $10^8$ cells or cfu/ml is prepared and the target tissue is immersed in this suspension for about 3 to 10 minutes. The resulting target tissue is then cultured on a solid medium for several days together with the *Agrobacterium*.

Preferably, the bacterium is employed in concentration of $10^6$ to $10^{10}$ cfu/ml. In a preferred embodiment for the co-cultivation step about 1 to 10 µl of a suspension of the soil-borne bacterium (e.g., *Agrobacteria*) in the co-cultivation medium are directly applied to each target tissue explant and air-dried. This is saving labor and time and is reducing unintended *Agrobacterium*-mediated damage by excess *Agrobacterium* usage.

For *Agrobacterium* treatment, the bacteria are resuspended in a plant compatible co-cultivation medium. Supplementation of the co-culture medium with antioxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defence responses (like phenolic oxidation) may further improve the efficiency of *Agrobacterium*-mediated transformation. In another preferred embodiment, the co-cultivation medium of comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate. Preferably, the medium employed during co-cultivation comprises from about 1 µM to about 10 µM of silver nitrate and from about 50 mg/L to about 1,000 mg/L of L-Cystein. This results in a highly reduced vulnerability of the target tissue against *Agrobacterium*mediated damage (such as induced necrosis) and highly improves overall transformation efficiency.

Various vector systems can be used in combination with *Agrobacteria*. Preferred are binary vector systems. Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Methods using either a form of direct gene transfer or *Agrobacterium*-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 1990), the hph gene which confers resistance to the antibiotic hygromycin (Blochlinger & Diggelmann), and the dhfr gene, which confers resistance to methotrexate (Bourouis 1983).

5. Production and Characterization of Stably Transformed Plants

Transgenic plant cells are then placed in an appropriate selective medium for selection of transgenic cells which are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA which has been introduced. Components of DNA constructs including transcription cassettes of this invention may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using this technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the, genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment.

Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

6. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant which only differs in that the expression cassette is absent.

The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutriceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and transgenic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules. The transgenic plants may also be used in commercial breeding programs, or may be crossed or bred to plants of related crop species. Improvements encoded by the expression cassette may be transferred, e.g., from maize cells to cells of other species, e.g., by protoplast fusion.

The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multilane breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines which for example increase the effectiveness of conventional methods such as herbicide or pesticide treatment or allow to dispense with said methods due to their modified genetic properties. Alternatively new crops with improved stress tolerance can be obtained which, due to their optimized genetic "equipment", yield harvested product of better quality than products which were not able to tolerate comparable adverse developmental conditions.

EXAMPLES

Materials and General Methods

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of E. coli cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

For generating transgenic Arabidopsis plants Agrobacterium tumefaciens (strain C58C1[pMP90]) is transformed with the various promoter::GUS vector constructs (see below). Resulting Agrobacterium strains are subsequently employed to obtain transgenic plants. For this purpose a isolated transformed Agrobacterium colony is incubated in 4 ml culture (Medium: YEB medium with 50 µg/ml Kanamycin and 25 µg/ml Rifampicin) over night at 28° C. With this culture a 400 ml culture of the same medium is inoculated and incubated over night (28° C., 220 rpm). The bacteria a precipitated by centrifugation (GSA-Rotor, 8.000 U/min, 20 min) and the pellet is resuspended in infiltration medium (½ MS-Medium; 0,5 g/l MES, pH 5,8; 50 g/l sucrose). The suspension is placed in a plant box (Duchefa) and 100 ml SILVET L-77 (Osi Special-ties Inc., Cat. P030196) are added to a final concentration of 0.02%. The plant box with 8 to 12 Plants is placed into an exsiccator for 10 to 15 min. under vacuum with subsequent, spontaneous ventilation (expansion). This process is repeated 2-3 times. Thereafter all plants are transferred into pods with wet-soil and grown under long daytime conditions (16 h light; day temperature 22-24° C., night temperature 19° C.; 65% rel. humidity). Seeds are harvested after 6 weeks.

Example 1

Growth Conditions for Plants for Tissue-Specific Expression Analysis

To obtain 4 and 7 days old seedlings, about 400 seeds (Arabidopsis thaliana ecotype Columbia) are sterilized with a 80% (v/v) ethanol:water solution for 2 minutes, treated with a sodium hypochlorite solution (0.5% v/v) for 5 minutes, washed three times with distilled water and incubated at 4° C. for 4 days to ensure a standardized germination. Subsequently, seeds are incubated on Petri dishes with MS medium (Sigma M5519) supplemented with 1% sucrose, 0.5 g/l MES (Sigma M8652), 0.8% Difco-BactoAgar (Difco 0140-01), adjusted to pH 5.7. The seedlings are grown under 16 h light/8 h dark cyklus (Philips 58W/33 white light) at 22° C. and harvested after 4 or 7 days, respectively.

To obtain root tissue, 100 seeds are sterilized as described above, incubated at 4° C. for 4 days, and transferred into 250 ml flasks with MS medium (Sigma M5519) supplemented with additional 3% sucrose and 0.5 g/l MES (Sigma M8652), adjusted to pH 5.7 for further growing. The seedlings are grown at a 16 h light/8 h dark cycle (Philips 58W/33 white light) at 22° C. and 120 rpm and harvested after 3 weeks. For all other plant organs employed, seeds are sown on standard soil (Type VM, Manna-Italia, Via S. Giacomo 42, 39050 San Giacomo/Laives, Bolzano, Italien), incubated for 4 days at 4° C. to ensure uniform germination, and subsequently grown under a 16 h light/8 darkness regime (OSRAM Lumi-lux Daylight 36W/12) at 22° C. Young rosette leaves are harvested at the 8-leaf stage (after about 3 weeks), mature rosette leaves are harvested after 8 weeks briefly before stem formation. Apices of out-shooting stems are harvested briefly after out-shooting. Stem, stem leaves, and flower buds are harvested in development stage 12 (Bowmann J (ed.), *Arabidopsis,* Atlas of Morphology, Springer New York, 1995) prior to stamen development. Open flowers are harvested:in development stage 14 immediately after stamen development. Wilting flowers are harvested in stage 15 to 16. Green and yellow shoots used for the analysis have a length of 10 to 13 mm.

Example 2

Demonstration of Expression Profile

To demonstrate and analyze the transcription regulating properties of a promoter of the useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo-4-Chloro-3-indolyl-β-D-glucuronic acid during corresponding activity assays (Jefferson 1987). For determination of promoter activity and tissue specificity plant tissue is dissected, embedded, stained and analyzed as described (e.g., Baumlein 1991).

For quantitative β-glucuronidase activity analysis MUG (methylumbelliferyl glucuronide) is used as a substrate, which is converted into MU (methylumbelliferone) and glucuronic acid. Under alkaline conditions this conversion can be quantitatively monitored fluorometrically (excitation at 365 nm, measurement at 455 nm; SpectroFluorimeter Thermo Life Sciences Fluoroscan) as described (Bustos 1989).

Example 3

Cloning of the Promoter Fragments

To isolate the promoter fragments described by SEQ ID NO: 1, 2, 3, 6, 7, 8, 11, 12, 15, 16, 17, 20, 21, 24, 25, 28, 31, 32, 35, and 36, genomic DNA is isolated from *Arabidopsis thaliana* (ecotype Columbia) as described (Galbiati 2000). The isolated genomic DNA is employed as matrix DNA for a polymerase chain reaction (PCR) mediated amplification using the oligonucleotide primers and protocols indicated below (Table 3).

TABLE 3

PCR conditions and oligonucleotide primers for amplification of the various transcription regulating nucleotide sequences

| Seq ID No. | Promoter | Forward Primer | Reverse Primer | Ta | Restriction enzymes |
|---|---|---|---|---|---|
| SEQ ID NO: 1 | pSUH438 | UH438for SEQ ID NO: 37 | UH438rev SEQ ID NO: 38 | 52° C. | XhoI/NcoI |
| SEQ ID NO: 2 | pSUH438GB | UH438for SEQ ID NO: 37 | UH438rev SEQ ID NO: 38 | 52° C. | XhoI/NcoI |
| SEQ ID NO: 3 | pSUH438v | UH438vfor SEQ ID NO: 39 | UH438vrev SEQ ID NO: 40 | 55° C. | BamHI/NcoI |
| SEQ ID NO: 6 | pSUH436 | UH436for SEQ ID NO: 41 | UH436rev SEQ ID NO: 42 | 51° C. | BamHI/NcoI |
| SEQ ID NO: 7 | pSUH436GB | UH436for SEQ ID NO: 41 | UH436rev SEQ ID NO: 42 | 51° C. | BamHI/NcoI |
| SEQ ID NO: 8 | pSUH436S | UH436for SEQ ID NO: 41 | UH436Srev SEQ ID NO: 43 | 51° C. | BamHI/NcoI |
| SEQ ID NO: 11 | pSUH433 | UH433for SEQ ID NO: 44 | UH433rev SEQ ID NO: 45 | 54° C. | BamHI/NcoI |
| SEQ ID NO: 12 | pSUH433GB | UH433for SEQ ID NO: 44 | UH433rev SEQ ID NO: 45 | 54° C. | BamHI/NcoI |
| SEQ ID NO: 15 | pSUH415 | UH415for SEQ ID NO: 46 | UH415rev SEQ ID NO: 47 | 56° C. | BamHI/NcoI |
| SEQ ID NO: 16 | pSUH415GB | UH415for SEQ ID NO: 46 | UH415rev SEQ ID NO: 47 | 56° C. | BamHI/NcoI |
| SEQ ID NO: 17 | pSUH415L | UH415Lfor SEQ ID NO: 48 | UH415Lrev SEQ ID NO: 49 | 56° C. | XhoI/NcoI |
| SEQ ID NO: 20 | pSUH416 | UH416for SEQ ID NO: 50 | UH416rev SEQ ID NO: 51 | 54° C. | BamHI/NcoI |
| SEQ ID NO: 21 | pSUH416GB | UH416for SEQ ID NO: 50 | UH416rev SEQ ID NO: 51 | 54° C. | BamHI/NcoI |
| SEQ ID NO: 24 | pSUH417 | UH417for SEQ ID NO: 52 | UH417rev SEQ ID NO: 53 | 57° C. | BamHI/NcoI |
| SEQ ID NO: 25 | pSUH417GB | UH417for SEQ ID NO: 52 | UH417rev SEQ ID NO: 53 | 57° C. | BamHI/NcoI |
| SEQ ID NO: 28 | pSUH432 | UH432for SEQ ID NO: 54 | UH432rev SEQ ID NO: 55 | 52° C. | BamHI/SpeI |
| SEQ ID NO: 31 | pSUH431 | UH431for SEQ ID NO: 56 | UH431rev SEQ ID NO: 57 | 56° C. | XhoI/BamHI |
| SEQ ID NO: 32 | pSUH431GB | UH431for SEQ ID NO: 56 | UH431rev SEQ ID NO: 57 | 56° C. | XhoI/BamHI |

TABLE 3-continued

PCR conditions and oligonucleotide primers for amplification of the various transcription regulating nucleotide sequences

| Seq ID No. | Promoter | Forward Primer | Reverse Primer | Ta | Restriction enzymes |
|---|---|---|---|---|---|
| SEQ ID NO: 35 | pSUH413 | UH413for SEQ ID NO: 58 | UH413rev SEQ ID NO: 59 | 49° C. | XhoI/NcoI |
| SEQ ID NO: 36 | pSUH413GB | UH413for SEQ ID NO: 58 | UH413rev SEQ ID NO: 59 | 49° C. | XhoI/NcoI |

Amplification is carried out as follows:
100 ng genomic DNA
1×PCR buffer
2.5 mM MgCl$_2$,
200 µM each of dATP, dCTP, dGTP und dTTP
10 pmol of each oligonucleotide primers
2.5 Units Pfu DNA Polymerase (Stratagene)
in a final volume of 50 µl
The following temperature program is employed for the various amplifications (BIORAD Thermocycler).
1. 95° C. for 5 min
2. Ta° C. for 1 min, followed by 72° C. for 5 min and 95° C. for 30 sec. Repeated 25 times.
3. Ta° C. for 1 min, followed by 72° C. for 10 min.
4. Storage at 4° C.

The resulting PCR-products are digested with the restriction endonucleases specified in the Table above (Table 3) and cloned into the vector pSUN0301 (SEQ ID NO: 60) (pre-digested with the same enzymes) upstream and in operable linkage to the glucuronidase (GUS) gene. Following stable transformation of each of these constructs into *Arabidopsis thaliana* tissue specificity and expression profile was analyzed by a histochemical and quantitative GUS-assay, respectively.

Example 4

Expression Profile of the Various Promoter::GUS Constructs in Stably Transformed *A. thaliana* Plants 4.1 pSUH415, pSUH415L and pSUH415GB The promoter sequences derived from gene At2g01180 confer a strong expression in shoot apical meristems of seedlings, in vegetative shoot meristems of young plants as well in primordia of lateral roots. No expression is observed in leaves, stem, flowers, shoots and seeds.

4.2 pSUH416 and pSUH416GB

The promoter sequences derived from gene At3g45560 confer a strong expression in shoot apical meristems of seedlings, in vegetative shoot meristems of young plants as well in marginal meristems. No expression is observed in seedlings, leaves, stem, flowers, shoots and seeds.

4.3 pSUH413, and pSUH413GB

The promoter sequences demonstrate an extraordinary strong expression in hypocotyls and in the apical meristem region of seedlings. In adult plants expression is observed in meristematic tissues of nodes, in interface between petioles and siliques and in branching points of petioles of inflorescences. Weak side activities are observed in vasculature tissue of leaves. No expression is observed in leaves, stem, flowers, shoots and seeds.

4.4 pSUH438, pSUH438v and pSUH438GB

The promoter sequences derived from gene At2g02180 confer a strong expression in shoot apical meristems of seedlings, in vegetative shoot meristems of young plants as well in root tips. There are side activities in main vein of hypocotyl and roots of seedlings. No expression is observed in leaves, stem, flowers, shoots and seeds.

4.5 pSUH431 and pSUH431 GB

The promoter sequences derived from gene At4g11490 drive expression in shoot apical meristems in seedlings. In adult plants expression is observed in shoot meristems of nodes and in branching points of petioles of inflorescences. There are side activities in anthers. No expression is observed in leaves, stem, flowers, shoots and seeds.

4.6 pSUH417 and pSUH417GB

The promoter sequences derived from gene At4g00580 drive expression in shoot apical meristems of seedlings. In adult plants expression is observed in vegetative shoot meristems and in interface between petioles and siliques. No expression is observed in leaves, stem, flowers, shoots and seeds.

4.7 pSUH432

The promoter sequences derived from gene At1g54480 drive expression in shoot apical meristems. No expression is observed in leaves, stem, flowers, shoots and seeds.

4.8 pSUH433 and pSUH433GB

The promoter sequences derived from gene At2g26970 confer strong expression in shoot apex of seedlings. In adult plants expression is observed in shoot apex shoot meristems of nodes and in interface between petioles and siliques. There are side activities in root tips. No expression is observed in leaves, stem, flowers, shoots and seeds.

4.9 pSUH436, pSUH436S and pSUH436GB

The promoter sequences derived from gene At5g54510 demonstrate strong expression in shoot apex of seedlings. In adult plants expression is observed in shoot apex shoot meristems of nodes and in interface between petioles and siliques. There are side activities in root tips. No expression is observed in leaves, stem, flowers, shoots and seeds.

Example 5

Vector Construction for Overexpression and Gene "Knockout" Experiments 5.1 Overexpression Vectors used for expression of full-length "candidate genes" of interest in plants (over-expression) are designed to overexpress the protein of interest and are of two general types, biolistic and binary, depending on the plant transformation method to be used.

For biolistic transformation (biolistic vectors), the requirements are as follows:
1. a backbone with a bacterial selectable marker (typically, an antibiotic resistance gene) and origin of replication functional in *Escherichia coli* (*E. coli*; e.g., ColE1), and
2. a plant-specific portion consisting of:
   a. a gene expression cassette consisting of a promoter (eg. ZmUBlint MOD), the gene of interest (typically, a full-length cDNA) and a transcriptional terminator (e.g., *Agrobacterium tumefaciens* nos terminator);
   b. a plant selectable marker cassette, consisting of a suitable promoter, selectable marker gene (e.g., D-amino acid oxidase; dao1) and transcriptional terminator (eg. nos terminator).

Vectors designed for transformation by *Agrobacterium tumefaciens* (*A. tumefaciens*; binary vectors) consist of:
1. a backbone with a bacterial selectable marker functional in both *E. coli* and *A. tumefaciens* (e.g., spectinomycin resistance mediated by the aadA gene) and two origins of replication, functional in each of aforementioned bacterial hosts, plus the *A. tumefaciens* virG gene;
2. a plant-specific portion as described for biolistic vectors above, except in this instance this portion is flanked by A. tumefaciens right and left border sequences which mediate transfer of the DNA flanked by these two sequences to the plant.

5.2 Gene Silencing Vectors

Vectors designed for reducing or abolishing expression of a single gene or of a family or related genes (gene silencing vectors) are also of two general types corresponding to the methodology used to downregulate gene expression: antisense or double-stranded RNA interference (dsRNAi).

(a) Anti-Sense

For antisense vectors, a full-length or partial gene fragment (typically, a portion of the cDNA) can be used in the same vectors described for full-length expression, as part of the gene expression cassette. For antisense-mediated downregulation of gene expression, the coding region of the gene or gene fragment will be in the opposite orientation relative to the promoter; thus, mRNA will be made from the noncoding (antisense) strand in planta.

(b) dsRNAi

For dsRNAi vectors, a partial gene fragment (typically, 300 to 500 basepairs long) is used in the gene expression cassette, and is expressed in both the sense and antisense orientations, separated by a spacer region (typically, a plant intron, eg. the OsSH1 intron 1, or a selectable marker, eg. conferring kanamycin resistance). Vectors of this type are designed to form a double-stranded mRNA stem, resulting from the basepairing of the two complementary gene fragments in planta.

Biolistic or binary vectors designed for overexpression or knockout can vary in a number of different ways, including eg. the selectable markers used in plant and bacteria, the transcriptional terminators used in the gene expression and plant selectable marker cassettes, and the methodologies used for cloning in gene or gene fragments of interest (typically, conventional restriction enzyme-mediated or Gateway™ recombinase-based cloning).

REFERENCES

1. Abel et al., Science, 232:738 (1986).
2. Altschul et al., Nucleic Acids Res., 25:3389 (1997).
3. Altschul et al., J. Mol. Biol., 215:403 (1990).
4. An et al., EMBO J., 4:277 (1985).
5. Auch & Reth, Nucleic Acids Research, 18:6743 (1990).
6. Ausubel et al. (1987) Current Protocols in Molecular Biology, Greene Publishing Assoc. and Wiley Interscience
7. Ballas et al., Nucleic Acids Res., 17:7891 (1989).
8. Barkai-Golan et al., Arch. Microbiol., 116:119 (1978).
9. Batzer et al., Nucleic Acid Res., 19:5081 (1991).
10. Bäumlein et al. Mol Gen Genet 225:121-128 (1991)
11. Becker et al. (1994) Plant J., 5:299-307,
12. Bernal-Lugo and Leopold, Plant Physiol., 98:1207 (1992).
13. Bevan et al., Nature, 304:184 (1983).
14. Bevan et al., Nucl. Acids Res., 11:369 (1983).
15. Bevan, Nucl. Acids Res., 12:8711 (1984).
16. Blackman et al., Plant Physiol., 100:225 (1992).
17. Blochlinger & Diggelmann, Mol Cell Biol, 4:2929 (1984).
18. Bol et al., Ann. Rev. Phytopath., 28:113 (1990).
19. Bouchez et al., EMBO J., 8:4197 (1989).
20. Bourouis et al., EMBO J., 2:1099 (1983).
21. Bowler et al., Ann. Rev. Plant Physiol., 43:83 (1992).
22. Branson and Guss, Proc. North Central Branch Entomological Society of America (1972).
23. Broakgert et al., Science, 245:110 (1989).
24. Bustos M M et al. (1989) Plant Gell 1:839-853
25. Byrne et al. Plant Cell Tissue and Organ Culture, 8:3 (1987).
26. Callis et al., Genes and Develop., 1:1183 (1987).
27. Campbell and Gowri, Plant Physiol., 92:1 (1990).
28. Campbell, W. C., ed. Ivermectin and Abamectin, Springer-Verlag, New York, 1989.
29. Chee et al. Plant Physiol., 91:1212 (1989).
30. Chen and Winans (1991) J. Bacteriol. 173: 1139-1144
31. Christou et al. Proc. Natl. Acad. Sci USA, 86:7500 (1989).
32. Christou et al., Biotechnology, 9:957 (1991).
33. Christou et al., Plant Physiol., 87:671 (1988).
34. Chui et al. (1996) Curr Biol 6:325-330
35. Coe et al., In: Corn and Corn Improvement, Sprague et al. (eds.) pp. 81-258 (1988).
36. Corpet et al. Nucleic Acids Res., 16:10881 (1988).
37. Coxson et al., Biotropica, 24:121 (1992).
38. Crameri et al., Nature Biotech., 15:436 (1997).
39. Crameri et al., Nature, 391:288 (1998).
40. Crossway et al., BioTechniques, 4:320 (1986).
41. Cuozzo et al., Bio/Technology, 6:549 (1988).
42. Cutler et al., J. Plant Physiol., 135:351 (1989).
43. Czapla and Lang, J. Econ. Entomol., 83:2480 (1990).
44. Datta et al., Bio/Technology, 8:736 (1990).
45. Davies et al., Plant Physiol., 93:588 (1990).
46. Dayhoff et al., Atlas of Protein Sequence and Structure, Natl. Biomed. Res. Found., Washington, C. D. (1978).
47. De Blaere et al., Meth. Enzymol., 143:277 (1987).
48. De Block et al. Plant Physiol., 91:694 (1989).
49. De Block et al., EMBO Journal, 6:2513 (1987).

50. Deblaere et al. Nucl Acids Res 13:4777-4788 (1985)
51. Della-Cioppa et al. Bio/Technology 5:579-584 (1987)
52. Della-Cioppa et al., Plant Physiology, 84:965-968 (1987).
53. Dellaporta et al., in Chromosome Structure and Function, Plenum Press, 263-282 (1988).
54. Depicker et al., Plant Cell Reports, 7:63 (1988).
55. Dunn et al., Can. J. Plant Sci., 61:583 (1981).
56. Dure et al., Plant Mol. Biol., 12:475 (1989).
57. Ebinuma et al. Proc Natl Acad Sci USA 94:2117-2121 (2000a)
58. Ebinuma et al. Selection of Marker-free transgenic plants using the oncogenes (ipt, rol A, B, C) of *Agrobacterium* as selectable markers, In Molecular Biology of Woody Plants. Kluwer Academic Publishers (2000b)
59. Eichholtz et al. Somatic Cell and Molecular Genetics 13, 67-76 (1987)
60. Ellis et al., EMBO Journal, 6:3203 (1987).
61. Elroy-Stein et al., Proc. Natl. Acad. Sci. U.S.A., 86:6126 (1989).
62. English et al., Plant Cell, 8:179 (1996).
63. Erdmann et al., J. Gen. Microbiol., 138:363 (1992).
64. Erikson et al. Nat Biotechnol. 22(4):455-8 (2004)
65. Everett et al., Bio/Technology, 5:1201(1987).
66. Fedoroff N V & Smith D L Plant J 3:273-289 (1993)
67. Fire A et al Nature 391:806-811 (1998)
68. Fitzpatrick, Gen. Engineering News, 22:7 (1993).
69. Fraley et al. Proc Natl Acad Sci USA 80:4803 (1983)
70. Fromm et al., Bio/Technology, 8:833 (1990).
71. Fromm et al., Nature (London), 319:791 (1986).
72. Galbiati et al. Funct. Integr Genozides 2000, 20 1:25-34
73. Gallie et al. Nucl Acids Res 15:8693-8711 (1987)
74. Gallie et al., Nucleic Acids Res., 15:3257 (1987).
75. Gallie et al., The Plant Cell, 1:301 (1989).
76. Gan et al., Science, 270:1986 (1995).
77. Gatehouse et al., J. Sci. Food Agric., 35:373 (1984).
78. Gelfand, eds., PCR Strategies Academic Press, New York (1995).
79. Gelvin et al., Plant Molecular Biology Manual, (1990).
80. Gleave et al. Plant Mol Biol. 40(2):223-35 (1999)
81. Gordon-Kamm et al., Plant Cell, 2:603 (1990).
82. Goring et al, PNAS, 88:1770 (1991).
83. Gruber, et al., Vectors for Plant Transformation, in: Methods in Plant Molecular Biology & Biotechnology" in Glich et al., (Eds. pp. 89-119, CRC Press, 1993).
84. Guerineau et al., Mol. Gen. Genet., 262:141 (1991).
85. Guerrero et al., Plant Mol. Biol., 15:11 (1990).
86. Gupta et al., PNAS, 90:1629 (1993).
87. Haines and Higgins (eds.), Nucleic Acid Hybridization, IRL Press, Oxford, U.K.
88. Hajdukiewicz et al. Plant Mol Biol 25:989-994 (1994)
89. Hammock et al., Nature, 344:458 (1990).
90. Hansen et al. Proc. Natl. Acad. Sci. USA 91:7603-7607 (1994)
91. Hayford et al. Plant Physiol. 86:1216 (1988)
92. Hemenway et al., EMBO Journal, 7:1273 (1988).
93. Henikoff & Henikoff, Proc. Natl. Acad. Sci. USA, 89:10915 (1989).
94. Hiei et al. Plant J 6: 271-282 (1994)
95. Higgins et al., Gene, 73:237 (1988).
96. Higo et al. (1999) Nucl Acids Res 27(1): 297-300
97. Hilder et al., Nature, 330:160 (1987).
98. Hille et al. Plant Mol. Biol. 7:171 (1986)
99. Hinchee et al. Bio/Technology 6:915 (1988).
100. Hoekema et al. (1983) Nature 303:179-181
101. Hoekema, In: The Binary Plant Vector System. Offsetdrukkerij Kanters B. V.; Alblasserdam (1985).
102. Hood et al. J Bacteriol 168:1291-1301 (1986)
103. Huang et al., CABIOS, 8:155 (1992).
104. Ikeda et al., J. Bacteriol., 169:5612 (1987).
105. Ikuta et al., Biotech., 8:241 (1990).
106. Ingelbrecht et al., Plant Cell, 1:671 (1989).
107. Innis and Gelfand, eds., PCR Methods Manual (Academic Press, New York) (1999).
108. Innis et al., eds., PCR Protocols: A Guide to Methods and Applications (Academic Press, New York (1995).
109. Innis et al., PCR Protocols: A Guide to Methods and Applications, Academic Press, Inc., San Diego, Calif. (1990).
110. Ishida Y et al. Nature Biotech 745-750 (1996)
111. Jefferson et al. EMBO J 6:3901-3907 (1987)
112. Jefferson et al. Plant Mol Biol Rep 5:387-405 (1987)
113. Jenes B et al. Techniques for Gene Transfer, in: Recombinant Plants, Vol. 1, Engineering and Utilization, edited by S D Kung and R Wu, Academic Press, pp. 128-143 (1993)
114. Jobling et al., Nature, 325:622 (1987).
115. Johnson et al., PNAS USA, 86:9871 (1989)
116. Jones et al. Mol. Gen. Genet., 210:86 (1987)
117. Joshi et al., Nucleic Acid Res., 15:9627 (1987).
118. Kaasen et al., J. Bacteriol., 174:889 (1992).
119. Karlin and Altschul, Proc. Natl. Acad Sci. USA, 87:2264 (1990).
120. Karlin and Altschul, Proc. Natl. Acad. Sci. USA, 90:5873 (1993).
121. Karsten et al., Botanica Marina, 35:11 (1992).
122. Katz et al., J. Gen. Microbiol., 129:2703 (1983).
123. Keller et al., EMBO Journal, 8:1309 (1989).
124. Keller et al., Genes Dev., 3:1639 (1989).
125. Klapwijk et al. J. Bacteriol., 141,128-136 (1980)
126. Klein et al., Bio/Technoloy, 6:559 (1988).
127. Klein et al., Plant Physiol., 91:440 (1988).
128. Klein et al., Proc. Natl. Acad. Sci. USA, 85:4305 (1988).
129. Knauf, et al., Genetic Analysis of Host Range Expression by *Agrobacterium* In: Molecular Genetics of the Bacteria-Plant Interaction, Puhler, A. ed., Springer-Verlag, New York, 1983.
130. Koncz & Schell Mol Gen Genet 204:383-396 (1986)
131. Koprek T et al. Plant J 19(6): 719-726 (1999)
132. Koster and Leopold, Plant Physiol., 88:829 (1988).
133. Koziel et al., Biotechnology, 11:194 (1993).
134. Kunkel et al., Methods in Enzymol., 154:367 (1987).
135. Kunkel, Proc. Natl. Acad. Sci. USA, 82:488 (1985).
136. Lam E und Chua N H, J Biol Chem; 266(26):17131-17135 (1991)
137. Laufs et al., PNAS, 87:7752 (1990).
138. Lawton et al., Mol. Cell Biol., 7:335 (1987).
139. Lee and Saier, J. Bacteriol., 153 (1982).
140. Leffel et al. Biotechniques 23(5):912-8 (1997)
141. Lescot et al. Nucleic Acids Res 30(1):325-7 (2002)
142. Li et al. Plant Mol Biol 20:1037-1048 (1992)
143. Lindsey et al., Transgenic Research, 2:3347 (1993).
144. Liu et al., Plant J. 8, 457-463 (1995)
145. Lommel et al., Virology, 181:382 (1991).
146. Loomis et al., J. Expt. Zool., 252:9 (1989).
147. Lorz et al., Mol. Gen. Genet., 199:178 (1985).
148. Ma et al., Nature, 334 :631 (1988).
149. Macejak et al., Nature, 353:90 (1991).
150. Maki et al., Methods in Plant Mol Biol & Biotechnol, Glich et al., 67-88 CRC Press, (1993).
151. Maniatis T, Fritsch E F, and Sambrook J Molecular Cloning: A Laboratory Manual, Cold Spring Harbor Laboratory, Cold Spring Harbor (N.Y.), (1989)

152. Matzke et al. (2000) Plant Mol Biol 43:401-415;
153. Matsuoka M et al. (2001) High-level expression of C4 photosynthetic genes in transgenic rice. In: Rice genetics IV. Proceedings of the Fourth International Rice Genetics Symposium, Los Banos, Philippines, 22-27.10. 2000. eds. Khush; Brar; Hardy pp. 439-447
154. McBride et al., PNAS USA, 91:7301 (1994).
155. McCabe et al., Bio/Technology, 6:923 (1988).
156. Meinkoth and Wahl, Anal. Biochem., 138:267 (1984).
157. Messing and Vierra, Gene, 19:259 (1982).
158. Michael et al., J. Mol. Biol., 26 :585 (1990). (im Text steht: Michael et al. 1994)
159. Millar et al. Plant Mol Biol Rep 10:324-414 (1992)
160. Mogen et al., Plant Cell, 2:1261 (1990).
161. Moore et al., J. Mol. Biol., 272:336 (1997).
162. Mozo & Hooykaas Plant Mol. Biol. 16:917-918 (1991)
163. Mundy and Chua, EMBO J., 7:2279 (1988).
164. Munroe et al., Gene, 91:151 (1990).
165. Murakami et al., Mol. Gen. Genet., 205:42 (1986).
166. Murata et al., FEBS Lett., 296:187 (1992).
167. Murdock et al., Phytochemistry, 29:85 (1990).
168. Murray et al., Nucleic Acids Res., 17:477 (1989).
169. Myers and Miller, CABIOS, 4:11 (1988).
170. Naested H Plant J 18:571-576 (1999)
171. Napoli et al., Plant Cell, 2:279 (1990).
172. Needleman and Wunsch, J. Mol. Biol., 48:443-453 (1970).
173. Nehra et al. Plant J. 5:285-297 (1994)
174. Niedz et al., Plant Cell Reports, 14:403 (1995).
175. Odell et al., Mol. Gen. Genet., 113:369 (1990).
176. Odell et al., Nature, 313:810 (1985).
177. Ohtsuka et al., J. Biol. Chem., 260:2605 (1985)
178. Olhoft et al. Plant Cell Rep 20: 706-711 (2001)
179. Ow et al., Science, 234:856 (1986).
180. Pacciotti et al., Bio/Technology, 3:241 (1985).
181. Park et al., J. Plant Biol., 38:365 (1985).
182. Paszkowski et al., EMBO J., 3:2717 (1984).
183. Pearson and Lipman, Proc. Natl. Acad. Sci., 85:2444 (1988).
184. Pearson et al., Meth. Mol. Biol., 24:307 (1994).
185. Perera R J et al. Plant Mol. Biol 23(4): 793-799 (1993)
186. Perlak et al., Proc. Natl. Acad. Sci. USA, 88:3324 (1991).
187. Phillips et al., In Corn & Corn Improvement, 3rd Edition 10, Sprague et al. (Eds.) pp. 345-387 (1988).
188. Phi-Van et al., Mol. Cell. Biol., 10:2302 (1990).
189. Piatkowski et al., Plant Physiol., 94:1682 (1990).
190. Potrykus et al., Mol. Gen. Genet., 199:183 (1985).
191. Potrykus, Trends Biotech., 7:269 (1989).
192. Prasher et al., Biochem. Biophys. Res. Comm., 126: 1259 (1985).
193. Proudfoot, Cell, 64:671 (1991).
194. Reed et al., J. Gen. Microbiol., 130:1 (1984).
195. Riggs et al., Proc. Natl. Acad. Sci. USA, 83:5602 (1986).
196. Rossolini et al., Mol. Cell. Probes, 8:91 (1994).
197. Ruiz, Plant Cell, 10:937 (1998).
198. Sambrook et al., Molecular Cloning: A Laboratory Manual (2d ed., Cold Spring Harbor Laboratory Press, Plainview, N.Y.) (1989).
199. Sanfacon et al., Genes Dev., 5:141 (1991).
200. Sanford et al., Particulate Science and Technology, 5:27 (1987).
201. Scheeren-Groot et al. J. Bacteriol 176: 6418-6426 (1994)
202. Schenborn and Groskreutz Mol Biotechnol 13(1): 29-44 (1999).
203. SchIaman and Hooykaas Plant J 11:1377-1385 (1997)
204. Schoffl F et al. (1989) Mol Gen Genetics 217(2-3): 246-53

205. Shagan et al., Plant Physiol., 101:1397 (1993).
206. Shah et al. Science 233: 478 (1986)
207. Shapiro, Mobile Genetic Elements, Academic Press, N.Y. (1983).
208. Shimamoto et al., Nature, 338:274 (1989).
209. Silhavy T J, Berman M L, and Enquist L W Experiments with Gene Fusions, Cold Spring Harbor Laboratory Press, Cold Spring Harbor (N.Y.), (1984)
210. Skuzeski et al., Plant Molec. Biol. 15: 65-79 (1990).
211. Smith et al., Adv. Appl. Math., 2:482.(1981).
212. Smith et al., Mol. Gen. Genet., 224:447 (1990).
213. Spencer et al., Theor. Appl. Genet, 79:625 (1990). Spencer 1992 Referenz fehlt
214. Stalker et al., Science, 242:419 (1988).
215. Staub et al., EMBO J., 12:601 (1993).
216. Staub et al., Plant Cell, 4:39 (1992).
217. Steifel et al., The Plant Cell, 2:785 (1990).
218. Stemmer, Nature, 370:389 (1994).
219. Stemmer, Proc. Natl. Acad. Sci. USA, 91:10747 (1994).
220. Stief et al., Nature, 341:343 (1989).
221. Stougaard Plant J 3:755-761 (1993)
222. Sukhapinda et al., Plant Mol. Biol., 8:209 (1987).
223. Sundaresan et al. Gene Develop 9: 1797-1810 (1995)
224. Sutcliffe, PNAS USA, 75:3737 (1978).
225. Svab et al., Plant Mol. Biol. 14:197 (1990)
226. Svab et al., Proc. Natl. Acad. Sci. USA, 87:8526 (1990).
227. Svab et al., Proc. Natl. Acad. Sci. USA, 90:913 (1993).
228. Tarczynski et al., PNAS USA, 89:2600 (1992).
229. Thillet et al., J. Biol. Chem., 263:12500 (1988).
230. Tijssen, Laboratory Techniques in Biochemistry and Molecular Biology-Hybridization with Nucleic Acid Probes, Elsevier, N.Y. (1993).
231. Tomes et al., Plant Cell, Tissue and Organ Culture: Fundamental Methods, Springer Verlag, Berlin (1995).
232. Tomic et al., NAR, 12:1656 (1990).
233. Turner et al., Molecular Biotechnology, 3:225 (1995).
234. Twell et al., Plant Physiol., 91:1270 (1989).
235. Ugaki et al., Nucl. Acids Res., 19:371 (1991).
236. Ulmasov et al., Plant Mol. Biol., 35:417 (1997).
237. Upender et al., Biotechniques, 18:29 (1995).
238. van der Krol et al., Plant Cell, 2:291 (1990).
239. Vanden Elzen et al. Plant Mol Biol. 5:299 (1985)
240. Vasil et al. Bio/Technology, 10:667-674 (1992)
241. Vasil et al. Bio/Technology, 11:1153-1158 (1993)
242. Vasil et al., Mol. Microbiol., 3:371 (1989).
243. Vasil et al., Plant Physiol., 91:1575 (1989).
244. Vernon and Bohnert, EMBO J., 11:2077 (1992).
245. Walker and Gaastra, eds., Techniques in Molecular Biology, MacMillan Publishing Company, New York (1983).
246. Wan & Lemaux (1994) Plant Physiol., 104:3748
247. Wang et al., Mol. Cell. Biol., 12:3399 (1992).
248. Waterman, M. S. Introduction to Computational Biology: Maps, sequences and genomes. Chapman & Hall. London (1995).
249. Watrud et al., in Engineered Organisms and the Environment (1985).
250. Watson et al. J. Bacteriol 123, 255-264 (1975)
251. Watson et al., Corn: Chemistry and Technology (1987).
252. Weeks et al. Plant Physiol 102:1077-1084 (1993)
253. Weissinger et al., Annual Rev. Genet., 22:421 (1988).
254. White et al, Nucl Acids Res, 18, 1062 (1990).
255. Wingender E et al. Nucleic Acids Res 29(1):281-3 (2001)

260. Zukowsky et al., PNAS USA, 80:1101 (1983).
256. Wolter et al., EMBO Journal, 11:4685 (1992).
257. Wyn-Jones and Storey, Physiology and Biochemistry of Drought Resistance in Plants, Paleg et al. (eds.), pp. 171-204 (1981).
258. Yamaguchi-Shinozaki et al., Plant Cell Physiol., 33:217 (1992).
259. Zhang et al., Proc. Natl. Acad. Sci. USA, 94:4504 (1997).
260. Zukowsky et al., PNAS USA, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An expression cassette for regulating meristem-preferential or meristem-specific expression in a plant comprising:
   i) at least one transcription regulating nucleotide sequence of a plant gene; and
   ii) at least one nucleic acid sequence which is operably linked to and heterologous in relation to said transcription regulating nucleotide sequence;
wherein the plant gene comprises the nucleic acid sequence as set forth in SEQ ID NO: 22 and wherein the transcription regulating nucleotide sequence has meristem-preferential or meristem-specific expression activity.

2. An expression cassette for regulating meristem-preferential or meristem-specific expression in a plant comprising:
   i) at least one transcription regulating nucleotide sequence; and
   ii) at least one nucleic acid sequence which is operably linked to and heterologous in relation to said transcription regulating nucleotide sequence;
wherein the transcription regulating nucleotide sequence comprises the nucleotide sequence of SEQ ID NO: 20 or 21, and wherein the transcription regulating nucleotide sequence has meristem-preferential or meristem-specific expression activity.

3. An expression cassette for regulating meristem-preferential or meristem-specific expression in a plant comprising:
   i) at least one transcription regulating nucleotide sequence; and
   ii) at least one nucleic acid sequence which is operably linked to and herterologous in relation to said transcription regulating nucleotide sequence;
wherein the transcription regulating nucleotide sequence comprises a fragment of SEQ ID NO: 20 or 21 and wherein the fragment has meristem-preferential or meristem-specific expression activity.

4. The expression cassette of claim 1, wherein expression of the nucleic acid sequence results in expression of a protein, or expression of an antisense RNA, a sense RNA, or a double-stranded RNA.

5. The expression cassette of claim 1, wherein expression of the at least one nucleic acid sequence in ii) confers to the plant an agronomically valuable trait.

6. A transgenic plant cell or microorganism comprising the expression cassette of claim 1.

7. A method for producing a transgenic plant cell, which comprises transforming a plant cell with the expression cassette of claim 1.

8. A method for producing a trausgenic plant, which comprises transforming a plant cell with the expression cassette of claim 1, and generating from the plant cell the transgenic plant.

9. The expression cassette of claim 2, wherein expression of the nucleic acid sequence results in expression of a protein, or expression of an antisense RNA, a sense RNA, or a double-stranded RNA.

10. The expression cassette of claim 2, wherein expression of the at least one nucleic acid sequence in ii) confers to the plant an agronomically valuable trait.

11. A transgenic plant cell or microorganism comprising the expression cassette of claim 2.

12. A method for producing a transgenic plant cell, which comprises transforming a plant cell with the expression cassette of claim 2.

13. A method for producing a transgenic plant, which comprises transforming a plant cell with the expression cassette of claim 2, and generating from the plant cell the trausgenic plant.

14. The expression cassette of claim 3, wherein expression of the nucleic acid sequence results in expression of a protein, or expression of an antisense RNA, a sense RNA, or a double-stranded RNA.

15. The expression cassette of claim 3, wherein expression of the at least one nucleic acid sequence in ii) confers to the plant an agronomically valuable trait.

16. A transgenic plant cell or microorganism comprising the expression cassette of claim 3.

17. A method for producing a transgenic plant cell, which comprises transforming a plant cell with the expression cassette of claim 3.

18. A method for producing a transgenic plant, which comprises transforming a plant cell with the expression cassette of claim 3, and generating from the plant cell the transgenic plant.

* * * * *

UNITED STATES PATENT AND TRADEMARK OFFICE
CERTIFICATE OF CORRECTION

PATENT NO. : 7,345,216 B2  
APPLICATION NO. : 11/297315  
DATED : March 18, 2008  
INVENTOR(S) : Ulrich Keetman et al.

It is certified that error appears in the above-identified patent and that said Letters Patent is hereby corrected as shown below:

In the Claims:

In Claim 8, in column 180, on line 20, "8. A method for producing a trausgenic plant, which" should read -- 8. A method for producing a transgenic plant, which --.

In Claim 13, in column 180, on line 40, "trausgenic plant." should read -- transgenic plant. --.

Signed and Sealed this

Fourteenth Day of October, 2008

JON W. DUDAS  
*Director of the United States Patent and Trademark Office*

SEQUENCE LISTING

```
<160> NUMBER OF SEQ ID NOS: 60

<210> SEQ ID NO 1
<211> LENGTH: 1630
<212> TYPE: DNA
<213> ORGANISM: Arabidopsis thaliana
<220> FEATURE:
<221> NAME/KEY: promoter
<222> LOCATION: (1)..(1630)
<223> OTHER INFORMATION: transcription regulating sequence from
      Arabidopsis thaliana gene At2g02180

<400> SEQUENCE: 1
tattgaaata aaatcagttg atttcgttgg tcttttctag gaattcagga tagatcactc      60
ttgaacacat taaggctgca atgattgaca tttttagagca agatgaaaaa gttgaaaata    120
caggtttgaa gtggatattt ttaaaaatgt attatacgta atgaatgtat tttgtttcca    180
aaacatatag ttgaatgatt gaaaatgttt gagctgaaca ttattcaact cattcctctg    240
caaaatagta gatgaaagga ttgaatagtt ttcctttaca gtttgttcat ttttttcatta   300 ttttggttga atgagttgaa tcaattttc aacatattca tttaaatggt aaaaagtgag     360
atgaatagtc atttaacatt ttcaacctt tattttaata caaccatttt cataataaat    420
taaataaaat cgtaattcag ctggaaattg ttcctccaca aaataagaga agaacgaatg    480
aataacaatt attcattgtg tccaaattat tcattttgat ttactaatcc attttgagaa    540
catttcgacc atatcatttt gatcatacca aatccacaaa tcagctctat ccattgctga    600
tttttaagaa tatgtattgc tattaatcat agttgttttg aaaataagat ggatatcatt    660
ttgtataaga tatatacgta aattcatatt gctatcaatc atagtttagt gtgtatattg    720
attagttgat tcttgtaagc tagattcttt atgattgaaa gccatatata aactcttaga    780
agaccattaa tgatgcatgg cagagttaaa caaaaaacaa taattttct taagaaaaac     840 atagtgtttt ttattgccac agttattaat gtagtggtat agtttagtat ggtggagatt    900
caatcacatt tacactaaat aatccagatg agattgtgaa tttgtgatat aatcaatgat    960
ccaattttaa agattggaga tttcttccct catggaatga ataagtccac aagagacata   1020
agaatatctt gcctataaga aagtatatat cacttacaaa caaaaaaatg aaaggaaaac   1080
agttgaattt atcatatttt gagtgcttca accataattg cattttgatg atagatactg   1140
atatagtcac acgtctttgg cacattgaca ccaataacat cagggagaac gttagaccat   1200
ctccaatggt taagaactaa ttgattctta actttgcatt taaattaaaa ttttaaaaca   1260
tgacatatta tagttttttt cttatgaaaa catcttagct aagaaataaa tcttattttc   1320
taagcagttt tgatttattt ttcagagttt aattctaaaa tattagttta agatatacaa   1380
cctaagatat atcaatggaa gtaaaaaagg taagtttgaa ccgagcaata acttttctaa   1440
```

-continued

| | |
|---|---|
| ccgttgtgaa ttatttaatt agaaactccc cataattagc aaacggtaac ttttctaacc | 1500 |
| gttatgaatt attatttatt tcattcgaaa ctccccaaaa ttagcaaaca gtaacttttg | 1560 |
| taaaatataa tattttaccc gaacctgtaa cttattcgac cgttagaagt aatctctata | 1620 |
| tatacacctt | 1630 |

<210> SEQ ID NO 2
<211> LENGTH: 1631
<212> TYPE: DNA
<213> ORGANISM: Arabidopsis thaliana
<220> FEATURE:
<221> NAME/KEY: promoter
<222> LOCATION: (1)..(1631)
<223> OTHER INFORMATION: transcription regulating sequence from
    Arabidopsis thaliana gene At2g02180

<400> SEQUENCE: 2

| | |
|---|---|
| tattgaaata aaatcagttg atttcgttgg tcttttctag gaattcagga tagatcactc | 60 |
| ttgaacacat taaggctgca atgattgaca ttttagagca agatgaaaaa gttgaaaata | 120 |
| caggtttgaa gtggatattt ttaaaaaatg tattatacgt aatgaatgta ttttgtttcc | 180 |
| aaaacatata gttgaatgat tgaaaatgtt tgagctgaac attattcaac tcattcctct | 240 |
| gcaaaatagt agatgaaagg attgaatagt tttcctttac agtttgttca ttttttcatt | 300 |
| attttggttg aatgagttga atcaattttt caacatattc atttaaatgg taaaaagtga | 360 |
| gatgaatagt catttaacat tttcaacctt ttattttaat acaaccattt tcataataaa | 420 |
| ttaaataaaa tcgtaattca gctggaaatt gttcctccac aaaataagag aagaacgaat | 480 |
| gaataaaaat tattcattgt gtccaaatta ttcattttga tttactaatc cattttgaga | 540 |
| acatttcgac catatcattt tgatcatacc aaatccacaa atcagctcta tccattgctg | 600 |
| atttttaaga atatgtattg ctattaatca tagttgtttt gaaataagag tggatatcat | 660 |
| tttgtataag atatatacgt aaattcatat tgctatcaat catagtttag tgtgtatatt | 720 |
| gattagttga ttcttgtaaa ctagattctt tatgattgaa agccatatat aaactcttag | 780 |
| aagaccatta atgatgcatg gcagagttaa acaaaaaaca ataattttc ttaagaaaaa | 840 |
| catagtgttt tttattgcca cagttattaa tgtagtggta tagtttagta tggtggagat | 900 |
| tcaatcacat ttacactaaa taatccagat gagattgtga atttgtgata taatcaatga | 960 |
| tccaattta aagattggag atttcttccc tcatggaatg aataagtcca caagagacat | 1020 |
| aagaatatct tgcctataag aaagtatata tcacttacaa acaaaaaaat gaaggaaaa | 1080 |
| cagttgaatt tatcatattt tgagtgcttc aaccataatt gcattttgat gatagatact | 1140 |
| gatatagtca cacgtctttg gcacattgac accaataaca tcagggagaa cgttagacca | 1200 |
| tctccaatgg ttaagaacta attgattctt aactttgcat ttaaattaaa attttaaaac | 1260 |
| atgacatatt atagtttttt tcttatgaaa acatcttagc taagaaataa atcttatttt | 1320 |
| ctaagcagtt ttgatttatt tttcagagtt taattctaaa atattagttt aagatataca | 1380 |
| acctaagata tatcaatgga agtaaaaaag gtaagtttga accgagcaat aactttctta | 1440 |
| accgttgtga attatttaat tagaaactcc ccataattag caaacggtaa cttttctaac | 1500 |
| cgttatgaat tattatttat ttcattcgaa actccccaaa attagcaaac agtaacttt | 1560 |
| gtaaaatata atattttacc cgaacctgta acttattcga ccgttagaag taatctctat | 1620 |
| atatacacct t | 1631 |

<210> SEQ ID NO 3

```
<211> LENGTH: 1200
<212> TYPE: DNA
<213> ORGANISM: Arabidopsis thaliana
<220> FEATURE:
<221> NAME/KEY: promoter
<222> LOCATION: (1)..(1200)
<223> OTHER INFORMATION: transcription regulating sequence from
      Arabidopsis thaliana gene At2g02180

<400> SEQUENCE: 3
gcctccatag gatgctcatg ctgtctttga aggcccataa gtaaggccat gcctatttga      60
cggtcaaaga caaaaatggt tccatttgac caagaagatg atcatatagt attatgacag     120
ctattgtact ccccaatcca acacagcaac acacgaatgc ctagtcggtg attcatcatg     180
aagattaatt cctacataat tagtattatc ttctaacaat tctcattttt caaagattca     240
agcctgcagc tccaaagtga gaatcacgga ttgtacttaa atcgagtgcg aatatagctg     300
atgtttagaa ttttggaaa atttctacgt ttcgtagata taattttttg ggattactag      360
caaaacccaa acctccaaaa attcttaatc tcgaattaat tatatttttt ttatcgtcga     420
tttattattt attacaaatt atataaactg ttatatagtc gattatacta cgaacaattc     480
cttccaaccg ttattagatc tacgacagcc gccaccacct tttcttttttt catgcttttg     540
atggacattt tttcaacaat tttttttgcg tagaatccta acaagcagtt ataattgtac     600
atcgttggaa atctcttaca tacttacttc cattaatctg caaatcagct aataaatttc     660
tatcgtcgaa gcttttttgta ggtatacgtt tttttatttc tctcactta aaaataaaaa     720
ccaaaaaaat tttttatgca aaaacaaaat gatctctat gaggactctt gtatgttggg      780
cctggccctg aagatatcta ttgtaagaaa gatcaattaa aaaagtaaaa attaccataa     840
ctgtcattct ctaatcataa tagcttactt tgcttcactt gattaggcat aatatttgaa     900
ttctctttgt gtggatcaag ccagctttgg tttgctcttt atccacatgt gccacgtgga     960
gcagcgtgtc agtcaactttt caacaactac ttgactctcc cgacgataat taccggctat    1020
ctccggttct cgtttccgac gtcggccgtt tcttttttcat ttttgtcgtt ttttttccaa    1080
attttttat ttcgggaaaa taacaaaaaa agaaagaat aaaaagaggt gattcaaatc      1140
cagagagttc tcattatgta tattcaaaat ctgaatcgag aaggaatctg actcgtgtag    1200

<210> SEQ ID NO 4
<211> LENGTH: 1296
<212> TYPE: DNA
<213> ORGANISM: Arabidopsis thaliana
<220> FEATURE:
<221> NAME/KEY: CDS
<222> LOCATION: (113)..(1024)
<223> OTHER INFORMATION: coding for tobamovirus multiplication protein 3
      (TOM3)

<400> SEQUENCE: 4
atttcgggaa aataacaaaa aaagaaagaa ataaaaagag gtgattcaaa tccagagagt      60
tctcattatg tatattcaaa atctgaatcg agaaggaatc tgactcgtgt ag atg aga     118
                                                             Met Arg
                                                               1 atc ggc ggc gtc gag gtt acg aaa ttt gcg tcg gag atg atg tcg tcg      166
Ile Gly Gly Val Glu Val Thr Lys Phe Ala Ser Glu Met Met Ser Ser
        5                  10                  15 tcg tct tcg tcg gcg gtg gag atg ttg aat ctc aaa gaa gct tcg aat      214
Ser Ser Ser Ser Ala Val Glu Met Leu Asn Leu Lys Glu Ala Ser Asn
     20                  25                  30 tgg tgg tca gac gta aac gaa tct ccg att tgg cag gat cgt atc ttc      262
```

-continued

| | | | | | | | | | | | | | | | | |
|---|---|---|---|---|---|---|---|---|---|---|---|---|---|---|---|---|
| Trp | Trp | Ser | Asp | Val | Asn | Glu | Ser | Pro | Ile | Trp | Gln | Asp | Arg | Ile | Phe | |
| 35 | | | | 40 | | | | | 45 | | | | | 50 | | |

| cat | gtt | ctc | gct | gtt | ctc | tac | gga | atc | gtt | tcc | ctc | gtt | gct | gtg | att | 310 |
|---|---|---|---|---|---|---|---|---|---|---|---|---|---|---|---|---|
| His | Val | Leu | Ala | Val | Leu | Tyr | Gly | Ile | Val | Ser | Leu | Val | Ala | Val | Ile | |
| | | | | 55 | | | | | 60 | | | | | 65 | | |

| caa | ctt | gtg | aga | ata | caa | ttg | aga | gtt | cct | gaa | tat | ggt | tgg | acg | acg | 358 |
|---|---|---|---|---|---|---|---|---|---|---|---|---|---|---|---|---|
| Gln | Leu | Val | Arg | Ile | Gln | Leu | Arg | Val | Pro | Glu | Tyr | Gly | Trp | Thr | Thr | |
| | | | 70 | | | | | 75 | | | | | 80 | | | |

| caa | aag | gtc | ttt | cac | ttt | ctc | aat | ttc | gtt | gtt | aat | gga | gtt | cgt | gct | 406 |
|---|---|---|---|---|---|---|---|---|---|---|---|---|---|---|---|---|
| Gln | Lys | Val | Phe | His | Phe | Leu | Asn | Phe | Val | Val | Asn | Gly | Val | Arg | Ala | |
| | | 85 | | | | | 90 | | | | | 95 | | | | |

| gtg | gtg | ttt | gtc | ttc | agg | cga | aat | gtt | cag | ttt | atg | caa | cca | gag | att | 454 |
|---|---|---|---|---|---|---|---|---|---|---|---|---|---|---|---|---|
| Val | Val | Phe | Val | Phe | Arg | Arg | Asn | Val | Gln | Phe | Met | Gln | Pro | Glu | Ile | |
| | 100 | | | | 105 | | | | | 110 | | | | | | |

| ctg | caa | cat | atc | ttg | ctt | gat | att | cca | agt | ctt | gct | ttc | ttc | acc | acc | 502 |
|---|---|---|---|---|---|---|---|---|---|---|---|---|---|---|---|---|
| Leu | Gln | His | Ile | Leu | Leu | Asp | Ile | Pro | Ser | Leu | Ala | Phe | Phe | Thr | Thr | |
| 115 | | | | 120 | | | | | 125 | | | | | 130 | | |

| tat | gct | ctt | ctg | gtt | ctt | ttc | tgg | gct | gaa | att | tat | tat | cag | gcg | cgt | 550 |
|---|---|---|---|---|---|---|---|---|---|---|---|---|---|---|---|---|
| Tyr | Ala | Leu | Leu | Val | Leu | Phe | Trp | Ala | Glu | Ile | Tyr | Tyr | Gln | Ala | Arg | |
| | | | 135 | | | | | 140 | | | | | 145 | | | |

| gca | gta | tcg | act | gat | gga | ctc | agg | cca | agc | ttc | ttc | aca | att | aat | gca | 598 |
|---|---|---|---|---|---|---|---|---|---|---|---|---|---|---|---|---|
| Ala | Val | Ser | Thr | Asp | Gly | Leu | Arg | Pro | Ser | Phe | Phe | Thr | Ile | Asn | Ala | |
| | | | 150 | | | | | 155 | | | | | 160 | | | |

| gtt | gta | tat | gta | gtt | cag | att | gct | cta | tgg | ttg | gtt | ttg | tgg | tgg | aag | 646 |
|---|---|---|---|---|---|---|---|---|---|---|---|---|---|---|---|---|
| Val | Val | Tyr | Val | Val | Gln | Ile | Ala | Leu | Trp | Leu | Val | Leu | Trp | Trp | Lys | |
| | | 165 | | | | | 170 | | | | | 175 | | | | |

| cct | gtt | cga | gtt | atg | gta | atc | cta | tct | aag | atg | ttc | ttt | gca | ggt | gtt | 694 |
|---|---|---|---|---|---|---|---|---|---|---|---|---|---|---|---|---|
| Pro | Val | Arg | Val | Met | Val | Ile | Leu | Ser | Lys | Met | Phe | Phe | Ala | Gly | Val | |
| | 180 | | | | 185 | | | | | 190 | | | | | | |

| tca | ttg | ttc | gct | gcc | ctt | gga | ttt | tta | ctt | tat | ggt | gga | agg | ctt | ttc | 742 |
|---|---|---|---|---|---|---|---|---|---|---|---|---|---|---|---|---|
| Ser | Leu | Phe | Ala | Ala | Leu | Gly | Phe | Leu | Leu | Tyr | Gly | Gly | Arg | Leu | Phe | |
| 195 | | | | 200 | | | | | 205 | | | | | 210 | | |

| cta | atg | ttg | caa | cgg | ttt | cca | gta | gaa | tct | aaa | ggg | cgg | cgc | aaa | aag | 790 |
|---|---|---|---|---|---|---|---|---|---|---|---|---|---|---|---|---|
| Leu | Met | Leu | Gln | Arg | Phe | Pro | Val | Glu | Ser | Lys | Gly | Arg | Arg | Lys | Lys | |
| | | | 215 | | | | | 220 | | | | | 225 | | | |

| ctg | caa | gag | gtt | ggt | tac | gtg | aca | acc | ata | tgc | ttt | acg | tgt | ttc | ctc | 838 |
|---|---|---|---|---|---|---|---|---|---|---|---|---|---|---|---|---|
| Leu | Gln | Glu | Val | Gly | Tyr | Val | Thr | Thr | Ile | Cys | Phe | Thr | Cys | Phe | Leu | |
| | | | 230 | | | | | 235 | | | | | 240 | | | |

| atc | aga | tgt | atc | atg | atg | tgc | ttt | gct | gct | ttc | gat | gag | ggg | gca | aac | 886 |
|---|---|---|---|---|---|---|---|---|---|---|---|---|---|---|---|---|
| Ile | Arg | Cys | Ile | Met | Met | Cys | Phe | Ala | Ala | Phe | Asp | Glu | Gly | Ala | Asn | |
| | | 245 | | | | | 250 | | | | | 255 | | | | |

| ctt | gat | gtg | tta | gat | cac | ccc | atc | ctt | aac | ttc | ata | tat | tac | ctg | ttg | 934 |
|---|---|---|---|---|---|---|---|---|---|---|---|---|---|---|---|---|
| Leu | Asp | Val | Leu | Asp | His | Pro | Ile | Leu | Asn | Phe | Ile | Tyr | Tyr | Leu | Leu | |
| | 260 | | | | 265 | | | | | 270 | | | | | | |

| gta | gag | ata | tta | ccc | tcc | tct | ctg | gtc | ctc | ttc | atc | ttg | aga | aag | cta | 982 |
|---|---|---|---|---|---|---|---|---|---|---|---|---|---|---|---|---|
| Val | Glu | Ile | Leu | Pro | Ser | Ser | Leu | Val | Leu | Phe | Ile | Leu | Arg | Lys | Leu | |
| 275 | | | | 280 | | | | | 285 | | | | | 290 | | |

| cca | cca | aaa | cga | ggc | att | aca | caa | tac | cat | cag | att | cgc | tga | | | 1024 |
|---|---|---|---|---|---|---|---|---|---|---|---|---|---|---|---|---|
| Pro | Pro | Lys | Arg | Gly | Ile | Thr | Gln | Tyr | His | Gln | Ile | Arg | | | | |
| | | | 295 | | | | | 300 | | | | | | | | | aatgtaaagg cacgcaaact aatgatcaga tgaagaagac aagactatgg ttgtttatgc     1084 ttttctgtaa tcaatagaga gaaaagcata agatggaaat gaaatagatc taaagctgat     1144 aaggcctttt ggttgatgat gggaatggat tctacttgat ttttggtaaa cggtaaactg     1204 gggtttgttc cctttatata aaggttatgt tgtaaaaaat ttattataaa gtacatgtaa     1264 gaattgtgta aatttatgtt gaatcatgtg gt     1296

<210> SEQ ID NO 5

<211> LENGTH: 303
<212> TYPE: PRT
<213> ORGANISM: Arabidopsis thaliana

<400> SEQUENCE: 5

```
Met Arg Ile Gly Gly Val Glu Val Thr Lys Phe Ala Ser Glu Met Met
1               5                   10                  15

Ser Ser Ser Ser Ser Ala Val Glu Met Leu Asn Leu Lys Glu Ala
            20                  25                  30

Ser Asn Trp Trp Ser Asp Val Asn Glu Ser Pro Ile Trp Gln Asp Arg
        35                  40                  45

Ile Phe His Val Leu Ala Val Leu Tyr Gly Ile Val Ser Leu Val Ala
    50                  55                  60

Val Ile Gln Leu Val Arg Ile Gln Leu Arg Val Pro Glu Tyr Gly Trp
65                  70                  75                  80

Thr Thr Gln Lys Val Phe His Phe Leu Asn Phe Val Val Asn Gly Val
                85                  90                  95

Arg Ala Val Val Phe Val Phe Arg Arg Asn Val Gln Phe Met Gln Pro
            100                 105                 110

Glu Ile Leu Gln His Ile Leu Leu Asp Ile Pro Ser Leu Ala Phe Phe
        115                 120                 125

Thr Thr Tyr Ala Leu Leu Val Leu Phe Trp Ala Glu Ile Tyr Tyr Gln
    130                 135                 140

Ala Arg Ala Val Ser Thr Asp Gly Leu Arg Pro Ser Phe Phe Thr Ile
145                 150                 155                 160

Asn Ala Val Val Tyr Val Val Gln Ile Ala Leu Trp Leu Val Leu Trp
                165                 170                 175

Trp Lys Pro Val Arg Val Met Val Ile Leu Ser Lys Met Phe Phe Ala
            180                 185                 190

Gly Val Ser Leu Phe Ala Ala Leu Gly Phe Leu Leu Tyr Gly Gly Arg
        195                 200                 205

Leu Phe Leu Met Leu Gln Arg Phe Pro Val Glu Ser Lys Gly Arg Arg
    210                 215                 220

Lys Lys Leu Gln Glu Val Gly Tyr Val Thr Thr Ile Cys Phe Thr Cys
225                 230                 235                 240

Phe Leu Ile Arg Cys Ile Met Met Cys Phe Ala Ala Phe Asp Glu Gly
                245                 250                 255

Ala Asn Leu Asp Val Leu Asp His Pro Ile Leu Asn Phe Ile Tyr Tyr
            260                 265                 270

Leu Leu Val Glu Ile Leu Pro Ser Ser Leu Val Leu Phe Ile Leu Arg
    275                 280                 285

Lys Leu Pro Pro Lys Arg Gly Ile Thr Gln Tyr His Gln Ile Arg
    290                 295                 300
```

<210> SEQ ID NO 6
<211> LENGTH: 510
<212> TYPE: DNA
<213> ORGANISM: Arabidopsis thaliana
<220> FEATURE:
<221> NAME/KEY: promoter
<222> LOCATION: (1)..(510)
<223> OTHER INFORMATION: transcription regulating sequence from
      Arabidopsis thaliana gene At5g54510

<400> SEQUENCE: 6
atttctttaa agagaataat ttaagttaaa tcagggggta gaaaaaatta attcaaccat     60
caaatatatt ttattaacta aaataaagtg ggagaattca agaatactat atagtttgaa    120

```
tgtccttaaa ctattaaacc ttttttattca agccagtacg ggtattgacc aatatagaaa      180
acaaaattat ataaatacca cttttttgtaa tgaaacgaac taaaataaaa taaacgacat      240
tataaagtaa atcaaattaa acacgaatag taagccgttc acttaaatcc tggatttcaa      300
catactgtga aatgaccgtt atacccttttg atatcttctt caccctcttc ctctttcccc      360
ctatatatat gaactcttcc tcttccattt ttcctcacac ccttaaagct tcaacaaaac      420
cagatcaagc ttctttcacc attttcactc ttctttaagc tttctttctt aatttctctc      480
atttcgaatt ttaaacacaa aacctaacgc                                        510
```

```
<210> SEQ ID NO 7
<211> LENGTH: 511
<212> TYPE: DNA
<213> ORGANISM: Arabidopsis thaliana
<220> FEATURE:
<221> NAME/KEY: promoter
<222> LOCATION: (1)..(511)
<223> OTHER INFORMATION: transcription regulating sequence from
      Arabidopsis thaliana gene At5g54510

<400> SEQUENCE: 7
```

```
atttccttta aagagaataa tttaagttaa atcaggggt agaaaaaatt aattcaacca       60
tcaaatatat tttattaact aaaataaagt gggagaattc aagaatacta tatagtttga      120
atgtccttaa actattaaac cttttttattc aagccagtac gggtattgac caatatagaa     180
aacaaaatta tataaatacc acttttttgta atgaaacgaa ctaaaataaa ataaacgaca     240
ttataaagta aatcaaatta aacacgaata gtaagccgtt cacttaaatc ctggatttca     300
acatactgtg aaatgaccgt tataccctt gatatcttct tcaccctctt cctctttccc      360
tctatatata tgaactcttc ctcttccatt tttcctcaca cccttaaagc ttcaacaaaa     420
ccagatcaag cttctttcac cattttcact cttctttaag ctttctttct taatttctct     480
catttcgaat tttaaacaca aaacctaaac g                                     511
```

```
<210> SEQ ID NO 8
<211> LENGTH: 396
<212> TYPE: DNA
<213> ORGANISM: Arabidopsis thaliana
<220> FEATURE:
<221> NAME/KEY: promoter
<222> LOCATION: (1)..(396)
<223> OTHER INFORMATION: transcription regulating sequence from
      Arabidopsis thaliana gene At5g54510

<400> SEQUENCE: 8
```

```
atttctttaa agagaataat ttaagttaaa tcagggggta gaaaaaatta attcaaccat       60
caaatatatt ttattaacta aaataaagtg ggagaattca agaatactat atagtttgaa     120
tgtccttaaa ctattaaacc ttttttattca agccagtacg ggtattgacc aatatagaaa    180
acaaaattat ataaatacca cttttttgtaa tgaaacgaac taaaataaaa taaacgacat    240
tataaagtaa atcaaattaa acacgaatag taagccgttc acttaaatcc tggatttcaa    300
catactgtga aatgaccgtt atacccttttg atatcttctt caccctcttc ctctttcccc   360
ctatatatat gaactcttcc tcttccattt ttcctc                                396
```

```
<210> SEQ ID NO 9
<211> LENGTH: 2181
<212> TYPE: DNA
<213> ORGANISM: Arabidopsis thaliana
<220> FEATURE:
```

```
<221> NAME/KEY: CDS
<222> LOCATION: (115)..(1953)
<223> OTHER INFORMATION: coding for auxin-responsive GH3 protein

<400> SEQUENCE: 9
acacccttaa agcttcaaca aaaccagatc aagcttcttt caccattttc actcttcttt       60
aagctttctt tcttaatttc tctcatttcg aattttaaac acaaaaccta aacg atg       117
                                                            Met
                                                             1 cct gag gca cca aag atc gca gct ttg gag gtt tct gat gag agc ctc       165
Pro Glu Ala Pro Lys Ile Ala Ala Leu Glu Val Ser Asp Glu Ser Leu
         5                  10                  15 gct gag aag aac aag aac aaa ctc caa ttc atc gaa gac gtg acc acg       213
Ala Glu Lys Asn Lys Asn Lys Leu Gln Phe Ile Glu Asp Val Thr Thr
 20                  25                  30 aac gca gat gat gtt cag aga cga gtt ctt gaa gag atc ctt tca cgt       261
Asn Ala Asp Asp Val Gln Arg Arg Val Leu Glu Glu Ile Leu Ser Arg
 35                  40                  45 aat gct gat gtg gag tat ctt aaa cga cac ggg ctc gaa gga cga acc       309
Asn Ala Asp Val Glu Tyr Leu Lys Arg His Gly Leu Glu Gly Arg Thr
50                  55                  60                  65 gat cgt gag act ttc aaa cat atc atg cct gtc gta act tac gaa gat       357
Asp Arg Glu Thr Phe Lys His Ile Met Pro Val Val Thr Tyr Glu Asp
                 70                  75                  80 att caa cct gag atc aac aga atc gcc aat ggt gat aag tct caa gtc       405
Ile Gln Pro Glu Ile Asn Arg Ile Ala Asn Gly Asp Lys Ser Gln Val
             85                  90                  95 ctc tgt tct aac ccc atc tct gag ttc ctc aca agt tct ggg act tct       453
Leu Cys Ser Asn Pro Ile Ser Glu Phe Leu Thr Ser Ser Gly Thr Ser
        100                 105                 110 ggt gga gag agg aaa ctg atg cca aca atc gaa gag gaa cta gac aga       501
Gly Gly Glu Arg Lys Leu Met Pro Thr Ile Glu Glu Glu Leu Asp Arg
115                 120                 125 aga tca ctt ctc tac agt ctc ttg atg cct gtg atg gac cag ttt gtt       549
Arg Ser Leu Leu Tyr Ser Leu Leu Met Pro Val Met Asp Gln Phe Val
130                 135                 140                 145 cct ggt ctt gac aaa ggc aaa ggg atg tat ttt ctg ttt atc aaa tca       597
Pro Gly Leu Asp Lys Gly Lys Gly Met Tyr Phe Leu Phe Ile Lys Ser
                150                 155                 160 gaa tcc aag aca cca ggt ggt ctc cct gct cgt cct gtt tta acc agt       645
Glu Ser Lys Thr Pro Gly Gly Leu Pro Ala Arg Pro Val Leu Thr Ser
            165                 170                 175 tac tac aaa tcc tct cac ttc aaa aac aga cct tat gat cct tac acc       693
Tyr Tyr Lys Ser Ser His Phe Lys Asn Arg Pro Tyr Asp Pro Tyr Thr
        180                 185                 190 aac tac aca agt ccc aac caa acc atc ctt tgt tct gac tct tac cag       741
Asn Tyr Thr Ser Pro Asn Gln Thr Ile Leu Cys Ser Asp Ser Tyr Gln
195                 200                 205 agc atg tac tct caa atg ctt tgt ggt tta tgc caa cac aaa gag gtt       789
Ser Met Tyr Ser Gln Met Leu Cys Gly Leu Cys Gln His Lys Glu Val
210                 215                 220                 225 ctt cgt gtt ggt gct gtt ttt gcc tct ggt ttc att aga gcc atc aag       837
Leu Arg Val Gly Ala Val Phe Ala Ser Gly Phe Ile Arg Ala Ile Lys
                230                 235                 240 ttt ctt gag aaa cat tgg cct gag cta gct cgt gac att aga acc ggt       885
Phe Leu Glu Lys His Trp Pro Glu Leu Ala Arg Asp Ile Arg Thr Gly
            245                 250                 255 act ctc agt tcc gag ata acc gat tct tcg gtt cgt gag gcg gtc ggg       933
Thr Leu Ser Ser Glu Ile Thr Asp Ser Ser Val Arg Glu Ala Val Gly
        260                 265                 270
```

```
gag att ctt aaa ccg gat cct aag ctt gct gat ttc gtc gaa tct gaa      981
Glu Ile Leu Lys Pro Asp Pro Lys Leu Ala Asp Phe Val Glu Ser Glu
    275                 280                 285 tgc agg aag act tct tgg caa ggg atc atc act agg ctt tgg cca aac     1029
Cys Arg Lys Thr Ser Trp Gln Gly Ile Ile Thr Arg Leu Trp Pro Asn
290                 295                 300                 305 act aag tat gtg gat gtg att gtg act gga aca atg tca cag tat att     1077
Thr Lys Tyr Val Asp Val Ile Val Thr Gly Thr Met Ser Gln Tyr Ile
                310                 315                 320 cca act ctg gat tat tac agc aat ggt ttg cct ctt gtc tgc aca atg     1125
Pro Thr Leu Asp Tyr Tyr Ser Asn Gly Leu Pro Leu Val Cys Thr Met
            325                 330                 335 tat gct tct tcg gag tgt tac ttc ggt gtg aat ctc agg cca ctc tgc     1173
Tyr Ala Ser Ser Glu Cys Tyr Phe Gly Val Asn Leu Arg Pro Leu Cys
        340                 345                 350 aaa cca agt gaa gtc tct tac act ctc ata ccg aac atg gcg tat ttc     1221
Lys Pro Ser Glu Val Ser Tyr Thr Leu Ile Pro Asn Met Ala Tyr Phe
    355                 360                 365 gag ttc ttg cct gtt cat agg aac agt gga gtt act agc tct atc agt     1269
Glu Phe Leu Pro Val His Arg Asn Ser Gly Val Thr Ser Ser Ile Ser
370                 375                 380                 385 ctt cca aaa gca ctc act gag aaa gaa caa caa gag ctt gtt gat ctc     1317
Leu Pro Lys Ala Leu Thr Glu Lys Glu Gln Gln Glu Leu Val Asp Leu
                390                 395                 400 gtc gat gtc aag ctt ggt cag gag tac gag ctt gtt gtc acc acc tat     1365
Val Asp Val Lys Leu Gly Gln Glu Tyr Glu Leu Val Val Thr Thr Tyr
            405                 410                 415 gct ggg ctt tac agg tac aga gtg ggt gat gtc cta agc gtg gct ggt     1413
Ala Gly Leu Tyr Arg Tyr Arg Val Gly Asp Val Leu Ser Val Ala Gly
        420                 425                 430 ttc aag aac aat gcg cct cag ttc agc ttc ata tgc cgc aag aac gtg     1461
Phe Lys Asn Asn Ala Pro Gln Phe Ser Phe Ile Cys Arg Lys Asn Val
    435                 440                 445 gtc tta agc att gac tcg gac aaa acc gat gag gtt gag ctt caa aac     1509
Val Leu Ser Ile Asp Ser Asp Lys Thr Asp Glu Val Glu Leu Gln Asn
450                 455                 460                 465 gca gtt aaa aac gcg gta aca cac ctt gtt ccg ttt gat gct tca ctc     1557
Ala Val Lys Asn Ala Val Thr His Leu Val Pro Phe Asp Ala Ser Leu
                470                 475                 480 tcc gag tac act agc tat gcg gac aca tca tct atc ccg ggc cac tat     1605
Ser Glu Tyr Thr Ser Tyr Ala Asp Thr Ser Ser Ile Pro Gly His Tyr
            485                 490                 495 gtc tta ttc tgg gag ctc tgc ttg aac ggt aac acg cca att cct ccc     1653
Val Leu Phe Trp Glu Leu Cys Leu Asn Gly Asn Thr Pro Ile Pro Pro
        500                 505                 510 tcg gtc ttc gag gat tgc tgt tta acc ata gag gaa tca ctt aac agt     1701
Ser Val Phe Glu Asp Cys Cys Leu Thr Ile Glu Glu Ser Leu Asn Ser
    515                 520                 525 gtg tat aga caa gga agg gtc agt gat aag tcc att gga cca ttg gag     1749
Val Tyr Arg Gln Gly Arg Val Ser Asp Lys Ser Ile Gly Pro Leu Glu
530                 535                 540                 545 atc aag atg gtc gag tca ggg act ttc gat aag ctc atg gat tat gcg     1797
Ile Lys Met Val Glu Ser Gly Thr Phe Asp Lys Leu Met Asp Tyr Ala
                550                 555                 560 ata agc ttg ggt gca tcg atc aat cag tac aag aca cca agg tgt gtg     1845
Ile Ser Leu Gly Ala Ser Ile Asn Gln Tyr Lys Thr Pro Arg Cys Val
            565                 570                 575 aag ttt gct ccg atc att gag ctt tta aac tct agg gtt gtt gat agt     1893
Lys Phe Ala Pro Ile Ile Glu Leu Leu Asn Ser Arg Val Val Asp Ser
```

-continued

```
                580                 585                 590
tac ttc agc ccc aag tgt cct aaa tgg tcc cct ggt cac aag caa tgg      1941
Tyr Phe Ser Pro Lys Cys Pro Lys Trp Ser Pro Gly His Lys Gln Trp
    595                 600                 605 ggg agt aac taa agaggaaact ttggggaaga agaaagactc tctatgaagt          1993
Gly Ser Asn
610 agaaggttct gttttgtaat caaatgaata tcgagaaaag tgataaatta ttatgtctgt    2053 ttgttctaat ttaaatctta atttaatttt gctttactgt ttttgttttg aaatatgttt    2113 agattctagt catatgtaca tagccggttt atgtttctct aagcgactct tttaagtttc    2173 tccagcct                                                             2181
```

<210> SEQ ID NO 10
<211> LENGTH: 612
<212> TYPE: PRT
<213> ORGANISM: Arabidopsis thaliana

<400> SEQUENCE: 10

```
Met Pro Glu Ala Pro Lys Ile Ala Ala Leu Glu Val Ser Asp Glu Ser
1               5                   10                  15

Leu Ala Glu Lys Asn Lys Asn Lys Leu Gln Phe Ile Glu Asp Val Thr
            20                  25                  30

Thr Asn Ala Asp Asp Val Gln Arg Val Leu Glu Glu Ile Leu Ser
        35                  40                  45

Arg Asn Ala Asp Val Glu Tyr Leu Lys Arg His Gly Leu Glu Gly Arg
    50                  55                  60

Thr Asp Arg Glu Thr Phe Lys His Ile Met Pro Val Val Thr Tyr Glu
65                  70                  75                  80

Asp Ile Gln Pro Glu Ile Asn Arg Ile Ala Asn Gly Asp Lys Ser Gln
                85                  90                  95

Val Leu Cys Ser Asn Pro Ile Ser Glu Phe Leu Thr Ser Ser Gly Thr
            100                 105                 110

Ser Gly Gly Glu Arg Lys Leu Met Pro Thr Ile Glu Glu Glu Leu Asp
        115                 120                 125

Arg Arg Ser Leu Leu Tyr Ser Leu Leu Met Pro Val Met Asp Gln Phe
    130                 135                 140

Val Pro Gly Leu Asp Lys Gly Lys Gly Met Tyr Phe Leu Phe Ile Lys
145                 150                 155                 160

Ser Glu Ser Lys Thr Pro Gly Gly Leu Pro Ala Arg Pro Val Leu Thr
                165                 170                 175

Ser Tyr Tyr Lys Ser Ser His Phe Lys Asn Arg Pro Tyr Asp Pro Tyr
            180                 185                 190

Thr Asn Tyr Thr Ser Pro Asn Gln Thr Ile Leu Cys Ser Asp Ser Tyr
        195                 200                 205

Gln Ser Met Tyr Ser Gln Met Leu Cys Gly Leu Cys Gln His Lys Glu
    210                 215                 220

Val Leu Arg Val Gly Ala Val Phe Ala Ser Gly Phe Ile Arg Ala Ile
225                 230                 235                 240

Lys Phe Leu Glu Lys His Trp Pro Glu Leu Ala Arg Asp Ile Arg Thr
                245                 250                 255

Gly Thr Leu Ser Ser Glu Ile Thr Asp Ser Ser Val Arg Glu Ala Val
            260                 265                 270

Gly Glu Ile Leu Lys Pro Asp Pro Lys Leu Ala Asp Phe Val Glu Ser
        275                 280                 285
```

```
Glu Cys Arg Lys Thr Ser Trp Gln Gly Ile Ile Thr Arg Leu Trp Pro
    290                 295                 300

Asn Thr Lys Tyr Val Asp Val Ile Val Thr Gly Thr Met Ser Gln Tyr
305                 310                 315                 320

Ile Pro Thr Leu Asp Tyr Tyr Ser Asn Gly Leu Pro Leu Val Cys Thr
                325                 330                 335

Met Tyr Ala Ser Ser Glu Cys Tyr Phe Gly Val Asn Leu Arg Pro Leu
            340                 345                 350

Cys Lys Pro Ser Glu Val Ser Tyr Thr Leu Ile Pro Asn Met Ala Tyr
        355                 360                 365

Phe Glu Phe Leu Pro Val His Arg Asn Ser Gly Val Thr Ser Ser Ile
    370                 375                 380

Ser Leu Pro Lys Ala Leu Thr Glu Lys Glu Gln Gln Glu Leu Val Asp
385                 390                 395                 400

Leu Val Asp Val Lys Leu Gly Gln Glu Tyr Glu Leu Val Val Thr Thr
                405                 410                 415

Tyr Ala Gly Leu Tyr Arg Tyr Arg Val Gly Asp Val Leu Ser Val Ala
            420                 425                 430

Gly Phe Lys Asn Asn Ala Pro Gln Phe Ser Phe Ile Cys Arg Lys Asn
        435                 440                 445

Val Val Leu Ser Ile Asp Ser Asp Lys Thr Asp Glu Val Glu Leu Gln
    450                 455                 460

Asn Ala Val Lys Asn Ala Val Thr His Leu Val Pro Phe Asp Ala Ser
465                 470                 475                 480

Leu Ser Glu Tyr Thr Ser Tyr Ala Asp Thr Ser Ser Ile Pro Gly His
                485                 490                 495

Tyr Val Leu Phe Trp Glu Leu Cys Leu Asn Gly Asn Thr Pro Ile Pro
            500                 505                 510

Pro Ser Val Phe Glu Asp Cys Cys Leu Thr Ile Glu Glu Ser Leu Asn
        515                 520                 525

Ser Val Tyr Arg Gln Gly Arg Val Ser Asp Lys Ser Ile Gly Pro Leu
    530                 535                 540

Glu Ile Lys Met Val Glu Ser Gly Thr Phe Asp Lys Leu Met Asp Tyr
545                 550                 555                 560

Ala Ile Ser Leu Gly Ala Ser Ile Asn Gln Tyr Lys Thr Pro Arg Cys
                565                 570                 575

Val Lys Phe Ala Pro Ile Ile Glu Leu Leu Asn Ser Arg Val Val Asp
            580                 585                 590

Ser Tyr Phe Ser Pro Lys Cys Pro Lys Trp Ser Pro Gly His Lys Gln
        595                 600                 605

Trp Gly Ser Asn
    610
```

<210> SEQ ID NO 11
<211> LENGTH: 2552
<212> TYPE: DNA
<213> ORGANISM: Arabidopsis thaliana
<220> FEATURE:
<221> NAME/KEY: promoter
<222> LOCATION: (1)..(2552)
<223> OTHER INFORMATION: transcription regulating sequence from
      Arabidopsis thaliana gene At2g26970

<400> SEQUENCE: 11
tgttttggga gatgcattca ataaagaagc cttcttgata aacagagatc cttgtgagtt      60

```
ttgatgttag gctttaaacg ttcaacatca ttacagcacc cgttttgttt tgtcttttct      120 tttacgatg aagatccttt tgacacacaa aataaataaa atattgaagg aagttccaaa      180
aatgacatgg atagtcatga aattaatagt cacaaatggt ttcttcttct tattcttcgt      240
ctaatctttt aagtcttgat gaagaaacag atgatggtat attgtgaact aatatatgga      300
ataaacaaaa tgttgactgt cacacatgaa tttaaattgt tatggattta tatctacgaa      360
accaaaaggg tgaatatcac atatggatta agtttgtctt agatatctat acaacgaagt      420
ttaatatatt ttagctcttc ttgtcttcgt gtgttttcct tttactttct tataaatttt      480
tttgggtaca tacaacgata tatgtgtttt gttgatcaat aaaaagttca ccttatctcg      540
tagagaacta atcgagtgat ggacggcgtt tgttatttaa tttgtggttg aaatttatca      600
cctacatgac tacatcatct acaataaaat gcaaaatgg ctatattctt cataaaattc       660
caaattctag tcacaaaata tcaaaattca agaaacgca aattaaatac acacaaacga       720
aatgttcttt ccaagtaaaa taagagtga tcatagttgt tcgaagggtt cctcgtcatc       780
agaggggttc ttgaaagcag tgcttccgaa gagcatgaaa cccacggcga atccggcgat      840
agcgacaatg aaaactccac cgttaaagga cataacggcg agcatcacga gataagcaag      900
gcctgtcttg agtgtgtaga ctgcggtctg aacgagcccc ttggcgcggc tagtggagcc      960
acgtccacga aggatcgaag aatgggcaag ccactcgacg ataacagcaa ggaggaagac     1020
gacgatgaga catagaacgt acatgccgag acttgtcccg ggccagccgg agaagagtat     1080
ctccgtgttc ttcccccaga agaaagtcct atgcatcatg atcatgttgg aattggtatg     1140
atttaccatt gatgatggtg atgatggtgg catgttacca tgatccatta tatgataagt     1200
ttctgaaatt ttttgtttgg gacaaaactt agagaaaatg gtttcgtatt tattgtgatg     1260
ttcttgttat catgtggtct cttaaatgtg tttgtggttg tactcacgtt ttgacttgtc     1320
aaactttgtg tagtacaagt agaagtcaat actaattta gaaagccttt taaatacccta     1380 ttcagttatt caacttattt tcatgatata aatggtaaca caccacttgt agaattgtgg     1440
tggaagaaaa acgatttaca tcatttgaac ataatttgag aaagtgatga aattatatt      1500 cgtagtggaa tttaacaagt tattcttcta acgatatttt acttataaat caatgacaac     1560
aacattgtgt taagcttatg agtttcaagt tcagttcaat caacaaaatg caactctccc     1620
caattcatca cttgcaaaac tctaaacata gaccaaagaa attaggcaaa cccaaaccta     1680
cgaagactta tcaaaatata aaatgtaaa tttggctcaa aaccttggac aagaaacata     1740
tcaatctagg tctaaaattc actggttcgt cacaacccat tctagaaaat tcgaaaacaa     1800
ggacaaaacg aaccaataca gacatatagt ggatacaacc atagaaatgt tatcaagatc     1860
aaacaaatat acaagatata taaaaagtt ttctaatata cgatatcaaa tcagttgtaa      1920
tctcaagtgt tagtcgcaaa tgtggtcaca gttatgggat tgtaaggtag caaatcagtt     1980
gtaatctcaa gtgttagtcg gaaatgtggt cacaattatg agattacttt gcgaattgcg     2040
acattagtca atttctatac aaaattaaat ctatctaatt attttttgac caatatggta     2100
tatgttcttt ttactgacta aaatagttat aattatattt tttaagtaaa acatgttaat     2160
taagtttatt tcgccgtttt tttttttatt tgtttggctt tgttttttggg tcaaagagac     2220 cgattttttc tcttttaggt taccttcctc cgattagtct tactgaaaga aaaaaatgaa     2280
caaactctcc aacgctttct ctgtcctggc tttcgccgat gaagatgctc caatggcttc     2340
ttcttcttcc actggtatcc cctgtttccc tcttccgatt tgattacaac acaaaaccat     2400
gtttagattt ttgagactga atttgataat atattgacta aattaatcag tgatttagag     2460
```

```
gtcaagagtc aattaaagta ttgacccttta aactttagtt tttttactca tggcactgtc    2520
tcttgtggct acaagatttg ttggtttgag ac                                   2552

<210> SEQ ID NO 12
<211> LENGTH: 2552
<212> TYPE: DNA
<213> ORGANISM: Arabidopsis thaliana
<220> FEATURE:
<221> NAME/KEY: promoter
<222> LOCATION: (1)..(2552)
<223> OTHER INFORMATION: transcription regulating sequence from
      Arabidopsis thaliana gene At2g26970

<400> SEQUENCE: 12
tgttttggga gatgcattca ataaagaagc cttcttgata aacagagatc cttgtgagtt      60
ttgatgttag gctttaaacg ttcaacatca ttacagcacc cgttttgttt tgtcttttct     120
ttttacgatg aagatccttt tgacacacaa aataaataaa atattgaagg aagttccaaa     180
aatgacatgg atagtcatga aattaatagt cacaaatggt ttcttcttct tattcttcgt     240
ctaatctttt aagtcttgat gaagaaacag atgatggtat attgtgaact aatatatgga     300
ataaacaaaa tgttgactgt cacacatgaa tttaaattgt tatggattta tatctacgaa     360
accaaaaggg tgaatatcac atatggatta agtttgtctt agatatctat acaatgaagt     420
ttaatatatt ttagctcttc ttgtcttcgt gtgttttttct tttacttcct tataaatttt    480
tttgggtaca tacaacgata tatgtgtttt gttgatcaat aaaaagttca ccttatctcg     540
tagagaacta atcgagtgat ggacggcgtt tgttatttaa tttgtggttg aaatttatca     600
tctacatgac tacatcatct acaataaaat gcaaaatgg ctatattctt cataaaattc      660
caaattctag tcacaaaata tcaaaattca agaaacgca aattaaatac acacaaacga      720
aatgttcttt ccaagtaaaa taagagtga tcatagttgt tcgaagggtt tctcgtcatc      780
agaggggttc ttgaaagcag tgcttccgaa gagcatgaaa cccacggcga atccggcgat     840
agcgacaatg aaaactccac cgttaaagga cataacggcg agcatcacga gataagcaag     900
gcctgtcttg agtgtgtaga ctgcggtctg aacgagcccc ttggcgcggc tagtggagcc     960
acgtccacga aggatcgaag aatgggcaag ccactcgacg ataacagcaa ggaggaagac    1020
gacgatgaga catagaacgt acatgccgag acttgtcccg ggccagccgg agaagagtat    1080
ctccgtgttc tttccccaga agaaagtcat atgcatcatg atcatgttgg aattggtatg    1140
atttaccatt gatgatggtg atgatggtgg catgttacca tgatccatta tatgataagt    1200
ttctgaaatt ttttgtttgg gacaaaactt agagaaaatg gtttcgtatt tattgtgatg    1260
ttcttgttat catgtggtct cttaaatgtg tttgtggttg tactcacgtt ttgacttgtc    1320
aaactttgtg tagtacaagt agaagtcaat actaattta gaaagccttt taaatacccta    1380 ttcagttatt caacttattt tcatgatata atggtaaca caccatttgt agaattgtgg     1440
tggaagaaaa acgatttaca tcatttgaac ataatttgag aaagtgatga aatttatatt    1500
cgtagtggaa tttaacaagt tattcttcta aacgatattt acttataaat caatgacaac    1560
aacattgtgt taagcttatg agtttcaagt tcagttcaat caacaaaatg caactctccc    1620
caattcatca cttgcaaaac tctaaacata gaccaaagaa attaggcaaa cccaaaccta    1680
cgaagactta tcaaaatata aaatgtaaa tttggctcaa accttggac aagaaacata     1740 tcaatctagg tctaaaattc actggttcgt cacaacccat tctagaaaat tcgaaaacaa    1800
ggacaaaacg aaccaataca gacatatagt ggatacaacc atagaaatgt tatcaagatc    1860
```

-continued

```
aaacaaatat acaagatata taaaaaagtt ttctaatata cgatatcaaa tcagttgtaa    1920
tctcaagtgt tagtcgcaaa tgtggtcaca gttatgggat tgtaaggtag caaatcagtt    1980
gtaatctcaa gtgttagtcg gaaatgtggt cacaattatg agattacttt gcgaattgcg    2040
acattagtca atttctatac aaaattaaat ctatctaatt attttttgac caatatggta    2100
tatgttcttt ttactgacta aaatagttat aattatattt tttaagtaaa acatgttaat    2160
taagtttatt tcgccgtttt ttttttttat ttgtttggct ttgttttggg gtcaaagaga    2220 ccgattttt ctcttttagg ttaccttcct ccgattagtc ttactgaaag aaaaaaatga     2280
acaaactctc caacgctttc tctgtcctgg ctttcgccga tgaagatgct ccaatggctt    2340
cttcttcttc cactggtatc ccctgtttcc ctcttccgat ttgattacaa cacaaaacca    2400
tgtttagatt tttgagactg aatttgataa tatattgact aaattaatca gtgatttaga    2460
ggtcaagagt caattaaagt attgacctttt aaactttagt tttttttactc atggcactgt   2520 ctcttgtggc tacaagattt gttggtttga ga                                  2552
```

<210> SEQ ID NO 13
<211> LENGTH: 828
<212> TYPE: DNA
<213> ORGANISM: Arabidopsis thaliana
<220> FEATURE:
<221> NAME/KEY: CDS
<222> LOCATION: (12)..(680)
<223> OTHER INFORMATION: coding for exonuclease family protein

<400> SEQUENCE: 13

```
gaaagaaaaa a atg aac aaa ctc tcc aac gct ttc tct gtc ctg gct ttc      50
            Met Asn Lys Leu Ser Asn Ala Phe Ser Val Leu Ala Phe
            1               5                   10 gcc gat gaa gat gct cca atg gct tct tct tct tcc act ggg aaa caa      98
Ala Asp Glu Asp Ala Pro Met Ala Ser Ser Ser Ser Thr Gly Lys Gln
 15                  20                  25 gaa gaa agt gta aat ggg tca ctt gag gat gga gat tac aag caa cca     146
Glu Glu Ser Val Asn Gly Ser Leu Glu Asp Gly Asp Tyr Lys Gln Pro
30                  35                  40                  45 ctt gtt tgg att gac ttg gaa atg act gga tta aat gtt gaa gtt gac     194
Leu Val Trp Ile Asp Leu Glu Met Thr Gly Leu Asn Val Glu Val Asp
                50                  55                  60 agg ata ttg gag att gca tgt ata att act aat gga gat tta aca caa     242
Arg Ile Leu Glu Ile Ala Cys Ile Ile Thr Asn Gly Asp Leu Thr Gln
             65                  70                  75 tca gtg gag ggt cca gat tta gtt gta cgt caa acg aaa gac tgt ttg     290
Ser Val Glu Gly Pro Asp Leu Val Val Arg Gln Thr Lys Asp Cys Leu
         80                  85                  90 gat aaa atg gat gac tgg tgt caa act cat cat gga gct agt ggg ttg     338
Asp Lys Met Asp Asp Trp Cys Gln Thr His His Gly Ala Ser Gly Leu
     95                  100                 105 acg aag aaa gtg ctc ctc agt gcg ata act gaa agg gaa gct gag caa     386
Thr Lys Lys Val Leu Leu Ser Ala Ile Thr Glu Arg Glu Ala Glu Gln
110                 115                 120                 125 aag gtc atc gaa ttc gta aag aag cat gtt ggt tcc gga aat cca ctg     434
Lys Val Ile Glu Phe Val Lys Lys His Val Gly Ser Gly Asn Pro Leu
                130                 135                 140 tta gct gga aac tca gtc tat gtc gat ttc ctt ttc tta aag aaa tac     482
Leu Ala Gly Asn Ser Val Tyr Val Asp Phe Leu Phe Leu Lys Lys Tyr
            145                 150                 155 atg cca gaa tta gct gcc ctt ttc cct cat ata ctc gtc gat gtc agt     530
Met Pro Glu Leu Ala Ala Leu Phe Pro His Ile Leu Val Asp Val Ser
```

-continued

```
              160                 165                 170
agc gtc aag gct tta tgc gcc cga tgg ttc ccc ata gag aga agg aaa    578
Ser Val Lys Ala Leu Cys Ala Arg Trp Phe Pro Ile Glu Arg Arg Lys
    175                 180                 185 gct cct gcc aag aaa aac aat cac aga gcc atg gat gat ata aga gaa    626
Ala Pro Ala Lys Lys Asn Asn His Arg Ala Met Asp Asp Ile Arg Glu
190                 195                 200                 205 agt ata aag gag ctt aag tac tac aag aaa aca ata ttc aaa gct agg    674
Ser Ile Lys Glu Leu Lys Tyr Tyr Lys Lys Thr Ile Phe Lys Ala Arg
                210                 215                 220 aga tga gtggagttgg gtactgcaat atgcttactt actagttaga aggatccgtt     730
Arg ttagttttac gaattcggca ttgttattct cttgacgatt gtatcctcaa aacctaaatt    790
gtattggtct cttgataaag aaaaaccttt gaagatgg                           828

<210> SEQ ID NO 14
<211> LENGTH: 222
<212> TYPE: PRT
<213> ORGANISM: Arabidopsis thaliana

<400> SEQUENCE: 14

Met Asn Lys Leu Ser Asn Ala Phe Ser Val Leu Ala Phe Ala Asp Glu
1               5                   10                  15

Asp Ala Pro Met Ala Ser Ser Ser Thr Gly Lys Gln Glu Glu Ser
                20                  25                  30

Val Asn Gly Ser Leu Glu Asp Gly Asp Tyr Lys Gln Pro Leu Val Trp
            35                  40                  45

Ile Asp Leu Glu Met Thr Gly Leu Asn Val Glu Val Asp Arg Ile Leu
        50                  55                  60

Glu Ile Ala Cys Ile Ile Thr Asn Gly Asp Leu Thr Gln Ser Val Glu
65                  70                  75                  80

Gly Pro Asp Leu Val Val Arg Gln Thr Lys Asp Cys Leu Asp Lys Met
                85                  90                  95

Asp Asp Trp Cys Gln Thr His His Gly Ala Ser Gly Leu Thr Lys Lys
                100                 105                 110

Val Leu Leu Ser Ala Ile Thr Glu Arg Glu Ala Glu Gln Lys Val Ile
            115                 120                 125

Glu Phe Val Lys Lys His Val Gly Ser Gly Asn Pro Leu Leu Ala Gly
        130                 135                 140

Asn Ser Val Tyr Val Asp Phe Leu Phe Leu Lys Lys Tyr Met Pro Glu
145                 150                 155                 160

Leu Ala Ala Leu Phe Pro His Ile Leu Val Asp Val Ser Ser Val Lys
                165                 170                 175

Ala Leu Cys Ala Arg Trp Phe Pro Ile Glu Arg Arg Lys Ala Pro Ala
            180                 185                 190

Lys Lys Asn Asn His Arg Ala Met Asp Asp Ile Arg Glu Ser Ile Lys
        195                 200                 205

Glu Leu Lys Tyr Tyr Lys Lys Thr Ile Phe Lys Ala Arg Arg
    210                 215                 220

<210> SEQ ID NO 15
<211> LENGTH: 2193
<212> TYPE: DNA
<213> ORGANISM: Arabidopsis thaliana
<220> FEATURE:
<221> NAME/KEY: promoter
<222> LOCATION: (1)..(2193)
```

<223> OTHER INFORMATION: transcription regulating sequence from Arabidopsis thaliana gene At2g01180

<400> SEQUENCE: 15

```
ataatcaacc ttctcgtttg atcgtgattt ggtttatgtt tgtcgatctc atattataca      60
gaaacacgat taaaaggaga tttcaagaaa agcccttata ataagaactc tatgaaacct     120
aagttataag aagaggtgac ttgactacat tttatggttg ggaatgaaat tcgaagatct     180
agctgttgga aagacaggcg taaagtttgt gtaatgtata aacagaatct cttttgtacg     240
aaagaccatt ctacagaatt gacgtgttaa tgtgtatatc tggaattagg tattaaacat     300
taattttgag tttgtatatc ttctctcttt ttcttacgat caatatgcaa attagcaaat     360
agagagacgt aatgatgatg tttgtgcatt accgagtgag ataactaaat gatgtttcaa     420
gaaatgcaaa agtgaaacaa ggaaacctaa aagagtaagc aaacaaacaa caaatcagca     480
ataaaatatt taaatcattt taaaatttaa ttaatattaa ttcgttttta ctttaaggtt     540
tttggtaact tttttttggag accgtgatgt cgtcaaaaca ttcaagatgt atattgatta     600
ttgacattct ctcttttctct ctattgtcct tctttttttt cttctttttac ttttttaactt     660
taaaactata tatttatatc cataaaatat ataaaagaaa tcttattagt aactaaaagt     720
tgtgcaagtt ttttagctat taattttatc ggaatagtgc aaaactgtta gaaaaaactg     780
tataaaaaac tgttaaaaaa agctgagaat aaaattttt ataacacttt tggtaacaat     840
tttgtgattg gtaaatgtca aactatttat actgttttaa agtgttaagt ggttaccatt     900
caaaaccaaa accttaaaaa ttaaagccgt tatgctattt ttttaataaa gaagacatga     960
ttttgcccta tcaaattaaa attggtgtgt tgatgagtgc aaaagcgtag gcaaataaat    1020
cacacatcat taacaaaaaa aaaaaatcac acataaaagt gtaattgtga ggaaaaaaga    1080
tgtttccaat ttttaagtcc accaccaaac tggacccact aaccctact cagggtatac     1140
aattccattt ccaccatac acaattatag tagtccacct ttttttctttt ctttctacac    1200
atatctggat tccagctttt aagtaggatt attattggtt ggtaaaagat gcaaagaata    1260
tgagaaaagg tctaattgcg tgctccataa acccttattc tagttcaacc ataattgtca    1320
gtcaatagaa gcaagataat ttgaacgtcc aagtcatcat catctttttt tttctttctg    1380
aaatttcgtt ttacaataaa caagaaagg ttccgagtcc tcaagcatct ctcacgtcgg     1440
agcaagttgc catgcactct ccaaaataaa ataaaaaaca gacaaagact ttagacttgt    1500
gacttttcga cctcattatg tacttactta cttcatcttc tatttggcac ccacaaacag    1560
tagtttccac tttcttcctc aataagttcc attttggat tctttcctat ttttacacaa     1620
atttgttgta ttctaaaaag ttatatattc tatttgctgg gctttagata tgggctggct    1680
ctggatatgt gtgtaatgga tacatattag taaatagtta agtccaaaaa agaaattata    1740
aaccccctat gtagtttgaa aactgaatca tctgacaaaa cgagcaggga aggcccataa    1800
taaggcctaa taagtaaggt aagcccacag agaaatatac ttacgggctt ggatttccga    1860
accttcctaa aaagtgggac ctacgcggct gagaagaaag acgaaggcca tatcagaccg    1920
gcgataactg aaaagtcaaa agtcaaaatt caagaggaag aggagtttct aatcatgtct    1980
ctctctgttt tcttcttatt cttctatcaa accgtcaagt tgggaaacaa aacaaaactc    2040
gcaagtttaa caacgcgtct tctacctcct cctcatcgga ctatttatct atagtcttcg    2100
ttagatcaat tcctctgttt tactcctaag tttcgagatc cacatttctc tttaacctca    2160
tctcatctct tagtcgagat cttcactttc tgc                                 2193
```

```
<210> SEQ ID NO 16
<211> LENGTH: 2192
<212> TYPE: DNA
<213> ORGANISM: Arabidopsis thaliana
<220> FEATURE:
<221> NAME/KEY: promoter
<222> LOCATION: (1)..(2192)
<223> OTHER INFORMATION: transcription regulating sequence from
      Arabidopsis thaliana gene At2g01180

<400> SEQUENCE: 16
ataatcaacc ttctcgtttg atcgtgattt ggtttatgtt tgtcgatctc atattataca      60
gaaacacgat taaaaggaga tttcaagaaa agcccttata ataagaactc tatgaaacct     120
aagttataag aagaggtgac ttgactacat tttatggttg ggaatgaaat tcgaagatct     180
agctgttgga aagacaggcg taaagtttgt gtaatgtata aacagaatct cttttgtacg     240
aaagaccatt ctacagaatt gacgtgttaa tgtgtatatc tggaattagg tattaaacat     300
taattttgag tttgtatatc ttctctcttt ttcttacgat caatatgcaa attagcaaat     360
agagagacgt aatgatgatg tttgtgcatt accgagtgag ataactaaat gatgtttcaa     420
gaaatgcaaa agtgaaacaa ggaaacctaa aagagtaagc aaacaaacaa caaatcagca     480
ataaaatatt taaatcattt taaaatttaa ttaatattaa ttcgtttta ctttaaggtt      540 tttggtaact ttttttggag accgtgatgt cgtcaaaaca ttcaagatgt atattgatta     600
ttgacattct ctctttctct ctattgtcct tcttttttt cttcttttac tttttaactt      660
taaaactata tatttatatc cataaaatat ataaagaaa tcttattagt aactaaaagt      720
tgtgcaagtt tttagctat taattttatc ggaatagtgc aaaactgtta gaaaaaactg     780
tataaaaaac tgttaaaaaa agctgagaat aaaattttt ataacacttt tggtaacaat      840
tttgtgattg gtaaatgtca aactatttat actgttttaa agtgttaagt ggttaccatt      900
caaaaccaaa accttaaaaa ttaaagccgt tatgctattt ttaataaaa gaagacatga      960 ttttgcccta tcaaattaaa attggtgtgt tgatgagtgc aaaagcgtag gcaaataaat    1020
cacacatcat taacaaaaaa aaaaaatcac acataaaagt gtaattgtga ggaaaaaaga    1080
tgtttccaat ttttaagtcc accaccaaac tggacccact aacccctact cagggtatac    1140
aattccattt ccaccatac acaattatag tagtccacct ttttcttttt ctttctacac     1200
atatctggat tccagttttt aagtaggatt attattggtt ggtaaaagat gcaaagaata    1260
tgagaaaagg tctaattgcg tgctccataa acccttattc tagttcaacc ataattgtca    1320
gtcaatagaa gcaagataat ttgaacgtcc aagtcatcat catctttttt tttctttctg    1380
aaatttcgtt ttacaataaa caagaaaagg ttccgagtcc tcaagcatct ctcacgtcgg    1440
agcaagttgc catgcactct ccaaaataaa ataaaaaaca gacaaagact ttagacttgt    1500 gactttcga cctcattatg tacttactta cttcatcttc tatttggcac ccacaaacag     1560
tagtttccac tttcttcctc aataagttcc attttggat tctttcctat ttttacacaa     1620
atttgttgta ttctaaaaag ttatatattc tatttgctgg gctttagata tgggctggct    1680
ctggatatgt gtgtaatgga tacatattag taaaatagtta agtccaaaaa agaaattata    1740
aaccccctat gtagtttgaa aactggatca tctgacaaaa cgagcaggga aggcccataa    1800
taaggcctaa taagtaaggt aagcccacag agaaatatac ttacgggctt ggatttccga    1860
accttcctaa aaagtgggac ctacgcggct gagaagaaag acgaaggcca tatcagaccg    1920
gcgataactg aaaagtcaaa agtcaaaatt caagaggaag aggagtttct aatcatgtct    1980
```

```
ctctctgttt tcttcttatt cttctatcaa accgtcaagt tgggaaacaa aacaaaactc      2040
gcaagtttaa caacgcgtct tctacctcct cctcatcgga ctatttatct atagtcttcg      2100
ttagatcaat tcctctgttt tactcctaag tttcgagatc cacatttctc tttaacctca      2160
tctcatctct tagtcgagat cttcactttc tg                                   2192

<210> SEQ ID NO 17
<211> LENGTH: 2658
<212> TYPE: DNA
<213> ORGANISM: Arabidopsis thaliana
<220> FEATURE:
<221> NAME/KEY: promoter
<222> LOCATION: (1)..(2658)
<223> OTHER INFORMATION: transcription regulating sequence from
      Arabidopsis thaliana gene At2g01180

<400> SEQUENCE: 17
ataatcaacc ttctcgtttg atcgtgattt ggtttatgtt tgtcgatctc atattataca       60
gaaacacgat taaaaggaga tttcaagaaa agcccttata ataagaactc tatgaaacct      120
aagttataag aagaggtgac ttgactacat tttatggttg ggaatgaaat tcgaagatct      180
agctgttgga aagacaggcg taaagtttgt gtaatgtata aacagaatct cttttgtacg      240
aaagaccatt ctacagaatt gacgtgttaa tgtgtatatc tggaattagg tattaaacat      300
taattttgag tttgtatatc ttctctcttt ttcttacgat caatatgcaa attagcaaat      360
agagagacgt aatgatgatg tttgtgcatt accgagtgag ataactaaat gatgtttcaa      420
gaaatgcaaa agtgaaacaa ggaaacctaa agagtaagc aaacaaacaa caaatcagca      480
ataaaatatt taaatcattt taaaatttaa ttaatattaa ttcgtttta ctttaaggtt      540 tttggtaact ttttttggag accgtgatgt cgtcaaaaca ttcaagatgt atattgatta      600
ttgacattct ctctttctct ctattgtcct tctttttttt cttcttttac ttttaactt       660 taaaactata tatttatatc cataaaatat ataaagaaa tcttattagt aactaaaagt      720
tgtgcaagtt ttttagctat taattttatc ggaatagtgc aaaactgtta gaaaaaactg      780
tataaaaaac tgttaaaaaa agctgagaat aaaattttt ataacacttt tggtaacaat      840
tttgtgattg gtaaatgtca aactatttat actgtttaa agtgttaagt ggttaccatt      900
caaaaccaaa accttaaaaa ttaaagccgt tatgctattt ttttaataaa gaagacatga      960
ttttgcccta tcaaattaaa attggtgtgt tgatgagtgc aaaagcgtag gcaaataaat     1020
cacacatcat taacaaaaaa aaaaaatcac acataaaagt gtaattgtga ggaaaaaaga     1080
tgtttccaat ttttaagtcc accaccaaac tggacccact aacccctact cagggtatac     1140
aattccattt ccacccatac acaattatag tagtccacct ttttctttt ctttctacac      1200 atatctggat tccagctttt aagtaggatt attattggtt ggtaaaagat gcaaagaata     1260
tgagaaaagg tctaattgcg tgctccataa acccttattc tagttcaacc ataattgtca     1320
gtcaatagaa gcaagataat ttgaacgtcc aagtcatcat catcttttt tttctttctg      1380 aaatttcgtt ttacaataaa caagaaaagg ttccgagtcc tcaagcatct ctcacgtcgg     1440
agcaagttgc catgcactct ccaaaataaa ataaaaaaca gacaaagact ttagacttgt     1500
gacttttcga cctcattatg tacttactta cttcatcttc tatttggcac ccacaaacag     1560
tagtttccac ttttcttcctc aataagttcc atttttggat tctttcctat ttttacacaa    1620
atttgttgta ttctaaaaag ttatatattc tatttgctgg gctttagata tgggctggct     1680
ctggatatgt gtgtaatgga tacatattag taaatagtta agtccaaaaa agaaattata     1740
```

-continued

```
aaccccctat gtagtttgaa aactgaatca tctgacaaaa cgagcaggga aggcccataa      1800
taaggcctaa taagtaaggt aagcccacag agaaatatac ttacgggctt ggatttccga      1860
accttcctaa aaagtgggac ctacgcggct gagaagaaag acgaaggcca tatcagaccg      1920
gcgataactg aaaagtcaaa agtcaaaatt caagaggaag aggagtttct aatcatgtct      1980
ctctctgttt tcttcttatt cttctatcaa accgtcaagt tgggaaacaa aacaaaactc      2040
gcaagtttaa caacgcgtct tctacctcct cctcatcgga ctatttatct atagtcttcg      2100
ttagatcaat tcctctgttt tactcctaag tttcgagatc cacatttctc tttaacctca      2160
tctcatctct tagtcgagat cttcactttc tgcatgacaa tagggtcgtt tttctcttct      2220
ctcttattct ggcgcaattc tcaggtaacc tcaatcgact attctctgtt ctactccctt      2280
ttttctttat cattttaaaa atcctaacat gaaaataaa gtagttaaat agagtcaacg       2340
aaaacattgt taatgaaaca gtggtgtgct tagcataacg aatcagacag acaaaaagtg      2400
tctggatccg tagagcaaag tgttgtcgtg tctttgacaa agttctttgt ttgcctaaac      2460
caatttgttc atccgataga atgaattgca ttccgttgtt actatcatcc aaaccggaga      2520
tgtcaagccc taaccctcaa gtagtatttc ttagagagcc attctttgtt tgtttagatc      2580
caattagaag aaggtttagt tgactgtgat gattgtttgt gttttggtg gcaggaccag        2640 gaggcgcaga gagggagg                                                    2658

<210> SEQ ID NO 18
<211> LENGTH: 1711
<212> TYPE: DNA
<213> ORGANISM: Arabidopsis thaliana
<220> FEATURE:
<221> NAME/KEY: CDS
<222> LOCATION: (522)..(1430)
<223> OTHER INFORMATION: coding for putative phosphatidic acid
      phosphatase

<400> SEQUENCE: 18
gatccacatt tctctttaac ctcatctcat ctcttagtcg agatcttcac tttctgatga       60
caatagggtc gttttttctct tctctcttat tctggcgcaa ttctcaggta acctcaatcg     120
actattctct gttctactcc ctttttttctt tatcatttta aaaatcctaa cattgaaaat      180
aaagtagtta aatagagtca acgaaaaacat tgttaatgaa acagtggtgt gcttagcata     240
acgaatcaga cagacaaaaa gtgtctggat ccgtagagca aagtgttgtc gtgtctttga      300
caaagttctt tgtttgccta aaccaatttg ttcatccgat agaatgaatt gcattccgtt       360
gttactatca tccaaaccgg agatgtcaag ccctaaccct caagtagtat ttcttagaga       420
gccattcttt gtttgtttag atccaattag aagaaggttt agttgactgt gatgattgtt       480 tgtgttttg gtggcaggac caggaggcgc agagagggag g atg cag gag ata gat        536
                                             Met Gln Glu Ile Asp
                                              1               5 ctt agt gtt cac act ata aag tcc cat gga gga aga gtc gct tct aaa        584
Leu Ser Val His Thr Ile Lys Ser His Gly Gly Arg Val Ala Ser Lys
             10                  15                  20 cac aag cac gat tgg atc ata ctc gtc atc ttg att gcc atc gag ata        632
His Lys His Asp Trp Ile Ile Leu Val Ile Leu Ile Ala Ile Glu Ile
         25                  30                  35 ggc ttg aac ctc atc tct cct ttc tac cgc tac gtg gga aaa gac atg        680
Gly Leu Asn Leu Ile Ser Pro Phe Tyr Arg Tyr Val Gly Lys Asp Met
     40                  45                  50 atg act gac ctc aag tac cct ttc aag gac aac acc gta cct atc tgg        728
Met Thr Asp Leu Lys Tyr Pro Phe Lys Asp Asn Thr Val Pro Ile Trp
```

```
              55                  60                  65
tct gtc cct gtg tac gct gtg ctt ctt ccc atc ata gtg ttc gtc tgc      776
Ser Val Pro Val Tyr Ala Val Leu Leu Pro Ile Ile Val Phe Val Cys
 70              75                  80                  85 ttc tac ctg aag agg aca tgt gtg tac gat ctg cac cac agc atc ctc      824
Phe Tyr Leu Lys Arg Thr Cys Val Tyr Asp Leu His His Ser Ile Leu
                 90                  95                 100 ggg ctg ctc ttc gcc gtc ttg ata act ggt gtc atc act gac tcc atc      872
Gly Leu Leu Phe Ala Val Leu Ile Thr Gly Val Ile Thr Asp Ser Ile
            105                 110                 115 aag gta gcc acc gga cgc cct cgt cct aac ttc tac tgg cgc tgc ttc      920
Lys Val Ala Thr Gly Arg Pro Arg Pro Asn Phe Tyr Trp Arg Cys Phe
        120                 125                 130 ccc gac ggc aaa gag ctg tat gat gcg ttg gga ggt gtg gta tgc cac      968
Pro Asp Gly Lys Glu Leu Tyr Asp Ala Leu Gly Gly Val Val Cys His
    135                 140                 145 ggc aag gca gct gag gtc aag gaa ggc cac aag agc ttc ccg agc gga     1016
Gly Lys Ala Ala Glu Val Lys Glu Gly His Lys Ser Phe Pro Ser Gly
150                 155                 160                 165 cac act tcc tgg tcc ttt gcg ggg ctt aca ttc ctt tcc ctt tac ctc     1064
His Thr Ser Trp Ser Phe Ala Gly Leu Thr Phe Leu Ser Leu Tyr Leu
                170                 175                 180 tct ggc aaa atc aag gcc ttc aac aat gaa gga cat gtg gcg aaa ctc     1112
Ser Gly Lys Ile Lys Ala Phe Asn Asn Glu Gly His Val Ala Lys Leu
            185                 190                 195 tgc ctc gtg atc ttc cct ctg ctt gcc gct tgt ctt gtg ggg ata tct     1160
Cys Leu Val Ile Phe Pro Leu Leu Ala Ala Cys Leu Val Gly Ile Ser
        200                 205                 210 cgt gtg gat gac tac tgg cac cac tgg caa gat gtc ttc gca gga gct     1208
Arg Val Asp Asp Tyr Trp His His Trp Gln Asp Val Phe Ala Gly Ala
    215                 220                 225 ctc att ggc acc ctt gta gcc gcc ttc tgc tac cgt cag ttc tac ccc     1256
Leu Ile Gly Thr Leu Val Ala Ala Phe Cys Tyr Arg Gln Phe Tyr Pro
230                 235                 240                 245 aac cct tac cac gaa gaa gga tgg ggt ccc tac gcc tat ttc aag gca     1304
Asn Pro Tyr His Glu Glu Gly Trp Gly Pro Tyr Ala Tyr Phe Lys Ala
                250                 255                 260 gct caa gaa cga gga gtc cct gtg acc tcc tcc caa aac gga gat gcc     1352
Ala Gln Glu Arg Gly Val Pro Val Thr Ser Ser Gln Asn Gly Asp Ala
            265                 270                 275 ttg agg gct atg tct ctg cag atg gat tca aca tct ctc gaa aac atg     1400
Leu Arg Ala Met Ser Leu Gln Met Asp Ser Thr Ser Leu Glu Asn Met
        280                 285                 290 gaa tct ggc act tcc acc gct ccc aga tga tcctcctctc ttattatttg       1450
Glu Ser Gly Thr Ser Thr Ala Pro Arg
    295                 300 attcattatt tggtttttca ttttgatttg gccgtcgtcg tgagattgtg aatggtgtag   1510
ctacatactg tatgtgtatt caaaactcta cttgtaccat tacattttg taaatccact    1570 cttcatgaaa ttgacgtttt tctggtgtcc gagaggcttg ggtcgctcga ataatctcgt   1630
ccaatagact aatacggctc tagtgaacac ggtatttaca tgtttgtgat ctaaactgaa   1690
atcagttatt tcttaattcg t                                             1711

<210> SEQ ID NO 19
<211> LENGTH: 302
<212> TYPE: PRT
<213> ORGANISM: Arabidopsis thaliana

<400> SEQUENCE: 19
```

```
Met Gln Glu Ile Asp Leu Ser Val His Thr Ile Lys Ser His Gly Gly
1               5                   10                  15

Arg Val Ala Ser Lys His Lys His Asp Trp Ile Ile Leu Val Ile Leu
            20                  25                  30

Ile Ala Ile Glu Ile Gly Leu Asn Leu Ile Ser Pro Phe Tyr Arg Tyr
        35                  40                  45

Val Gly Lys Asp Met Met Thr Asp Leu Lys Tyr Pro Phe Lys Asp Asn
50                  55                  60

Thr Val Pro Ile Trp Ser Val Pro Val Tyr Ala Val Leu Leu Pro Ile
65                  70                  75                  80

Ile Val Phe Val Cys Phe Tyr Leu Lys Arg Thr Cys Val Tyr Asp Leu
                85                  90                  95

His His Ser Ile Leu Gly Leu Leu Phe Ala Val Leu Ile Thr Gly Val
            100                 105                 110

Ile Thr Asp Ser Ile Lys Val Ala Thr Gly Arg Pro Arg Pro Asn Phe
        115                 120                 125

Tyr Trp Arg Cys Phe Pro Asp Gly Lys Glu Leu Tyr Asp Ala Leu Gly
130                 135                 140

Gly Val Val Cys His Gly Lys Ala Ala Glu Val Lys Glu Gly His Lys
145                 150                 155                 160

Ser Phe Pro Ser Gly His Thr Ser Trp Ser Phe Ala Gly Leu Thr Phe
                165                 170                 175

Leu Ser Leu Tyr Leu Ser Gly Lys Ile Lys Ala Phe Asn Asn Glu Gly
            180                 185                 190

His Val Ala Lys Leu Cys Leu Val Ile Phe Pro Leu Leu Ala Ala Cys
        195                 200                 205

Leu Val Gly Ile Ser Arg Val Asp Asp Tyr Trp His His Trp Gln Asp
    210                 215                 220

Val Phe Ala Gly Ala Leu Ile Gly Thr Leu Val Ala Ala Phe Cys Tyr
225                 230                 235                 240

Arg Gln Phe Tyr Pro Asn Pro Tyr His Glu Glu Gly Trp Gly Pro Tyr
                245                 250                 255

Ala Tyr Phe Lys Ala Ala Gln Glu Arg Gly Val Pro Val Thr Ser Ser
            260                 265                 270

Gln Asn Gly Asp Ala Leu Arg Ala Met Ser Leu Gln Met Asp Ser Thr
        275                 280                 285

Ser Leu Glu Asn Met Glu Ser Gly Thr Ser Thr Ala Pro Arg
    290                 295                 300
```

<210> SEQ ID NO 20
<211> LENGTH: 2219
<212> TYPE: DNA
<213> ORGANISM: Arabidopsis thaliana
<220> FEATURE:
<221> NAME/KEY: promoter
<222> LOCATION: (1)..(2219)
<223> OTHER INFORMATION: transcription regulating sequence from
      Arabidopsis thaliana gene At3g45560

<400> SEQUENCE: 20
attataactc tatgttgcat tacatggttg cttggtagat gcgggtacga gttttgctac      60
atatgaggag ccaaatggat cactggaaga gtttgcactc attcaacaac taatccgcca     120
gatactcctt caacaactgt gtcgacatgt gtttgcgtct ttagttttct tacccttttgg    180 gtagttttaa ttctttggga cgtttattgt tatcaacatt tctatcggtg atcaacatcg     240

```
tgacgcttat cggaaactcg agaggattgg taacgatgag catgcaagtg aagctaggat    300
gacaaaatca tatcctagtc atttccatct ttgacataaa aagatgaaaa ctttggttta    360
attattatga taagacttga aattttattt tgcttttgat gttttgtttt tgatcgtcgt    420
actacaattt tttcttgcct cgattataca aaaacgttac aacctaaaac tttattataa    480
atttttttat caaaactaca aatcgagaat cgtacgtaat accaacaaat catgttctgg    540
ttttcgcgat caagttctgg acgagtggat catcctctct tttcacttga ccattgatat    600
aaagaaccaa atgtttgtgc aacgcttcca gttagccgaa caccgcaacg ggaacacacc    660
cttaaccggc cattcctgct gacggactga acaagagcag cacgaaatca tcaactctga    720
aattgtaaaa gaatatatgt gattagttgc ctctaatatt cttttacct tactaattag    780 atatagttgt cataataata tatgcatatt cttctatcca aattttggta ttttataaga    840
tatctacgta tcgctaatta ataatgggtt cccaaacgat tccaaatttt gcaagtgata    900
tgtttatttg aaattggatg ccgaaagaat gtcttgatca tcaaatgctt ctggttttc    960 ttttatatga ccactaagac tcaatcccat agggttttct tgatgggtag ttaacaactc   1020
catcttaacc attggtcgga tggttctagt tgacgaaacc gatccaattc aatctgaaca   1080
caatggtgaa acccaaatgg catgcatgtt caaacctctc caattgatta ttgagtgaaa   1140
gctaattcat catgtgtttt ttttctatgt cgaaagttca tattctgtat ttatatcttc   1200
tttgttgatg gggaatatac attttgcag tcattttgtg aaataaatcc tcaacttggg   1260
acttatttat agtggctgtc actgatattt aataattgtt tttgataatt agaaagtaaa   1320
tctacaaatt aaatgtttgc atttaactac cttcccaaaa tctctccgca ttaattatac   1380
gattagttat taaataaaa cttccaaaat atttaatatc atttaaacac tacaaaatta   1440 tcattttga tattgctttt tttttatgac tataacaatt cgattataag aagcaaaccg   1500
tagagatatt tgatagcaat taattactac aaaattacaa atattaagaa caatgattca   1560
taaacatatc ataaataaaa ttagtattaa taaaataaat agattttttt acgggacggg   1620
ttggcgggac gggtttggca ggacgttact taataacaat tgtaaactat aaaacaaaaa   1680
tattttatag atagatacaa tttgcaaact tttatatata ctaactttaa gaaaataaat   1740
tgtctccaca gtatccgcgg gttaaagtct agtaaactaa aaacacaagc taaatagaaa   1800
gtttaagttg taacacatca ttggtcatgg tttcttatat aaatattaag tgtgcaaaaa   1860
agaaactgct atttaacaa gttctgtcag acgttccagt tcaacgtaga tcaaataaag   1920
tctattaatt aggaatttta ttttctagg tccttgtagg ccaaaaaaac aagctccacc   1980
acgaaaagct ctttcacaaa attgcaacat gatgaagata ttcttataag aacgaacaca   2040
tgggcatggg ttctaacgga taatgatagg ttccctaaat tttagggatg ttctaaaata   2100
tacaaaatat atattatttg gaactcacga acggcctaac cctaaagccc taaaattttg   2160
gcttctatat atatatggga ggaatcttca tagacaactc gcaatatata tctagactc    2219
```

<210> SEQ ID NO 21
<211> LENGTH: 2218
<212> TYPE: DNA
<213> ORGANISM: Arabidopsis thaliana
<220> FEATURE:
<221> NAME/KEY: promoter
<222> LOCATION: (1)..(2218)
<223> OTHER INFORMATION: transcription regulating sequence from
      Arabidopsis thaliana gene At3g45560

<400> SEQUENCE: 21

-continued

```
attataactc tatgttgcat tacatggttg cttggtagat gcgggtacga gttttgctac    60
atatgtggag ccaaatggat cactggaaga gtttgcactc attcaacaac taatccgcca   120
gatactcctt caacaactgt gtcgacatgt gtttgcgtct ttagttttct tacctttggg   180
gtagttttaa ttctttggga cgtttattgt tatcaacatt tctatcggtg atcaacatcg   240
tgacgcttat cggaaactcg agaggattgg taacgatgag catgcaagtg aagctaggat   300
gacaaaatca tatcctagtc atttccatct ttgacataaa aagatgaaaa ctttggttta   360
attattatga taagatttga aatttttattt tgcttttgat gttttgtttt tgatcgtcgt   420
actacaattt tttcttgtct cgattataca aaaacgttac aacctaaaac tttattataa   480
attttttttat caaaactaca aatcgagaat cgtacgtaat accaacaaat catgttctgg   540
ttttcgcgat caagttctgg acgagtggat catcctctct tttcacttga ccattgatat   600
aaagaaccaa atgtttgtgc aacgcttcca gttagccgaa caccgcaacg ggaacacacc   660
cttaaccggc cattcctgct gacggactga acaagagcag cacgaaatca tcaactctga   720
aattgtaaaa gaatatatgt gattagttgc ctctaatatt cttttttaccct tactaattag   780
atatagttgt cataataata tatgcatatt cttctatcca aatttttggta tttttataaaa   840
tatctacgta tcgctaatta ataatggttt cccaaacgat tccaaattttt gcaagtgata   900
tgtttatttg aaattggatg ccgaaagaat gtcttgatca tcaaatgctt ctggtttttc    960
ttttatatga ccactaagac tcaatcccat agggttttct tgatgggtag ttaacaactc   1020
catcttaacc attggtcgga tggttctagt tgacgaaacc gatccaattc aatctgaaca   1080
caatggtgaa acccaaatgg catgcatgtt caaacctctc caattgatta ttgagtgaaa   1140
gctaattcat catgtgtttt ttttctatgt cgaaagttca tattctgtat ttatatcttc   1200
tttgttgatg gggaatatac attttttgcag tcattttgtg aaataaatcc tcaacttggg   1260
acttatttat agtggctgtc actgatattt aataattgtt tttgataatt agaaagtaaa   1320
tctacaaatt aaatgtttgc atttaactac cttcccaaaa tctctccgca ttaattatac   1380
gattagttat taaaataaaa cttccaaaat atttaatatc atttaaacac tacaaaatta   1440
tcattttttga tattgctttt ttttttatgac tataacaatt cgattataag aagcaaaccg   1500
tagagatatt tgatagcaat taattactac aaaattacaa aatattaaga caatgattca   1560
taaacatatc ataaataaaa ttagtattaa taaaataaat agatttttttt acgggacggg   1620
ttggcgggac gggtttggca ggacgttact taataacaat tgtaaactat aaaacaaaaa   1680
tattttatag atagatacaa tttgcaaact tttatatata ctaactttaa gaaaataaat   1740
tgtctccaca gtatccgcgg gttaaagtct agtaaactaa aaacacaagc taaatagaaa   1800
gtttaagttg taacacatca ttggtcatgg tttcttatat aaatattaag tgtgcaaaaa   1860
agaaactgct attttaacaa gttctgtcag acgttccagt tcaacgtaga tcaaataaag   1920
tctattaatt aggaattttta ttttttctagg tccttgtagg ccaaaaaaac aagctccacc   1980
acgaaaagct ctttcacaaa attgcaacat gatgaagata ttcttataag aacgaacaca   2040
tgggcatggt ttctaacgga taatgatagg ttccctaaat tttagggatg ttctaaaata   2100
tacaaaatat atattatttg gaactcacga acggcctaac cctaaagccc taaaattttg   2160
gcttctatat atatatggga ggaatcttca tagacaactc gcaatatata tctagact    2218
```

<210> SEQ ID NO 22
<211> LENGTH: 1512
<212> TYPE: DNA
<213> ORGANISM: Arabidopsis thaliana

```
<220> FEATURE:
<221> NAME/KEY: CDS
<222> LOCATION: (1)..(1512)
<223> OTHER INFORMATION: coding for zinc finger (C3HC4-type RING finger)
      family

<400> SEQUENCE: 22 atg tat gac cta aaa ccc tca ccg ttc cac atg aat agg ctt tac ttc       48
Met Tyr Asp Leu Lys Pro Ser Pro Phe His Met Asn Arg Leu Tyr Phe
1               5                  10                  15 aag ggt ttt gtg agc gag gaa act aag ggc ttt ggg gtt gct att tgc       96
Lys Gly Phe Val Ser Glu Glu Thr Lys Gly Phe Gly Val Ala Ile Cys
            20                  25                  30 gac caa gag gat aag cta ctg tat cat atc aag ggt tca cgt cat cat      144
Asp Gln Glu Asp Lys Leu Leu Tyr His Ile Lys Gly Ser Arg His His
        35                  40                  45 gac tct gcc ata aca gtt ttg gag gct gag ctt acc gca ttg aag cga      192
Asp Ser Ala Ile Thr Val Leu Glu Ala Glu Leu Thr Ala Leu Lys Arg
50                  55                  60 gga cta atc gaa gct gtg ggt ttg ggg atc aac cat atc tca ttc tac      240
Gly Leu Ile Glu Ala Val Gly Leu Gly Ile Asn His Ile Ser Phe Tyr
65                  70                  75                  80 tgc gat cat gat cag att ttc gaa ttg gtc atg ggg ata tcg gtc cca      288
Cys Asp His Asp Gln Ile Phe Glu Leu Val Met Gly Ile Ser Val Pro
                85                  90                  95 gag caa gat aac att gct ttg ctt atg gat gat gtg caa cgt att aga      336
Glu Gln Asp Asn Ile Ala Leu Leu Met Asp Asp Val Gln Arg Ile Arg
            100                 105                 110 aaa caa ttt act tct agc atc cct gtt ttg atg act aga aat caa gct      384
Lys Gln Phe Thr Ser Ser Ile Pro Val Leu Met Thr Arg Asn Gln Ala
        115                 120                 125 aag ttt gct tat aag ctt gca atg gaa aca ata gtt tct gaa att agc      432
Lys Phe Ala Tyr Lys Leu Ala Met Glu Thr Ile Val Ser Glu Ile Ser
    130                 135                 140 ata gat atg gcg cct tct cag agg aag act tgc ggt atc tgt ttc aat      480
Ile Asp Met Ala Pro Ser Gln Arg Lys Thr Cys Gly Ile Cys Phe Asn
145                 150                 155                 160 gat gat ttc aaa gct gag cat atg ttt tct gtt gat tta tgt ggc cat      528
Asp Asp Phe Lys Ala Glu His Met Phe Ser Val Asp Leu Cys Gly His
                165                 170                 175 caa ttc tgt gtg gag tgc atg aca caa tat ata aaa gtg agg cta ctc      576
Gln Phe Cys Val Glu Cys Met Thr Gln Tyr Ile Lys Val Arg Leu Leu
            180                 185                 190 gag gaa agt gag atg aga tgc cct cat tat caa tgc gag tcc aag tta      624
Glu Glu Ser Glu Met Arg Cys Pro His Tyr Gln Cys Glu Ser Lys Leu
        195                 200                 205 act gtt gta cga tgt gcc aat ctt ttg act ccg gaa cta aga gag atg      672
Thr Val Val Arg Cys Ala Asn Leu Leu Thr Pro Glu Leu Arg Glu Met
    210                 215                 220 tgg gaa cat agg agc caa aag gaa tcc gtt gtt gtg gca gac aaa gct      720
Trp Glu His Arg Ser Gln Lys Glu Ser Val Val Val Ala Asp Lys Ala
225                 230                 235                 240 tat tgc caa atc gaa tgt gct tgg ctt tta tgt caa atg gag ttc aga      768
Tyr Cys Gln Ile Glu Cys Ala Trp Leu Leu Cys Gln Met Glu Phe Arg
                245                 250                 255 gat ggt gct tta gat gta gta agt ctt att gca tca gct gca aag ttc      816
Asp Gly Ala Leu Asp Val Val Ser Leu Ile Ala Ser Ala Ala Lys Phe
            260                 265                 270 cgt ggc ata aca act tgt cgt gcg agc aat aca aga gat gcg gat ata      864
Arg Gly Ile Thr Thr Cys Arg Ala Ser Asn Thr Arg Asp Ala Asp Ile
        275                 280                 285
```

```
agt ttt gct aca cat gtg gag atg aat gga agc aag gaa gtt gcc ttc       912
Ser Phe Ala Thr His Val Glu Met Asn Gly Ser Lys Glu Val Ala Phe
290                 295                 300 atc agc gaa agg aga tgc ttg tgg agt atg gct tta ctt caa ggg ttt       960
Ile Ser Glu Arg Arg Cys Leu Trp Ser Met Ala Leu Leu Gln Gly Phe
305                 310                 315                 320 agt gag cgg gga aca acg gga ttt gcg gtt gca att tgt gac caa gag      1008
Ser Glu Arg Gly Thr Thr Gly Phe Ala Val Ala Ile Cys Asp Gln Glu
            325                 330                 335 aat aag cta ctg tat cat acc aag ggt tca ctt cat cat gac tcc acc      1056
Asn Lys Leu Leu Tyr His Thr Lys Gly Ser Leu His His Asp Ser Thr
        340                 345                 350 att aca att ttg gag gct gag ctt acg tcc tta aaa caa gga cta acc      1104
Ile Thr Ile Leu Glu Ala Glu Leu Thr Ser Leu Lys Gln Gly Leu Thr
    355                 360                 365 gaa gct gtg aga ttg ggg ata act tat atc aaa att tac tgc gat cat      1152
Glu Ala Val Arg Leu Gly Ile Thr Tyr Ile Lys Ile Tyr Cys Asp His
370                 375                 380 act aaa ctt ttc gat ttg gtc atg ggg aca tcc gcg ctt gag gat aac      1200
Thr Lys Leu Phe Asp Leu Val Met Gly Thr Ser Ala Leu Glu Asp Asn
385                 390                 395                 400 att gcc ttg cta atg gat gat gtg cat cgc atc cga aaa caa ttg aag      1248
Ile Ala Leu Leu Met Asp Asp Val His Arg Ile Arg Lys Gln Leu Lys
            405                 410                 415 tct agc aat cct att ctg gag act aga act caa att agt atg ctt ata      1296
Ser Ser Asn Pro Ile Leu Glu Thr Arg Thr Gln Ile Ser Met Leu Ile
        420                 425                 430 aac ttg caa tgg aaa cca act gag ctt aat gga gtc atc aag cgc gcc      1344
Asn Leu Gln Trp Lys Pro Thr Glu Leu Asn Gly Val Ile Lys Arg Ala
    435                 440                 445 ccg agc cgg tac ata ccg ttt gcc ccg aag cca cct ctc aaa cga cca      1392
Pro Ser Arg Tyr Ile Pro Phe Ala Pro Lys Pro Pro Leu Lys Arg Pro
450                 455                 460 ccg agc cgt gaa aaa cac gcg agg caa aga ctt gta aaa acc att cat      1440
Pro Ser Arg Glu Lys His Ala Arg Gln Arg Leu Val Lys Thr Ile His
465                 470                 475                 480 tct cca agg atc att tcc ggt aaa ata gga tct ttt atg gga ctt tcg      1488
Ser Pro Arg Ile Ile Ser Gly Lys Ile Gly Ser Phe Met Gly Leu Ser
            485                 490                 495 gaa atg ata aag gag aat ctt tga                                      1512
Glu Met Ile Lys Glu Asn Leu
            500

<210> SEQ ID NO 23
<211> LENGTH: 503
<212> TYPE: PRT
<213> ORGANISM: Arabidopsis thaliana

<400> SEQUENCE: 23

Met Tyr Asp Leu Lys Pro Ser Pro Phe His Met Asn Arg Leu Tyr Phe
1               5                   10                  15

Lys Gly Phe Val Ser Glu Glu Thr Lys Gly Phe Gly Val Ala Ile Cys
            20                  25                  30

Asp Gln Glu Asp Lys Leu Leu Tyr His Ile Lys Gly Ser Arg His His
        35                  40                  45

Asp Ser Ala Ile Thr Val Leu Glu Ala Glu Leu Thr Ala Leu Lys Arg
    50                  55                  60

Gly Leu Ile Glu Ala Val Gly Leu Gly Ile Asn His Ile Ser Phe Tyr
65                  70                  75                  80
```

-continued

```
Cys Asp His Asp Gln Ile Phe Glu Leu Val Met Gly Ile Ser Val Pro
                 85                  90                  95

Glu Gln Asp Asn Ile Ala Leu Leu Met Asp Asp Val Gln Arg Ile Arg
                100                 105                 110

Lys Gln Phe Thr Ser Ser Ile Pro Val Leu Met Thr Arg Asn Gln Ala
            115                 120                 125

Lys Phe Ala Tyr Lys Leu Ala Met Glu Thr Ile Val Ser Glu Ile Ser
130                 135                 140

Ile Asp Met Ala Pro Ser Gln Arg Lys Thr Cys Gly Ile Cys Phe Asn
145                 150                 155                 160

Asp Asp Phe Lys Ala Glu His Met Phe Ser Val Asp Leu Cys Gly His
                165                 170                 175

Gln Phe Cys Val Glu Cys Met Thr Gln Tyr Ile Lys Val Arg Leu Leu
            180                 185                 190

Glu Glu Ser Glu Met Arg Cys Pro His Tyr Gln Cys Glu Ser Lys Leu
            195                 200                 205

Thr Val Val Arg Cys Ala Asn Leu Leu Thr Pro Glu Leu Arg Glu Met
    210                 215                 220

Trp Glu His Arg Ser Gln Lys Glu Ser Val Val Ala Asp Lys Ala
225                 230                 235                 240

Tyr Cys Gln Ile Glu Cys Ala Trp Leu Leu Cys Gln Met Glu Phe Arg
                245                 250                 255

Asp Gly Ala Leu Asp Val Val Ser Leu Ile Ala Ser Ala Ala Lys Phe
                260                 265                 270

Arg Gly Ile Thr Thr Cys Arg Ala Ser Asn Thr Arg Asp Ala Asp Ile
            275                 280                 285

Ser Phe Ala Thr His Val Glu Met Asn Gly Ser Lys Glu Val Ala Phe
            290                 295                 300

Ile Ser Glu Arg Arg Cys Leu Trp Ser Met Ala Leu Leu Gln Gly Phe
305                 310                 315                 320

Ser Glu Arg Gly Thr Thr Gly Phe Ala Val Ala Ile Cys Asp Gln Glu
                325                 330                 335

Asn Lys Leu Leu Tyr His Thr Lys Gly Ser Leu His His Asp Ser Thr
                340                 345                 350

Ile Thr Ile Leu Glu Ala Glu Leu Thr Ser Leu Lys Gln Gly Leu Thr
            355                 360                 365

Glu Ala Val Arg Leu Gly Ile Thr Tyr Ile Lys Ile Tyr Cys Asp His
    370                 375                 380

Thr Lys Leu Phe Asp Leu Val Met Gly Thr Ser Ala Leu Glu Asp Asn
385                 390                 395                 400

Ile Ala Leu Leu Met Asp Asp Val His Arg Ile Arg Lys Gln Leu Lys
                405                 410                 415

Ser Ser Asn Pro Ile Leu Glu Thr Arg Thr Gln Ile Ser Met Leu Ile
                420                 425                 430

Asn Leu Gln Trp Lys Pro Thr Glu Leu Asn Gly Val Ile Lys Arg Ala
            435                 440                 445

Pro Ser Arg Tyr Ile Pro Phe Ala Pro Lys Pro Leu Lys Arg Pro
    450                 455                 460

Pro Ser Arg Glu Lys His Ala Arg Gln Arg Leu Val Lys Thr Ile His
465                 470                 475                 480

Ser Pro Arg Ile Ile Ser Gly Lys Ile Gly Ser Phe Met Gly Leu Ser
                485                 490                 495
```

Glu Met Ile Lys Glu Asn Leu
            500

<210> SEQ ID NO 24
<211> LENGTH: 2042
<212> TYPE: DNA
<213> ORGANISM: Arabidopsis thaliana
<220> FEATURE:
<221> NAME/KEY: promoter
<222> LOCATION: (1)..(2042)
<223> OTHER INFORMATION: transcription regulating sequence from
      Arabidopsis thaliana gene At4g00580

<400> SEQUENCE: 24

```
cttcttctta cgtttccagt gtgaattgga tttgtgttct cctcctcttc tccagtagaa      60
gaagctgtgt ctgaggaaga gggaagatgt ctttaagaac agctgcccga agaatagtaa    120
aagggtcaga caataaataa agctttccaa ttttctaaaa ttgtaaagaa gaaataattc    180
ttttattcaa aagtcaataa atacaaggaa acaaaaactg aagttgcccg aaggaaaacg    240
ggcaaagagg gtataaaagt aaatgtggat atatagatcg ccacgtggac ggttgtgaat    300
catttttccag gcatattggt gatgagacta gaggtcaaag gatattggct aactcaccgt    360
tagatcaatg acacgtgtat ccgcgttctg gtgtttccgc ttttacccat gcgtgtgcct    420
ctggtaacaa atattacgtc ttcctaaaat aaaaaaagta ccaagtagag aaattagaga    480
aaaggaaagg taatatataa atttgagatt cgagtgtttt aagtgtaaac cattctttta    540
caaaaaaata ttcgctgcgg cgacttgaca ccgtcagctt ttaactctta aacagtgctt    600
ttttttttcc taccattcat tcatgtcaag atttcgaatc ctataaattt gatcacagca    660
aaattaaaca tagttaaggg caagggaaaa aaaaagaat gcatgcattt atttatttat    720
tttgacataa agaaaacatt caagatgtgt tggtatttca taatcaaata ctactaacaa    780
ataactataa tcttaattgt cttttgtcgg ccaataaact cgatccaaaa ttctttgtcg    840
atccaaatag gtaaaaaga aactcgaata aaaattcata tacgatatga aaatattac     900
gtacgtagtc tgaactctaa acaaaaatat tagtatttt ctttacatt gagaaagatc    960
ttgactatgg ttaattctat ttttggaaat agagaaatct atatatgtat ggttcttagt  1020
gttttaataa ataaatattt ggtgtttcta actccatcag caacttcttc acaggcccag  1080
gtaattctct aatacactct gatgtttgat cttagaacct gttcaagtac atgaaataga  1140
actatgtatg actttgtttg ccttgtctac tttcttgta ccttaaacac tgaagacatc   1200
tgtgacttat cttcaacatc tcctcactgt tttgaatttc ttaaaccttg cagcaatgca  1260
gctcaacaag aacaatcttt cgaaccctgt cttgatgtct atacgactgc aaaaaaccgc  1320
tcaggtaact tgtaactaca aaacacacgt agttgtcagt ttctcaattt cccacttgag  1380
cttaaaccag aaaactaaac cgttttcttt gcttgtctga ggcacccatt gatcccgagc  1440
ttctccctgc aacttcattt tagctcatga agagaaaacc ataaacttca cttcacttta  1500
gatcaatgat tctacaccgg cattacttgg agctgtttct tcaatgattc tacaccaggt  1560
acttgtcttt tgaaaattta tggttctttg cttgagatag acttgcatct ctcttgataa  1620
aatccatctg ctccaaccca ttgtcctgtg aaaagcccct agctaacttc ctcgccttat  1680
agctttgctt ttcaacaatt cctagtattc ctggttccct tagagaatct ctgtcttcat  1740
ataacgtgag gcccactcat ttggcccata gagaaagaag ttatgatctg gtcaaaccct  1800
ttcaatgagt cataaaccaa aagagagaag acgaaaggac gatgaaaaga gagaatcgac  1860
ctacacgttg tgttttccca agtaattaag cgttttttgat ttcccaaaaa aaacataaag  1920
```

```
cttttcatat tcctctacga aagaaactcg cttataaata tcaaacagag agagtggagt    1980
ttcattttct tctcaacttc atcaaaaccc tattttgcat ttctcttaca ataatcttac    2040
tg                                                                   2042

<210> SEQ ID NO 25
<211> LENGTH: 2044
<212> TYPE: DNA
<213> ORGANISM: Arabidopsis thaliana
<220> FEATURE:
<221> NAME/KEY: promoter
<222> LOCATION: (1)..(2044)
<223> OTHER INFORMATION: transcription regulating sequence from
      Arabidopsis thaliana gene At4g00580

<400> SEQUENCE: 25
cttcttctta cgtttccagt gtgaattgga tttgtgttct cctcctcttc tccagtagaa      60
gaagctgtgt ctgaggaaga gggaagatgt ctttaagaac agctgcccga agaatagtaa     120
aagggtcaga caataaataa agctttccaa ttttctaaaa ttgtaaagaa gaaataattc     180
ttttattcaa aagtcaataa atacaaggaa acaaaaactg aagttgcccg aaggaaaacg     240
ggcaaagagg gtataaaagt aaatgtggat atatagatcg ccacgtggac ggttgtgaat     300
cattttccag gcatattggt gatgagacta gaggtcaaag gatattggct aactcaccgt     360
tagatcaatg acacgtgtat ccgcgttctg gtgtttccgc ttttacccat gcgtgtgcct     420
ctggtaacaa atattcgtc ttcctaaaat aaaaaaagta ccaagtagag aaattagaga     480
aaaggaaagg taatatataa atttgagatt cgagtgtttt aagtgtaaac cattctttta     540
caaaaaaata ttcgctgcgg cgacttgaca ccgtcagctt ttaactctta aacagtgctt     600
tttttttttt cctaccattc attcatgtca agatttcgaa tcctataaat ttgatcacag     660
caaaattaaa catagttaag ggcaagggaa aaaaaaaaga atgcatgcat ttatttattt     720
attttgacat aaagaaaaca ttcaagatgt gttggtattt cataatcaaa tactactaac     780
aaataactat aatcttaatt gtcttttgtc ggccaataaa ctcgatccaa aattctttgt     840
cgatccaaat aggtaaaaaa gaaactcgaa taaaaattca tatacgatat gaaaaatatt     900
acgtacgtag tctgaactct aaacaaaaat attagtattt tcttttaca ttgagaaaga     960 tcttgactat ggttaattct attttggaa atagagaaat ctatatatgt atggttctta    1020 gtgtttaat aaataaatat ttggtgtttc taactccatc agcaacttct tcacaggccc    1080
aggtaattct ctaatacact ctgatgtttg atcttagaac ctgttcaagt acatgaaata    1140
gaactatgta tgactttgtt tgccttgtct actttctttg taccttaaac attgaagaca    1200
tctgtgactt atcttcaaca tctcctcact gttttgaatt tcttaaacct tgcagcaatg    1260
cagctcaaca agaacaatct ttcgaaccct gtcttgatgt ctatacgact gcaaaaaacc    1320
gctcaggtaa cttgtaacta caaaacacac gtagttgtca gtttctcaat ttcccacttg    1380
agcttaaacc agaaaactaa accgtttttct ttgcttgtct gaggcaccca ttgatcccga    1440
gcttctccct gcaacttcat tttagctcat gaagagaaaa ccataaactt cacttcactt    1500
tagatcaatg attctacacc ggcattactt ggagctgttt cttcaatgat tctacaccag    1560
gtacttgtct tttgaaaatt tatggttctt tgcttgagat agacttgcat ctctcttgat    1620
aaaatccatc tgctccaacc cattgtcctg tgaaaagccc ttagctaact tcctcgcctt    1680
atagctttgc ttttcaacaa ttcctagtat tcctggtttc cttagagaat ctctgtcttc    1740
atataacgtg aggcccactt atttggccca tagagaaaga agttatgatc tggtcaaacc    1800
```

-continued

```
ctttcaatga gtcataaacc aaaagagaga agacgaaagg acgatgaaaa gagagaatcg    1860
acctacacgt tgtgttttcc caagtaatta agcgttttg  atttcccaaa aaaaacataa    1920
agcttttcat attcctctac gaaagaaact cgcttataaa tatcaaacag agagagtgga    1980
gtttcatttt cttctcaact tcatcaaaac cctatttgc  atttctctta caataatctt    2040
actg                                                                 2044
```

<210> SEQ ID NO 26
<211> LENGTH: 954
<212> TYPE: DNA
<213> ORGANISM: Arabidopsis thaliana
<220> FEATURE:
<221> NAME/KEY: CDS
<222> LOCATION: (1)..(954)
<223> OTHER INFORMATION: coding for COP1-interacting protein-related protein

<400> SEQUENCE: 26

```
atg gct gat tcc ggt tcg caa tgt gtc ttt gtg aag act agt att gat      48
Met Ala Asp Ser Gly Ser Gln Cys Val Phe Val Lys Thr Ser Ile Asp
1               5                   10                  15 acc cgt ttg ggg cta ctc ctt gac agt cat gat agc gtg tct tct ttc      96
Thr Arg Leu Gly Leu Leu Leu Asp Ser His Asp Ser Val Ser Ser Phe
            20                  25                  30 aaa gac aaa ttc tgc aaa gaa cac gaa ctg tgt ttt cca agt gtt ggc     144
Lys Asp Lys Phe Cys Lys Glu His Glu Leu Cys Phe Pro Ser Val Gly
        35                  40                  45 aac atc act gtt tct gcc ttg aag gtt aac gtg agt ggt aat gat tat     192
Asn Ile Thr Val Ser Ala Leu Lys Val Asn Val Ser Gly Asn Asp Tyr
    50                  55                  60 cac ttg tcc gat tct atg ata ttg aaa aaa gct ctt caa ggc ctc agt     240
His Leu Ser Asp Ser Met Ile Leu Lys Lys Ala Leu Gln Gly Leu Ser
65                  70                  75                  80 aac gag gac ttt ttt cta tcc gtt gac ctc gta cgt gtc cag gag aaa     288
Asn Glu Asp Phe Phe Leu Ser Val Asp Leu Val Arg Val Gln Glu Lys
                85                  90                  95 agt gag ctg cag att ggt gaa gca gtt gag aaa aaa acg agg aag aga     336
Ser Glu Leu Gln Ile Gly Glu Ala Val Glu Lys Lys Thr Arg Lys Arg
            100                 105                 110 aaa tcg aaa agt gcc aac aat agt aga aag aaa ctc tcc ata gag acg     384
Lys Ser Lys Ser Ala Asn Asn Ser Arg Lys Lys Leu Ser Ile Glu Thr
        115                 120                 125 cca acg gaa gca aaa ggc ctt gaa agt ggt gag gga act gtc act agg     432
Pro Thr Glu Ala Lys Gly Leu Glu Ser Gly Glu Gly Thr Val Thr Arg
    130                 135                 140 ttg gaa gag aat cag aat att tgt gat gta gat caa gag gaa cct gtc     480
Leu Glu Glu Asn Gln Asn Ile Cys Asp Val Asp Gln Glu Glu Pro Val
145                 150                 155                 160 gat ggt cat acc ata gat gtt gag gcc aag att gat ctt tca ggg aca     528
Asp Gly His Thr Ile Asp Val Glu Ala Lys Ile Asp Leu Ser Gly Thr
                165                 170                 175 atc gaa caa gac gac gtt caa aag gag gta gca aat gct gat tta aac     576
Ile Glu Gln Asp Asp Val Gln Lys Glu Val Ala Asn Ala Asp Leu Asn
            180                 185                 190 atg att gac caa gac aag gat ctt gaa aat gat aat ctt cta gct gaa     624
Met Ile Asp Gln Asp Lys Asp Leu Glu Asn Asp Asn Leu Leu Ala Glu
        195                 200                 205 tta aac caa act agt gat gat gct gag aaa gaa ggg atc ata ggt ctt     672
Leu Asn Gln Thr Ser Asp Asp Ala Glu Lys Glu Gly Ile Ile Gly Leu
    210                 215                 220
```

```
gtt aat gct act tct gaa gct att gaa aac gaa act gag atg agt gtc      720
Val Asn Ala Thr Ser Glu Ala Ile Glu Asn Glu Thr Glu Met Ser Val
225             230                 235                 240 aag gaa aaa gat ggt gat gag gag gct aaa tct gag aag cct aaa aag      768
Lys Glu Lys Asp Gly Asp Glu Glu Ala Lys Ser Glu Lys Pro Lys Lys
                245                 250                 255 aaa aat aga gca aag aaa gtc aag act ccg act aaa gaa gat ggt cta      816
Lys Asn Arg Ala Lys Lys Val Lys Thr Pro Thr Lys Glu Asp Gly Leu
            260                 265                 270 gtt gct tct agc tca agg aac gct gag gaa gat ggt gtc tcg aga gat      864
Val Ala Ser Ser Ser Arg Asn Ala Glu Glu Asp Gly Val Ser Arg Asp
        275                 280                 285 ccg cag gag aat gtg gct aaa gtt gtg aag aag ccg aac aag aga tcg      912
Pro Gln Glu Asn Val Ala Lys Val Val Lys Lys Pro Asn Lys Arg Ser
    290                 295                 300 aag aag gaa cag tct tca aac att gtt gag gag gat gct taa              954
Lys Lys Glu Gln Ser Ser Asn Ile Val Glu Glu Asp Ala
305                 310                 315
```

<210> SEQ ID NO 27
<211> LENGTH: 317
<212> TYPE: PRT
<213> ORGANISM: Arabidopsis thaliana

<400> SEQUENCE: 27

```
Met Ala Asp Ser Gly Ser Gln Cys Val Phe Val Lys Thr Ser Ile Asp
1               5                   10                  15

Thr Arg Leu Gly Leu Leu Asp Ser His Asp Ser Val Ser Ser Phe
                20                  25                  30

Lys Asp Lys Phe Cys Lys Glu His Glu Leu Cys Phe Pro Ser Val Gly
            35                  40                  45

Asn Ile Thr Val Ser Ala Leu Lys Val Asn Val Ser Gly Asn Asp Tyr
        50                  55                  60

His Leu Ser Asp Ser Met Ile Leu Lys Lys Ala Leu Gln Gly Leu Ser
65                  70                  75                  80

Asn Glu Asp Phe Phe Leu Ser Val Asp Leu Val Arg Val Gln Glu Lys
                85                  90                  95

Ser Glu Leu Gln Ile Gly Glu Ala Val Glu Lys Lys Thr Arg Lys Arg
            100                 105                 110

Lys Ser Lys Ser Ala Asn Asn Ser Arg Lys Lys Leu Ser Ile Glu Thr
        115                 120                 125

Pro Thr Glu Ala Lys Gly Leu Glu Ser Gly Glu Gly Thr Val Thr Arg
    130                 135                 140

Leu Glu Glu Asn Gln Asn Ile Cys Asp Val Asp Gln Glu Glu Pro Val
145                 150                 155                 160

Asp Gly His Thr Ile Asp Val Glu Ala Lys Ile Asp Leu Ser Gly Thr
                165                 170                 175

Ile Glu Gln Asp Asp Val Gln Lys Glu Val Ala Asn Ala Asp Leu Asn
            180                 185                 190

Met Ile Asp Gln Asp Lys Asp Leu Glu Asn Asp Asn Leu Leu Ala Glu
        195                 200                 205

Leu Asn Gln Thr Ser Asp Ala Glu Lys Glu Gly Ile Ile Gly Leu
    210                 215                 220

Val Asn Ala Thr Ser Glu Ala Ile Glu Asn Glu Thr Glu Met Ser Val
225                 230                 235                 240

Lys Glu Lys Asp Gly Asp Glu Glu Ala Lys Ser Glu Lys Pro Lys Lys
```

-continued

```
                245                 250                 255
Lys Asn Arg Ala Lys Lys Val Lys Thr Pro Thr Lys Glu Asp Gly Leu
            260                 265                 270

Val Ala Ser Ser Arg Asn Ala Glu Glu Asp Gly Val Ser Arg Asp
        275                 280                 285

Pro Gln Glu Asn Val Ala Lys Val Val Lys Pro Asn Lys Arg Ser
    290                 295                 300

Lys Lys Glu Gln Ser Ser Asn Ile Val Glu Glu Asp Ala
305                 310                 315

<210> SEQ ID NO 28
<211> LENGTH: 2092
<212> TYPE: DNA
<213> ORGANISM: Arabidopsis thaliana
<220> FEATURE:
<221> NAME/KEY: promoter
<222> LOCATION: (1)..(2092)
<223> OTHER INFORMATION: transcription regulating sequence from
      Arabidopsis thaliana gene At1g54480

<400> SEQUENCE: 28
ttttgacgaa tatacaaata cgtttctttt tttttggacg aatagaatgt caaatagatt      60
cgccttttta ttggcgtgtc gctttattta gaacttttg actttttgat atatttagag     120
aaagatgaag aaaaactaaa cattgtgaaa atgatatgaa agcacttaat agttatccaa     180
aactctttag ttaagagtct ttaatcttaa aaagacttgg aagagttgac gttggttgat     240
agtaaagact accgagttgg cgagttacct agttttagaa aaaaaaacat gtataaactt     300
gaatgagact agctagtttt gcgtttgttg atgctctcat aatcagtttt tctttctttg     360
agacgtctac taaagatttt tacgatcaat tggaatggtt tgcaaaatta tccatataac     420
taacaattaa tcaagtccaa ctgatttaca ataattcacg attaattagt gttgttggga     480
taatttattt agtccaaatt cgataatatt ttcaatatca aaaatatac aaattcatat      540 attaatggtt ttcaagcata ttttgccatt tgtggtttaa agttttttgt tttacagatt     600
atttggaaaa aagtatttaa aacgaagcag ctgaagaatt ttcaagatca cgtatgagaa     660
aatcaataat cattagaaga attccttatc aacgaattgg aagatttgat gtcattgcaa     720
agcttgaagg ctttggtgaa aacacatcaa tcttacttgt cccttacaac agatagaaag     780
atgtgtttta ataaataaat gcaaacagag acttttcata aggatcacat tacggaatca     840
ttcaccatgg tccatgtcaa atccaaaaca attacataac agtttgttct ccttatcttt     900
tgtagtaagc cgacacattc cacagtttta gacaataact gtttcttcag cttcttatgt     960
atattgccac aataaatcaa tgaatatatc gtaaatatca ttgtttagta cgtaagtcaa    1020
tgagagtact tgcagcctaa tcatccaaaa gcaacttgca aatgaaatgt gctccccact    1080
ctttgaaacc ttcaatataa agaacatcaa tgattataga acaagcaaac aaaaaaagtt    1140
tcaagctttc agacaaaaac aaaatgaaga ctaatttgt tattctactt cttctcctct    1200 gtgttttgc gatcagccct agtcaacaag aagagatcaa tcaacataat ccagggatat     1260
atcatcaaaa gctgctatac aaggtccaac aatggagaac atctttgaaa gaatcaaatt    1320
ctgtagaact caagctatct ttagcagcca ttgtggctgg agtgttatac ttccttgctg    1380
ccttaatctc gagcgcatgt ggaatcggca gtggaggttt attcattcca atcacgactc    1440
tagtttcacg gctagacttg aaaacaggtt caagcttcta tagtatacga aatagatgtt    1500
aaatcttatc tataatgttt caattctaag tggtaacatg cacacgtttt agaatctata    1560
```

-continued

```
tagtggatat tttctcaatc aagatttaat tttatgcatt ttattgacta atcttttaaa    1620
aaccaattat gcaatccgca tttgcttgat agatttgatt aaattatatt taattaaaat    1680
aaaatgaaaa tgtaaaatcg ataaaaaaca taccgtagaa aatttgcgca catccaataa    1740
gaaaatagtg tgtatcactg tatccttttc tatatttgaa tgtcccaaac tgaagtttgt    1800
attctttcac ttgaattgac ttgacttact tattacgtgg tatatacata tatgagtctt    1860
caaccataaa catatcattc gatgatgggt gttttctacg atctacactt ggcctatcat    1920
aaacaatagc aatcacttac atgtgccaca aaaacttctg actcattcac atacatatct    1980
tgttgaattc ttataaccat ggatgtattt gcattgaact cacactctca aatttctttg    2040
gagtttaatt catttgcttc tcttttcctt ttcttttttaa atgttatttg ca           2092
```

<210> SEQ ID NO 29
<211> LENGTH: 1653
<212> TYPE: DNA
<213> ORGANISM: Arabidopsis thaliana
<220> FEATURE:
<221> NAME/KEY: CDS
<222> LOCATION: (1)..(1653)
<223> OTHER INFORMATION: coding for leucine-rich repeat family protein

<400> SEQUENCE: 29

```
atg cct gct aca ata gtg cat gag ttg cag ttc ttg gat ttt tca gtg      48
Met Pro Ala Thr Ile Val His Glu Leu Gln Phe Leu Asp Phe Ser Val
1               5                   10                  15 aat gat att agt gga ctg ctc cct gat aat atc ggt tat gcg ctt ccg      96
Asn Asp Ile Ser Gly Leu Leu Pro Asp Asn Ile Gly Tyr Ala Leu Pro
            20                  25                  30 aat ctg tta cga atg aac ggc tca aga aat ggg ttt caa ggg cat tta    144
Asn Leu Leu Arg Met Asn Gly Ser Arg Asn Gly Phe Gln Gly His Leu
        35                  40                  45 cca tct tct atg ggt gag atg gta aac att aca tcc ctt gat cta tct    192
Pro Ser Ser Met Gly Glu Met Val Asn Ile Thr Ser Leu Asp Leu Ser
    50                  55                  60 tat aat aac ttc tcc ggg aag cta cct aga cgc ttt gtc act ggt tgt    240
Tyr Asn Asn Phe Ser Gly Lys Leu Pro Arg Arg Phe Val Thr Gly Cys
65                  70                  75                  80 ttt tca cta aaa cac ttg aag ctc tcc cac aac aat ttt agt ggc cat    288
Phe Ser Leu Lys His Leu Lys Leu Ser His Asn Asn Phe Ser Gly His
                85                  90                  95 ttt ctt cca aga gaa aca agc ttt act tcc ctg gaa gag ttg aga gtt    336
Phe Leu Pro Arg Glu Thr Ser Phe Thr Ser Leu Glu Glu Leu Arg Val
            100                 105                 110 gat agc aac tca ttc act ggg aag atc gga gtt ggt ttg ctt agc tcc    384
Asp Ser Asn Ser Phe Thr Gly Lys Ile Gly Val Gly Leu Leu Ser Ser
        115                 120                 125 aac act acg tta tca gtt ctt gac atg tcc aac aat ttt cta acg ggt    432
Asn Thr Thr Leu Ser Val Leu Asp Met Ser Asn Asn Phe Leu Thr Gly
    130                 135                 140 gat att cca agc tgg atg tct aac tta tct ggt tta act atc ttg tcg    480
Asp Ile Pro Ser Trp Met Ser Asn Leu Ser Gly Leu Thr Ile Leu Ser
145                 150                 155                 160 ata tca aac aat ttt tta gaa ggt acg ata cca cca tct ttg cta gcc    528
Ile Ser Asn Asn Phe Leu Glu Gly Thr Ile Pro Pro Ser Leu Leu Ala
                165                 170                 175 att ggc ttt ctt tct ctc atc gac cta tcg gga aac tta tta tct gga    576
Ile Gly Phe Leu Ser Leu Ile Asp Leu Ser Gly Asn Leu Leu Ser Gly
            180                 185                 190 tcc tta ccg tca cgt gtt ggt ggg gag ttt ggg ata aaa ttg ttc cta    624
```

-continued

```
Ser Leu Pro Ser Arg Val Gly Gly Glu Phe Gly Ile Lys Leu Phe Leu
        195                 200                 205 cac gac aac atg ctc acg ggg ccg att cca gac acg ttg ttg gaa aag      672
His Asp Asn Met Leu Thr Gly Pro Ile Pro Asp Thr Leu Leu Glu Lys
    210                 215                 220 gtc caa ata ctt gat tta cgg tac aat caa ctt tct ggg agt att cca      720
Val Gln Ile Leu Asp Leu Arg Tyr Asn Gln Leu Ser Gly Ser Ile Pro
225                 230                 235                 240 caa ttt gtc aat acc gag agc ata tat att ctt tta atg aag gga aac      768
Gln Phe Val Asn Thr Glu Ser Ile Tyr Ile Leu Leu Met Lys Gly Asn
                245                 250                 255 aac tta aca gga tct atg tca agg cag ctc tgt gat ttg aga aat atc      816
Asn Leu Thr Gly Ser Met Ser Arg Gln Leu Cys Asp Leu Arg Asn Ile
            260                 265                 270 aga ctt tta gat ctt tca gat aac aag ctc aat ggc ttc ata cct tca      864
Arg Leu Leu Asp Leu Ser Asp Asn Lys Leu Asn Gly Phe Ile Pro Ser
        275                 280                 285 tgt cta tat aat tta tca ttt gga cca gag gat aca aat tca tat gta      912
Cys Leu Tyr Asn Leu Ser Phe Gly Pro Glu Asp Thr Asn Ser Tyr Val
    290                 295                 300 ggt aca gcc ata acg aag att act ccg ttc aag ttt tac gaa tcc aca      960
Gly Thr Ala Ile Thr Lys Ile Thr Pro Phe Lys Phe Tyr Glu Ser Thr
305                 310                 315                 320 ttt gtg gta gag gat ttt gtg gta ata tcc tct agt ttt caa gaa att     1008
Phe Val Val Glu Asp Phe Val Val Ile Ser Ser Ser Phe Gln Glu Ile
                325                 330                 335 gaa atc aaa ttt tca atg aag cga agg tat gat tct tat ttt gga gca     1056
Glu Ile Lys Phe Ser Met Lys Arg Arg Tyr Asp Ser Tyr Phe Gly Ala
            340                 345                 350 act gaa ttc aac aat gac gta ctt gat tat atg tat gga atg gac cta     1104
Thr Glu Phe Asn Asn Asp Val Leu Asp Tyr Met Tyr Gly Met Asp Leu
        355                 360                 365 tca agc aat gag tta agt ggg gtt atc cca gca gag ctt gga agt ctc     1152
Ser Ser Asn Glu Leu Ser Gly Val Ile Pro Ala Glu Leu Gly Ser Leu
    370                 375                 380 tca aag cta cga gtc atg aat tta tct tgc aac ttc ttg tcc agt tca     1200
Ser Lys Leu Arg Val Met Asn Leu Ser Cys Asn Phe Leu Ser Ser Ser
385                 390                 395                 400 ata cca tct agc ttc tcc aat ctc aag gat att gag agc ctt gac ctt     1248
Ile Pro Ser Ser Phe Ser Asn Leu Lys Asp Ile Glu Ser Leu Asp Leu
                405                 410                 415 tcg cat aac atg tta caa gga agt att cct caa caa cta acc aac ctt     1296
Ser His Asn Met Leu Gln Gly Ser Ile Pro Gln Gln Leu Thr Asn Leu
            420                 425                 430 tct tct ctt gtt gtc ttt gat gtg tct tac aat aat tta tcc gga atc     1344
Ser Ser Leu Val Val Phe Asp Val Ser Tyr Asn Asn Leu Ser Gly Ile
        435                 440                 445 att ccc caa gga agg cag ttt aat acc ttt gac gag aaa agc tac ttg     1392
Ile Pro Gln Gly Arg Gln Phe Asn Thr Phe Asp Glu Lys Ser Tyr Leu
    450                 455                 460 gga aat cct ctt ctt tgt gga cca ccg acc aat aga agt tgt gat gct     1440
Gly Asn Pro Leu Leu Cys Gly Pro Pro Thr Asn Arg Ser Cys Asp Ala
465                 470                 475                 480 aag aag acc tca gat gaa tca gaa aat gga gga gaa gaa gaa gat gat     1488
Lys Lys Thr Ser Asp Glu Ser Glu Asn Gly Gly Glu Glu Glu Asp Asp
                485                 490                 495 gaa gct cct gtt gat atg ttg gcc ttc tat ttt agt agt gct tcg act     1536
Glu Ala Pro Val Asp Met Leu Ala Phe Tyr Phe Ser Ser Ala Ser Thr
            500                 505                 510
```

-continued

```
tat gta act aca ttg ata ggc att ttt ata ctt atg tgc ttt gat tgt      1584
Tyr Val Thr Thr Leu Ile Gly Ile Phe Ile Leu Met Cys Phe Asp Cys
            515                 520                 525 cct ttg cgt cga gca tgg ctc cgc att gtc gat gct tcc atc gcc tca      1632
Pro Leu Arg Arg Ala Trp Leu Arg Ile Val Asp Ala Ser Ile Ala Ser
    530                 535                 540 gtc aaa agt atg ttg cct taa                                          1653
Val Lys Ser Met Leu Pro
545                 550

<210> SEQ ID NO 30
<211> LENGTH: 550
<212> TYPE: PRT
<213> ORGANISM: Arabidopsis thaliana

<400> SEQUENCE: 30
```

Met Pro Ala Thr Ile Val His Glu Leu Gln Phe Leu Asp Phe Ser Val
1               5                   10                  15

Asn Asp Ile Ser Gly Leu Leu Pro Asp Asn Ile Gly Tyr Ala Leu Pro
            20                  25                  30

Asn Leu Leu Arg Met Asn Gly Ser Arg Asn Gly Phe Gln Gly His Leu
        35                  40                  45

Pro Ser Ser Met Gly Glu Met Val Asn Ile Thr Ser Leu Asp Leu Ser
    50                  55                  60

Tyr Asn Asn Phe Ser Gly Lys Leu Pro Arg Arg Phe Val Thr Gly Cys
65                  70                  75                  80

Phe Ser Leu Lys His Leu Lys Leu Ser His Asn Asn Phe Ser Gly His
                85                  90                  95

Phe Leu Pro Arg Glu Thr Ser Phe Thr Ser Leu Glu Glu Leu Arg Val
            100                 105                 110

Asp Ser Asn Ser Phe Thr Gly Lys Ile Gly Val Gly Leu Leu Ser Ser
        115                 120                 125

Asn Thr Thr Leu Ser Val Leu Asp Met Ser Asn Asn Phe Leu Thr Gly
    130                 135                 140

Asp Ile Pro Ser Trp Met Ser Asn Leu Ser Gly Leu Thr Ile Leu Ser
145                 150                 155                 160

Ile Ser Asn Asn Phe Leu Glu Gly Thr Ile Pro Ser Leu Leu Ala
                165                 170                 175

Ile Gly Phe Leu Ser Leu Ile Asp Leu Ser Gly Asn Leu Leu Ser Gly
            180                 185                 190

Ser Leu Pro Ser Arg Val Gly Gly Glu Phe Gly Ile Lys Leu Phe Leu
        195                 200                 205

His Asp Asn Met Leu Thr Gly Pro Ile Pro Asp Thr Leu Leu Glu Lys
    210                 215                 220

Val Gln Ile Leu Asp Leu Arg Tyr Asn Gln Leu Ser Gly Ser Ile Pro
225                 230                 235                 240

Gln Phe Val Asn Thr Glu Ser Ile Tyr Ile Leu Leu Met Lys Gly Asn
                245                 250                 255

Asn Leu Thr Gly Ser Met Ser Arg Gln Leu Cys Asp Leu Arg Asn Ile
            260                 265                 270

Arg Leu Leu Asp Leu Ser Asp Asn Lys Leu Asn Gly Phe Ile Pro Ser
        275                 280                 285

Cys Leu Tyr Asn Leu Ser Phe Gly Pro Glu Asp Thr Asn Ser Tyr Val
    290                 295                 300

Gly Thr Ala Ile Thr Lys Ile Thr Pro Phe Lys Phe Tyr Glu Ser Thr
305                 310                 315                 320

```
Phe Val Val Glu Asp Phe Val Val Ile Ser Ser Ser Phe Gln Glu Ile
                325                 330                 335

Glu Ile Lys Phe Ser Met Lys Arg Arg Tyr Asp Ser Tyr Phe Gly Ala
            340                 345                 350

Thr Glu Phe Asn Asn Asp Val Leu Asp Tyr Met Tyr Gly Met Asp Leu
        355                 360                 365

Ser Ser Asn Glu Leu Ser Gly Val Ile Pro Ala Glu Leu Gly Ser Leu
    370                 375                 380

Ser Lys Leu Arg Val Met Asn Leu Ser Cys Asn Phe Leu Ser Ser Ser
385                 390                 395                 400

Ile Pro Ser Ser Phe Ser Asn Leu Lys Asp Ile Glu Ser Leu Asp Leu
                405                 410                 415

Ser His Asn Met Leu Gln Gly Ser Ile Pro Gln Gln Leu Thr Asn Leu
            420                 425                 430

Ser Ser Leu Val Val Phe Asp Val Ser Tyr Asn Asn Leu Ser Gly Ile
        435                 440                 445

Ile Pro Gln Gly Arg Gln Phe Asn Thr Phe Asp Glu Lys Ser Tyr Leu
    450                 455                 460

Gly Asn Pro Leu Leu Cys Gly Pro Pro Thr Asn Arg Ser Cys Asp Ala
465                 470                 475                 480

Lys Lys Thr Ser Asp Glu Ser Glu Asn Gly Gly Glu Glu Asp Asp
                485                 490                 495

Glu Ala Pro Val Asp Met Leu Ala Phe Tyr Phe Ser Ser Ala Ser Thr
            500                 505                 510

Tyr Val Thr Thr Leu Ile Gly Ile Phe Ile Leu Met Cys Phe Asp Cys
        515                 520                 525

Pro Leu Arg Arg Ala Trp Leu Arg Ile Val Asp Ala Ser Ile Ala Ser
    530                 535                 540

Val Lys Ser Met Leu Pro
545                 550

<210> SEQ ID NO 31
<211> LENGTH: 2512
<212> TYPE: DNA
<213> ORGANISM: Arabidopsis thaliana
<220> FEATURE:
<221> NAME/KEY: promoter
<222> LOCATION: (1)..(2512)
<223> OTHER INFORMATION: transcription regulating sequence from
      Arabidopsis thaliana gene At4g11490

<400> SEQUENCE: 31
ttcgccttaa aatttgttga acaatgtga  aattcaaaaa taataataaa aaatcaaatg      60
tatttcggag actgcataac tcgtctttgg ataatacatt aataccatac attttttctt    120
ttattctagt ctcttttcta tatatatata tatatattta tttatttatt tattttttaaa   180 aacctattta gataaaacat agaagatttt aaagagtaga atgtatttac gacaaaaaaa    240
gaaaagaata gaatgtatttt acagcaaatg aaagtaacat acataattac atacaaaaag   300
ctagtaagaa ccttcacacc aaaaaaaaac tggtacgaac caaactgatt taccaatcaa    360
cagagccgat cctaggttgt ggggcttaaa acattttag tatgtggtct ttccaaaata    420
tactaacaat aaacgtttaa tattaataat ctataaaaca tgaaagggaa aaaatactat    480
aagcattatc tgaacgtgaa acaaacaaa cactatagaa acgtgaaaag aaaaaaattg    540
ctaagaaaaa gggtaatttg cagcaaaaaa aagaaggaac gaagtaagta gaagttgtgg   600
```

```
tcgtttgatc ccacgatcaa ggatgggtcg ggcctgccaa tcaacaatag aaaaatatat      660
tgtgaaaaca ttagcaatga attgtcacta gtccaaacag attacaactt ttcaaagttc      720
tttacaccct cataatttct tgttttatgc atccaactct atggtttagc atatgtggtc      780
cagttgtagg agggagcttt ggtaaagggt tttgttgtaa tcttaaaact tggggcctat      840
ttatagaaga aaaaaaataa ttgagggcct attttgtaaa gaaaaatttt ctaaaacttt      900
gggaatcaca ttcaattgtt tctccttgct ccgttgagtt accgcactaa tgctcactac      960
tagcaaacac actctttcag tgcgacagcc tcatgagctt gaagttgttt agcaaatcgg     1020
ttcctaccaa tgtactaaac cggttatata atctgattat gtataaccaa accggttatt     1080
gtataaatgt ccaaccgggg ttcacgattc taccgttgtt ccgcctaatt ctgatttgtt     1140
aaacgacgag aaatttctta tggaagttag ggtttcctgg ccgttgattg gttcgttccc     1200
tgttaccttg ttccattcca atcagttctc gtagagcttc taatgtcacg gctcgtgatg     1260
gcttcttcaa ttcttcgagt gggaggatgc gtaatccatg tgccaatagc agagtcgtgc     1320
tcagattgta ccaggggcgg atctaggtgt atgggatgtg gggcacgtgc cctacattaa     1380
attataagta ttagcttgta aacttatgca gtttaaatga ttcagcacaa ctggttaagt     1440
gttttcaata ttcgtccatc cttacccagg ttcgagacta gttgaagtaa ctttttttctt     1500 tttttgactt tgctcatttt ttccccccaat tttatcaatt taatcactta tttcttcctt     1560
tgatttatga acatccactt ttaactttct tttaaatttt ctttattaat tgattagata     1620
gtatatgtgt attgatatat ttctaaaatg tttgatatat ctattcattt acttttatgt     1680
gaaaatgaat aacaaagtta tatgaacaca atttcatagt tttttttttgg gtacctatat     1740 aaattgtggg aaacaaatta cagaatttat tgaactacat atttttatcac aaacttatag     1800 tttaataacg aatagtatat ataataattt tgataaaaaa taatatataa taagtaaatt     1860
aatagtgccc cagattaaat attttttctag atccgccact ggattgtacc atggaagcgt     1920
ctgatggagt tgtcttaatt agacatatgc caatggaaat gtaatgctgt ccgacaatcg     1980
tcttgatgct tcaagtagcc tgtatttttt tttccgtggg ggttcgaaac ttggattcag     2040
tcaggtcatt ctttaatctt tacttttaaac ccattgtcaa caatgcctct agtaaaacaa     2100
tggttttgta ttactgtctg tgctgagaaa gtaataagat aagctattga aattgtcaaa     2160
atattactaa tttgggtctt tggattgctc aatttgttgg ttatttaact catatcactc     2220
tgcttcgttg tgttacgttg aggagattca ttcaacaagc atagtgggcg tgtagtctgg     2280
gtgcatctca catcattaac atttttgaaa cttcaacatt cttttaataa acatataaca     2340
catcagctca ttgctttgat tggttctctg attttgtcta tgctctgact tagcttttat     2400
aatgccttgg atattttaag tttgacaact tgctgagaga actcaattgc tatttaactg     2460
atatgaagtg tacggatatg tacatactaa ccccaaacac atttgtaaaa tc             2512
```

<210> SEQ ID NO 32
<211> LENGTH: 2512
<212> TYPE: DNA
<213> ORGANISM: Arabidopsis thaliana
<220> FEATURE:
<221> NAME/KEY: promoter
<222> LOCATION: (1)..(2512)
<223> OTHER INFORMATION: transcription regulating sequence from
      Arabidopsis thaliana gene At4g11490

<400> SEQUENCE: 32

```
tcgccttaaa atttgttgaa acaatgtgaa attcaaaaat aataataaaa aatcaaatgt       60
```

```
atttcggaga ctgcataact cgtctttgga taatacatta ataccataca ttttttcttt      120
tattctagtc tcttttctat atatatatat atatatttat ttatttattt attttttaaaa     180 acctatttag ataaaacata gaagatttta agaatagaa  tgtatttacg acaaaaaaag     240 aaagaatag  aatgtattta cagcaaatga aagtaacata cataattaca tacaaaaagc     300
tagtaagaac cttcacacca aaaaaaaact ggtacgaacc aaactgattt accaatcaac     360
agagccgatc ctaggttgtg gggcttaaaa cattttagt  atgtggtctt tccaaaatat     420
actaacaata aacgtttaat attaataatc tataaaacat gaaagggaaa aaatactata     480
agcattatct gaacgtgaaa caaaacaaac actatagaaa cgtgaaaaga aaaaaattgc     540
taagaaaaag ggtaatttgc agcaaaaaaa aagaaggaac gaagtaagta aagttgtgg     600 tcgtttgatc ccacgatcaa ggatgggtcg ggcctgccaa tcaacaatag aaaaatatat     660
tgtgaaaaca ttagcaatga attgtcacta gtccaaacag attacaactt ttcaaagttc     720
tttcacccct cataatttct tgttttatgc atccaactct atggtttagc atatgtggtc     780
cagttgtagg agggagcttt ggtaaagggt tttgttgtaa tcttaaaact tggggcctat     840
ttatagaaga aaaaaaataa ttgagggcct attttgtaaa gaaaaatttt ctaaaacttt     900
gggaatcaca ttcaattgtt tctccttgct ccgttgagtt accgcactaa tgctcactac     960
tagcaaacac actctttcag tgcgacagcc tcatgagctt gaagttgttt agcaaatcgg    1020
ttcctaccaa tgtactaaac cggttatata atctgattat gtataaccaa accggttatt    1080
gtataaatgt ccaaccgggg ttcacgattc taccgttgtt ccgcctaatt ctgatttgtt    1140
aaacgacgag aaatttctta tggaagttag ggtttcctgg ccgttgattg gttcgttccc    1200
tgttaccttg ttccattcca atcagttctc gtagagcttc taatgtcacg gctcgtgatg    1260
gcttcttcaa ttcttcgagt gggaggatgc gtaatccatg tgccaatagc agagtcgtgc    1320
tcagattgta ccaggggcgg atctaggtgt atgggatgtg gggcacgtgc cctacattaa    1380
attataagta ttagcttgta aacttatgca gtttaaatga ttcagcacaa ctggttaagt    1440
gttttcaata ttcgtccatc cttacccagg ttcgagacta gttgaagtaa ctttttttctt   1500 tttttgactt tgctcatttt ttcccccaat tttatcaatt taatcactta tttcttcctt    1560
tgatttatga acatccactt ttaactttct tttaaaattt ctttattaat tgattagata    1620
gtatatgtgt attgatatat ttctaaaatg tttgatatat ctattcattt acttttatgt    1680
gaaaatgaat aacaaagtta tatgaacaca atttcatagt ttttttttgg gtacctatat    1740
aaattgtgag aaacaaatta cagaatttat tgaactacat atttttatcac aaacttatag   1800 tttaataacg aatagtatat ataataattt tgataaaaa  taatatataa taagtaaatt    1860
aatagtgccc cagattaaat attttttctag atccgccact ggattgtacc atggaagcgt   1920
ctgatggagt tgtcttaatt agacatatgc caatggaaat gtaatgctgt ccgacaatcg    1980
tcttgatgct tcaagtagcc tgtatttttt tttccgtggg ggttcgaaac ttggattcag    2040
tcaggtcatt ctttaatctt tactttaaac ccattgtcaa caatgcctct agtaaaacaa    2100
tggttttgta ttactgtttg tgctgagaaa gtaataagat aagctattga aattgtcaaa    2160
atattactaa tttgggtctt tggattgctc aatttgttgg ttatttaact catatcactc    2220
tgcttcgttg tgttacgttg aggagattca ttcaacaagc atagtgggcg tgtagtctgg    2280
gtgcatctca catcattaac attttgaaa  cttcaacatt cttttaataa acatataaca    2340
catcagctca ttgctttgat tggttctctg attttgtcta tgctctgact agcttttat    2400 aatgccttgg atattttaag tttgacaact tgctgagaga actcaattgc tatttaactg    2460
```

```
atatgaagtg tacggatatg tacatactaa ccccaaacac atttgtaaaa tc                    2512

<210> SEQ ID NO 33
<211> LENGTH: 1911
<212> TYPE: DNA
<213> ORGANISM: Arabidopsis thaliana
<220> FEATURE:
<221> NAME/KEY: CDS
<222> LOCATION: (1)..(1911)
<223> OTHER INFORMATION: coding for serin/threonin kinase like protein

<400> SEQUENCE: 33 atg aga aag acc aag aag att tcc ttt ttg atc ttc tgg gtt gtt ctc         48
Met Arg Lys Thr Lys Lys Ile Ser Phe Leu Ile Phe Trp Val Val Leu
1               5                   10                  15 ata agc ata att ggt gct att tct tcg caa caa tgc aac gaa act ggg         96
Ile Ser Ile Ile Gly Ala Ile Ser Ser Gln Gln Cys Asn Glu Thr Gly
            20                  25                  30 tat ttt gaa cct tgg aaa act tac gac acc aac cgt agg cag atc ctt        144
Tyr Phe Glu Pro Trp Lys Thr Tyr Asp Thr Asn Arg Arg Gln Ile Leu
        35                  40                  45 aca tct ctt gct tcc aaa gtg gtg gat cac tac ggc ttc tac aat tct        192
Thr Ser Leu Ala Ser Lys Val Val Asp His Tyr Gly Phe Tyr Asn Ser
    50                  55                  60 tcc atc ggc aaa gtt cct gac gaa gtg cac gta atg ggg atg tgc atc        240
Ser Ile Gly Lys Val Pro Asp Glu Val His Val Met Gly Met Cys Ile
65                  70                  75                  80 gac ggg acc gaa cct acg gtt tgc tcc gat tgt ctc aag gtc gcg gcc        288
Asp Gly Thr Glu Pro Thr Val Cys Ser Asp Cys Leu Lys Val Ala Ala
                85                  90                  95 gac caa tta caa gag aat tgt cct aac caa act gaa gcg tat aca tgg        336
Asp Gln Leu Gln Glu Asn Cys Pro Asn Gln Thr Glu Ala Tyr Thr Trp
            100                 105                 110 aca cct cat aag acg ctc tgt ttt gct cgt tac tct aac agt tca ttc        384
Thr Pro His Lys Thr Leu Cys Phe Ala Arg Tyr Ser Asn Ser Ser Phe
        115                 120                 125 ttc aag agg gtt gga ttg cac cca ctt tac atg gag cat agt aat gtg        432
Phe Lys Arg Val Gly Leu His Pro Leu Tyr Met Glu His Ser Asn Val
    130                 135                 140 gat atc aaa tca aat ttg aca tat tta aat acg ata tgg gag gct cta        480
Asp Ile Lys Ser Asn Leu Thr Tyr Leu Asn Thr Ile Trp Glu Ala Leu
145                 150                 155                 160 acg gat cgt ttg atg tct gac gca tcc tcg gat tat aat gca tca tta        528
Thr Asp Arg Leu Met Ser Asp Ala Ser Ser Asp Tyr Asn Ala Ser Leu
                165                 170                 175 tct agt cgt aga tat tat gca gct aat gta aca aat ctg aca aat ttc        576
Ser Ser Arg Arg Tyr Tyr Ala Ala Asn Val Thr Asn Leu Thr Asn Phe
            180                 185                 190 cag aat ata tat gca tta atg cta tgc act cct gat cta gaa aaa ggt        624
Gln Asn Ile Tyr Ala Leu Met Leu Cys Thr Pro Asp Leu Glu Lys Gly
        195                 200                 205 gct tgt cac aac tgt ctg gaa aaa gct gtt tct gaa tat ggc aac ctt        672
Ala Cys His Asn Cys Leu Glu Lys Ala Val Ser Glu Tyr Gly Asn Leu
    210                 215                 220 agg atg caa aga gga att gtt gca tgg cca agc tgc tgt ttt cgg tgg        720
Arg Met Gln Arg Gly Ile Val Ala Trp Pro Ser Cys Cys Phe Arg Trp
225                 230                 235                 240 gat ctg tat ccc ttc atc gga gct ttt aat ttg aca ctt tca ccc ccg        768
Asp Leu Tyr Pro Phe Ile Gly Ala Phe Asn Leu Thr Leu Ser Pro Pro
                245                 250                 255
```

```
                                                                        -continued cca ggt agc aaa agg aat atc tca gtt gga ttc ttt gtg gcc att gtt          816
Pro Gly Ser Lys Arg Asn Ile Ser Val Gly Phe Phe Val Ala Ile Val
        260                 265                 270 gtt gcc acc gga gtt gtc atc tct gtg cta tct act tta gta gta gta          864
Val Ala Thr Gly Val Val Ile Ser Val Leu Ser Thr Leu Val Val Val
    275                 280                 285 ctt gtt tgc aga aag aga aaa act gat cct cca gag gaa tca cct aaa          912
Leu Val Cys Arg Lys Arg Lys Thr Asp Pro Pro Glu Glu Ser Pro Lys
290                 295                 300 tat tca ctg cag tat gat ctt aag aca att gaa gct gca aca tgt acc          960
Tyr Ser Leu Gln Tyr Asp Leu Lys Thr Ile Glu Ala Ala Thr Cys Thr
305                 310                 315                 320 ttt tca aag tgc aac atg ctt ggt caa ggt gga ttt gga gaa gtt ttc         1008
Phe Ser Lys Cys Asn Met Leu Gly Gln Gly Gly Phe Gly Glu Val Phe
            325                 330                 335 aag ggt gtg ctt caa gac gga tca gaa att gca gtg aag agg ctg tca         1056
Lys Gly Val Leu Gln Asp Gly Ser Glu Ile Ala Val Lys Arg Leu Ser
        340                 345                 350 aaa gaa tca gct caa ggt gta caa gag ttc cag aat gag act agt ctc         1104
Lys Glu Ser Ala Gln Gly Val Gln Glu Phe Gln Asn Glu Thr Ser Leu
    355                 360                 365 gtg gca aag ctt cag cac aga aat ttg gtt gga gtt ctc ggg ttt tgt         1152
Val Ala Lys Leu Gln His Arg Asn Leu Val Gly Val Leu Gly Phe Cys
370                 375                 380 atg gaa gga gaa gaa aag ata ctc gta tac gaa ttt gtt ccc aac aaa         1200
Met Glu Gly Glu Glu Lys Ile Leu Val Tyr Glu Phe Val Pro Asn Lys
385                 390                 395                 400 agc ctc gac cag ttc ttg ttt gaa cct aca aag aaa ggc caa ctg gat         1248
Ser Leu Asp Gln Phe Leu Phe Glu Pro Thr Lys Lys Gly Gln Leu Asp
            405                 410                 415 tgg gcg aaa cgg tac aag att att gtt gga act gct aga gga att cta         1296
Trp Ala Lys Arg Tyr Lys Ile Ile Val Gly Thr Ala Arg Gly Ile Leu
        420                 425                 430 tat ctt cat cat gac tca ccc ctc aaa atc ata cac cgt gac ctc aaa         1344
Tyr Leu His His Asp Ser Pro Leu Lys Ile Ile His Arg Asp Leu Lys
    435                 440                 445 gct agt aac atc ctc tta gat gct gaa atg gaa ccc aaa gtc gca gat         1392
Ala Ser Asn Ile Leu Leu Asp Ala Glu Met Glu Pro Lys Val Ala Asp
450                 455                 460 ttt gga atg gca aga att ttt agg gtg gat caa tct cga gcg gat aca         1440
Phe Gly Met Ala Arg Ile Phe Arg Val Asp Gln Ser Arg Ala Asp Thr
465                 470                 475                 480 aga agg gta gtt gga acc cat ggc tac ata tct cca gag tat ttg atg         1488
Arg Arg Val Val Gly Thr His Gly Tyr Ile Ser Pro Glu Tyr Leu Met
            485                 490                 495 cat ggc cag ttc tcg gtg aaa tct gat gtc tat agt ttt gga gtc ttg         1536
His Gly Gln Phe Ser Val Lys Ser Asp Val Tyr Ser Phe Gly Val Leu
        500                 505                 510 gtt ctt gag att ata agt gga aaa aga aac agc aac ttc cat gaa act         1584
Val Leu Glu Ile Ile Ser Gly Lys Arg Asn Ser Asn Phe His Glu Thr
    515                 520                 525 gat gaa tcc gga aag aat ttg gtc aca tat gct tgg agg cat tgg aga         1632
Asp Glu Ser Gly Lys Asn Leu Val Thr Tyr Ala Trp Arg His Trp Arg
530                 535                 540 aac gga tca cca tta gag ctt gtg gat tca gaa ctc gaa aag aat tat         1680
Asn Gly Ser Pro Leu Glu Leu Val Asp Ser Glu Leu Glu Lys Asn Tyr
545                 550                 555                 560 cag agt aat gaa gtc ttc aga tgc atc cat atc gcg cta tta tgt gtt         1728
Gln Ser Asn Glu Val Phe Arg Cys Ile His Ile Ala Leu Leu Cys Val
            565                 570                 575
```

```
caa aat gat cca gaa caa cgt ccg aat tta tct act atc atc atg atg        1776
Gln Asn Asp Pro Glu Gln Arg Pro Asn Leu Ser Thr Ile Ile Met Met
        580                 585                 590 ctc aca agt aac tcc atc act tta ccg gtg cct cag tca ccg gta tat        1824
Leu Thr Ser Asn Ser Ile Thr Leu Pro Val Pro Gln Ser Pro Val Tyr
        595                 600                 605 gag gga atg gac atg ttt cta cct tct atc aaa tct ctt cct ggt tct        1872
Glu Gly Met Asp Met Phe Leu Pro Ser Ile Lys Ser Leu Pro Gly Ser
        610                 615                 620 gtc aac gat tca ttg att gat gac tta gtt cct cgc tga                    1911
Val Asn Asp Ser Leu Ile Asp Asp Leu Val Pro Arg
625                 630                 635

<210> SEQ ID NO 34
<211> LENGTH: 636
<212> TYPE: PRT
<213> ORGANISM: Arabidopsis thaliana

<400> SEQUENCE: 34

Met Arg Lys Thr Lys Lys Ile Ser Phe Leu Ile Phe Trp Val Val Leu
1               5                   10                  15

Ile Ser Ile Ile Gly Ala Ile Ser Ser Gln Gln Cys Asn Glu Thr Gly
            20                  25                  30

Tyr Phe Glu Pro Trp Lys Thr Tyr Asp Thr Asn Arg Arg Gln Ile Leu
        35                  40                  45

Thr Ser Leu Ala Ser Lys Val Val Asp His Tyr Gly Phe Tyr Asn Ser
    50                  55                  60

Ser Ile Gly Lys Val Pro Asp Glu Val His Val Met Gly Met Cys Ile
65                  70                  75                  80

Asp Gly Thr Glu Pro Thr Val Cys Ser Asp Cys Leu Lys Val Ala Ala
                85                  90                  95

Asp Gln Leu Gln Glu Asn Cys Pro Asn Gln Thr Glu Ala Tyr Thr Trp
            100                 105                 110

Thr Pro His Lys Thr Leu Cys Phe Ala Arg Tyr Ser Asn Ser Ser Phe
        115                 120                 125

Phe Lys Arg Val Gly Leu His Pro Leu Tyr Met Glu His Ser Asn Val
    130                 135                 140

Asp Ile Lys Ser Asn Leu Thr Tyr Leu Asn Thr Ile Trp Glu Ala Leu
145                 150                 155                 160

Thr Asp Arg Leu Met Ser Asp Ala Ser Ser Asp Tyr Asn Ala Ser Leu
                165                 170                 175

Ser Ser Arg Arg Tyr Tyr Ala Ala Asn Val Thr Asn Leu Thr Asn Phe
            180                 185                 190

Gln Asn Ile Tyr Ala Leu Met Leu Cys Thr Pro Asp Leu Glu Lys Gly
        195                 200                 205

Ala Cys His Asn Cys Leu Glu Lys Ala Val Ser Glu Tyr Gly Asn Leu
    210                 215                 220

Arg Met Gln Arg Gly Ile Val Ala Trp Pro Ser Cys Cys Phe Arg Trp
225                 230                 235                 240

Asp Leu Tyr Pro Phe Ile Gly Ala Phe Asn Leu Thr Leu Ser Pro Pro
                245                 250                 255

Pro Gly Ser Lys Arg Asn Ile Ser Val Gly Phe Phe Val Ala Ile Val
            260                 265                 270

Val Ala Thr Gly Val Val Ile Ser Val Leu Ser Thr Leu Val Val Val
        275                 280                 285
```

-continued

```
Leu Val Cys Arg Lys Arg Lys Thr Asp Pro Pro Glu Glu Ser Pro Lys
    290                 295                 300

Tyr Ser Leu Gln Tyr Asp Leu Lys Thr Ile Glu Ala Ala Thr Cys Thr
305                 310                 315                 320

Phe Ser Lys Cys Asn Met Leu Gly Gln Gly Gly Phe Gly Glu Val Phe
                325                 330                 335

Lys Gly Val Leu Gln Asp Gly Ser Glu Ile Ala Val Lys Arg Leu Ser
            340                 345                 350

Lys Glu Ser Ala Gln Gly Val Gln Glu Phe Gln Asn Glu Thr Ser Leu
        355                 360                 365

Val Ala Lys Leu Gln His Arg Asn Leu Val Gly Val Leu Gly Phe Cys
    370                 375                 380

Met Glu Gly Glu Glu Lys Ile Leu Val Tyr Glu Phe Val Pro Asn Lys
385                 390                 395                 400

Ser Leu Asp Gln Phe Leu Phe Glu Pro Thr Lys Lys Gly Gln Leu Asp
                405                 410                 415

Trp Ala Lys Arg Tyr Lys Ile Ile Val Gly Thr Ala Arg Gly Ile Leu
            420                 425                 430

Tyr Leu His His Asp Ser Pro Leu Lys Ile Ile His Arg Asp Leu Lys
        435                 440                 445

Ala Ser Asn Ile Leu Leu Asp Ala Glu Met Glu Pro Lys Val Ala Asp
    450                 455                 460

Phe Gly Met Ala Arg Ile Phe Arg Val Asp Gln Ser Arg Ala Asp Thr
465                 470                 475                 480

Arg Arg Val Val Gly Thr His Gly Tyr Ile Ser Pro Glu Tyr Leu Met
                485                 490                 495

His Gly Gln Phe Ser Val Lys Ser Asp Val Tyr Ser Phe Gly Val Leu
            500                 505                 510

Val Leu Glu Ile Ile Ser Gly Lys Arg Asn Ser Asn Phe His Glu Thr
        515                 520                 525

Asp Glu Ser Gly Lys Asn Leu Val Thr Tyr Ala Trp Arg His Trp Arg
    530                 535                 540

Asn Gly Ser Pro Leu Glu Leu Val Asp Ser Glu Leu Glu Lys Asn Tyr
545                 550                 555                 560

Gln Ser Asn Glu Val Phe Arg Cys Ile His Ile Ala Leu Leu Cys Val
                565                 570                 575

Gln Asn Asp Pro Glu Gln Arg Pro Asn Leu Ser Thr Ile Ile Met Met
            580                 585                 590

Leu Thr Ser Asn Ser Ile Thr Leu Pro Val Pro Gln Ser Pro Val Tyr
        595                 600                 605

Glu Gly Met Asp Met Phe Leu Pro Ser Ile Lys Ser Leu Pro Gly Ser
    610                 615                 620

Val Asn Asp Ser Leu Ile Asp Asp Leu Val Pro Arg
625                 630                 635

<210> SEQ ID NO 35
<211> LENGTH: 1854
<212> TYPE: DNA
<213> ORGANISM: Arabidopsis thaliana
<220> FEATURE:
<221> NAME/KEY: promoter
<222> LOCATION: (1)..(1854)
<223> OTHER INFORMATION: transcription regulating sequence localized
      downstream and in opposite direction from Arabidopsis thaliana
      gene At2g31160

<400> SEQUENCE: 35
```

```
tcgagtcatt ttcaattcat cctgaaactt taggaaaatt gaaaggtaga actacagaat    60
tgttttatcc tgtcaaatga attttacaat atgtggaagg aaattcagaa atggacaaga   120
ctcaataaaa gttgaagggc tggggtcttt gagtgctctg ggagtaaaca acttacagag   180
acaagacaag tgagagacag aactctggct ctacctctaa cacactcatg aatgatgcaa   240
cattacacaa cgtaccaaga tgagtattat tttaaaagag attttagtat tagttatatt   300
tcatttatgt acacataatg aggatatcaa gatagcaaaa gtatcacata tatggtctaa   360
gtttaaggta ctaaaaaaat gtgataacat atgttgtttg attatcaaat ttgacaaaga   420
ttgtttcatc cgccggacct attgttctga cgctatctaa actattatat tgattaaaac   480
atataccaaa tgagataaaa atctgtccaa tcaaaacttt ttcaagttgt atttgtcgtt   540
ttcaaatata attttattta aatattaaat aaattcatta gcttatgaaa attaccccca   600
aataaaatca gatacccccat tacaacaaaa aaaaaccagc aaaatatata ctgaaaaatg   660
atatgttttc tctttctctt tctctctata cacatagtta tatacttata tatatacagt   720
ttaaactctc actttagcag ccaaaactac aaaattttat gagatctata attttcacaa   780
tttgcaaata tatatcacaa aatatgatgt acgaaccttta tttaattata taattgacaa   840
cacaaataaa tgaaaagaat ggtgcaactt gcataatgga agaagaagat catagacatt   900 cgattttttga aaaacatatt ctatgcatct tcattagaat agcataccaa aacttattta   960
aaaaactggt taagatatac taggtaaatt tcagttttct tatttataat tccgctattc  1020
gtaggattac catttgtttt tttcattttt ttcgtaggat taccattact aatcaaaatg  1080
atgccgtatt gctcttagaa aagttgacat catgtaggca actactagag attccatctt  1140
catgtttcag aattgcggct agcaatcatg tggcaatctt tccgtattag gcaacttaac  1200
tccataaaat aaattaatat tttttttaca tcgttgattt gataactata aacgatgagt  1260
tgtagtattt ttttctttg ttgttaataa gaatgtggta aacaatggta tactaatgcc  1320
aattttgaat actatgtata tcttgtactt gtgaaaaaat ataagtaggt catttcacca  1380
attaatttta aaatataaga tcattagaca tcacataaaa ttagtctttc ctcttgttgg  1440
ccttcacaag ggtgttatgt catatatgtt aagttagtga aaaccgtagt tactacaaat  1500
gagttaaata tctcgtcgct ataattgtat ttaaatgaca tacttagtgt cgctataatt  1560
gtattgaaat gacatactta gtggcacaca atctatttaa catggaatta ccataattaa  1620
aatacaacat caatcatgaa tcatcagatc tacaaaatct agggtttatg caaaagccga  1680
gacacgcaca ttgttcttct tgagtaaaaa agtaagtact aagaaacata aagtgggagaa  1740 tttacggaac tgtttttttt tccctacaat tatgctgtaa gagaacatat cactcacaac  1800
tcacaagtaa acctatgaaa cctactttaa catgaaaaag aaatgatttt agag        1854
```

<210> SEQ ID NO 36
<211> LENGTH: 1855
<212> TYPE: DNA
<213> ORGANISM: Arabidopsis thaliana
<220> FEATURE:
<221> NAME/KEY: promoter
<222> LOCATION: (1)..(1855)
<223> OTHER INFORMATION: transcription regulating sequence localized
      downstream and in opposite direction from Arabidopsis thaliana
      gene At2g31160

<400> SEQUENCE: 36

```
tcgagtcatt ttcaattcat cctgaaactt taggaaaatt gaaaggtaga actacagaat    60
```

```
tgttttatcc tgtcaaatga attttacaat atgtggaagg aaattcagaa atggacaaga      120
ctcaataaaa gttgaagggc tggggtcttt gagtgctctg ggagtaaaca acttacagag      180
acaagacaag tgagagacag aactctggct ctacctctaa cacactcatg aatgatgcaa      240 cattcacaa cgtaccaaga tgagtattat ttttaaagag atttttagtat tagttatatt      300 tcatttatgt acacataatg aggatatcaa gatagcaaaa gtcacacata tatggtctaa      360
gtttaaggta ctaaaaaaat gtgataacat atgttgtttg attatcaaat ttgacaaaga      420
ttgtttcatc cgccggacct attgttctga cgctatctaa actattatat tgattaaaac      480
atataccaaa tgagataaaa atctgtccaa tcaaaacttt ttcaagttgt atttgtcgtt      540
ttcaaatata attttattta aatattaaat aaattcatta gcttatgaaa attaccccca      600
aataaaatca gatacccat tacaacaaaa aaaaccagc aaaatatata ctgaaaaatg       660
atatgttttc tctttctctt tctctctata catatagtta tatacttata tatatacagt      720
ttaaactctc actttagcag ccaaaactac aaaattttat gagatctata attttccacaa    780 tttgcaaata tatatcacaa aatatgatgt acgaacctta tttaattata taattgacaa     840
cacaaataaa tgaaaagaat ggtgcaactt gcataatgga agaagaagat catagacatt     900 cgattttga aaaacatatt ctatgcatct tcattagaat agcataccaa aacttattta      960
aaaaactggt taagatatac taggtaaatt tcagttttct tatttataat tccgctattc    1020
gtaggattac catttgtttt tttcattttt ttcgtaggat taccattact aatcaaaatg    1080
atgccgcatt gctcttagaa aagttgacat catataggca actactagag attccatctt   1140
catgtttcag aattgcagct agcaatcatg tggcaatctt tccgtattag gcaacttaac   1200
tccataaaat aaattaatat ttttttttaca tcgttgattt gataactata aacgatgagt   1260
tgtagtattt ttttttctttg ttgttaataa gaatgtggta aacaatggta tactaatgcc   1320
aattttgaat actatgtata tcttgtactt gtgaaaaaat ataagtaggt catttccacca   1380 attaatttta aaatataaga tcattagaca tcacataaaa ttagtctttc ctcttgttgg   1440
ccttcacaag ggtgttatgt catatatgtt aagttagtga aaaccgtagt tactacaaat   1500
gagttaaata tctcgtcgct ataattgtat ttaaatgaca tacttagtgt cgctataatt   1560
gtattgaaat gacatactta gtggcacaca atctatttaa catggaatta ccataattaa   1620
aatacaacat caatcatgaa tcatcagatc tacaaaatct agggtttatg caaaagccga   1680
gacacgcaca ttgttcttct tgagtaaaaa agtaagtact aagaaacata agtgggagaa   1740
tttacggaac tgttttttttt tccctacaat tatgctgtaa gagaacatat cactcacaac   1800
tcacaagtaa acctatgaaa cctactttaa catgaaaaag aaatgatttt agagc         1855
```

<210> SEQ ID NO 37
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 37
ggcgctcgag tattgaaata aaatcagttg                                        30

<210> SEQ ID NO 38
<211> LENGTH: 34
<212> TYPE: DNA
<213> ORGANISM: Artificial Sequence
<220> FEATURE:
<223> OTHER INFORMATION: Oligonucleotide primer

<400> SEQUENCE: 38
cggccatgga aggtgtatat atagagatta cttc                                    34

<210> SEQ ID NO 39
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 39
gcggatccgc ctccatagga tgctcatgct gt                                      32

<210> SEQ ID NO 40
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 40
gagccatggc tacacgagtc agattcc                                            27

<210> SEQ ID NO 41
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 41
cgcggatcca tttcctttaa agagaataat ttaagttaa                               39

<210> SEQ ID NO 42
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 42
gcgccatggc gtttaggttt tgtgtttaaa attcg                                   35

<210> SEQ ID NO 43
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 43
cgccatggag gaaaaatgga agaggaagag ttc                                     33

<210> SEQ ID NO 44
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 44
cgcggatcct gttttgggag atgcattcaa taaaga                                  36

<210> SEQ ID NO 45

```
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 45
gcgccatggt ctcaaaccaa caaatcttgt agccac                                 36

<210> SEQ ID NO 46
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 46
cgcggatcca taatcaacct tctcgtttg                                         29

<210> SEQ ID NO 47
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 47
gcgccatggc agaaagtgaa gatctcgact aagag                                  35

<210> SEQ ID NO 48
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 48
cgctcgagta atcaaccttc tcgtttg                                           27

<210> SEQ ID NO 49
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 49
cgccatggcc tccctctctg cgcctcctgg                                        30

<210> SEQ ID NO 50
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 50
cgcggatcca ttataactct atgttgcat                                         29

<210> SEQ ID NO 51
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 51
```

-continued

```
gcgccatgga gtctagatat atattgcgag ttgtc                         35

<210> SEQ ID NO 52
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 52
cgcggatccc ttcttcttac gtttccagt                                29

<210> SEQ ID NO 53
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 53
gcgccatggc agtaagatta ttgtaagaga aatgc                         35

<210> SEQ ID NO 54
<211> LENGTH: 37
<212> TYPE: DNA
<213> ORGANISM: Artificial Sequence
<220> FEATURE:
<223> OTHER INFORMATION: Oligonucleotide primer

<400> SEQUENCE: 54
cgcggatcct tttgacgaat atacaaatac gtttctt                       37

<210> SEQ ID NO 55
<211> LENGTH: 42
<212> TYPE: DNA
<213> ORGANISM: Artificial Sequence
<220> FEATURE:
<223> OTHER INFORMATION: Oligonucleotide primer

<400> SEQUENCE: 55
gcgactagtt gcaaataaca tttaaaaaag aaagaaaaag ag                  42

<210> SEQ ID NO 56
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 56
gcgctcgagt tcgccttaaa atttgttga                                29

<210> SEQ ID NO 57
<211> LENGTH: 35
<212> TYPE: DNA
<213> ORGANISM: Artificial Sequence
<220> FEATURE:
<223> OTHER INFORMATION: Oligonucleotide primer

<400> SEQUENCE: 57
cgcggatccg attttacaaa tgtgtttggg gttag                         35

<210> SEQ ID NO 58
<211> LENGTH: 25
<212> TYPE: DNA
```

<213> ORGANISM: Artificial Sequence
<220> FEATURE:
<223> OTHER INFORMATION: Oligonucleotide primer

<400> SEQUENCE: 58
agagataaat actcgagtca ttttc                                                25

<210> SEQ ID NO 59
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 59
ccgccatggc tctaaaatca tttcttt                                              27

<210> SEQ ID NO 60
<211> LENGTH: 8986
<212> TYPE: DNA
<213> ORGANISM: Artificial Sequence
<220> FEATURE:
<223> OTHER INFORMATION: binary vector pSUN0301

<400> SEQUENCE: 60
cgttgtaaaa cgacggccag tgaattcgag ctcggtacct cgagcccggg cgatatcgga      60
tccactagtc tagagtcgat cgaccatggt acgtcctgta gaaacccaa cccgtgaaat      120
caaaaaactc gacggcctgt gggcattcag tctggatcgc gaaaactgtg gaattggtca     180
gcgttggtgg gaaagcgcgt tacaagaaag ccgggcaatt gctgtgccag cagttttaa     240
cgatcagttc gccgatgcag atattcgtaa ttatgcgggc aacgtctggt atcagcgcga    300
agtctttata ccgaaaggtt gggcaggcca gcgtatcgtg ctgcgtttcg atgcggtcac    360
tcattacggc aaagtgtggg tcaataatca ggaagtgatg gagcatcagg gcggctatac    420
gccatttgaa gccgatgtca cgccgtatgt tattgccggg aaaagtgtac gtaagtttct    480
gcttctacct tgatatata tataataatt atcattaatt agtagtaata taatatttca    540
aatatttttt tcaaaataaa agaatgtagt atatagcaat tgcttttctg tagtttataa    600
gtgtgtatat tttaatttat aacttttcta atatatgacc aaaatttgtt gatgtgcagg    660
tatcaccgtt tgtgtgaaca acgaactgaa ctggcagact atcccgccgg gaatggtgat    720
taccgacgaa aacggcaaga aaagcagtc ttacttccat gatttcttta actatgccgg    780
aatccatcgc agcgtaatgc tctacaccac gccgaacacc tgggtggacg atatcaccgt    840
ggtgacgcat gtcgcgcaag actgtaacca cgcgtctgtt gactggcagg tggtggccaa    900
tggtgatgtc agcgttgaac tgcgtgatgc ggatcaacag gtggttgcaa ctggacaagg    960
cactagcggg actttgcaag tggtgaatcc gcacctctgg caaccgggtg aaggttatct    1020
ctatgaactg tgcgtcacag ccaaaagcca gacagagtgt gatatctacc cgcttcgcgt    1080
cggcatccgg tcagtggcag tgaagggcga acagttcctg attaaccaca accgttcta    1140
ctttactggc tttggtcgtc atgaagatgc ggacttacgt ggcaaaggat cgataacgt    1200
gctgatggtg cacgaccacg cattaatgga ctggattggg ccaactcct accgtacctc    1260
gcattaccct tacgctgaag atgctcga ctgggcagat gaacatggca tcgtggtgat    1320
tgatgaaact gctgctgtcg gctttaacct ctctttaggc attggtttcg aagcgggcaa    1380
caagccgaaa gaactgtaca gcgaagaggc agtcaacggg gaaactcagc aagcgcactt    1440
acaggcgatt aaagagctga tagcgcgtga caaaaaccac ccaagcgtgg tgatgtggag    1500

```
tattgccaac gaaccggata cccgtccgca agtgcacggg aatatttcgc cactggcgga    1560
agcaacgcgt aaactcgacc cgacgcgtcc gatcacctgc gtcaatgtaa tgttctgcga    1620
cgctcacacc gataccatca gcgatctctt tgatgtgctg tgcctgaacc gttattacgg    1680
atggtatgtc caaagcggcg atttggaaac ggcagagaag gtactggaaa agaacttct    1740 ggcctggcag gagaaactgc atcagccgat tatcatcacc gaatacggcg tggatacgtt    1800
agccgggctg cactcaatgt acaccgacat gtggagtgaa gagtatcagt gtgcatggct    1860
ggatatgtat caccgcgtct tgatcgcgt cagcgccgtc gtcggtgaac aggtatggaa    1920
tttcgccgat tttgcgacct cgcaaggcat attgcgcgtt ggcggtaaca agaaagggat    1980
cttcactcgc gaccgcaaac cgaagtcggc ggcttttctg ctgcaaaaac gctggactgg    2040
catgaacttc ggtgaaaaac cgcagcaggg aggcaaacaa tgaatcaaca actctcctgg    2100
cgcaccatcg tcggctacag cctcgggaat tgctaccgag ctcggtaccc ggcgcaaaaa    2160
tcaccagtct ctctctacaa atctatctct ctctattttt ctccagaata atgtgtgagt    2220
agttcccaga taagggaatt agggttctta tagggtttcg ctcatgtgtt gagcatataa    2280 gaaacccta gtatgtattt gtatttgtaa aatacttcta tcaataaaat ttctaattcc    2340
taaaaccaaa atccagtgac cgggtaccga gctcgaattt cgacctgcag gcatgcaagc    2400
ttggcgtaat catggtcata gctgtttcct actagatctg attgtcgttt cccgccttca    2460
gtttaaacta tcagtgtttg acaggatata ttggcgggta aacctaagag aaaagagcgt    2520
ttattagaat aatcggatat ttaaaagggc gtgaaaaggt ttatccgttc gtccatttgt    2580
atgtccatga taagtcgcgc tgtatgtgtt tgtttgaata ttcatggaac gcagtggcgg    2640
ttttcatggc ttgttatgac tgtttttttg gggtacagtc tatgcctcgg gcatccaagc    2700
agcaagcgcg ttacgccgtg ggtcgatgtt tgatgttatg gagcagcaac gatgttacgc    2760
agcagggcag tcgccctaaa acaaagttaa acatcatggg ggaagcggtg atcgccgaag    2820
tatcgactca actatcagag gtagttggcg tcatcgagcg ccatctcgaa ccgacgttgc    2880
tggccgtaca tttgtacggc tccgcagtgg atggcggcct gaagccacac agtgatattg    2940
atttgctggt tacggtgacc gtaaggcttg atgaaacaac gcggcgagct tgatcaacg    3000 acctttgga aacttcggct tcccctggag agagcgagat tctccgcgct gtagaagtca    3060
ccattgttgt gcacgacgac atcattccgt ggcgttatcc agctaagcgc gaactgcaat    3120
ttggagaatg gcagcgcaat gacattcttg caggtatctt cgagccagcc acgatcgaca    3180
ttgatctggc tatcttgctg acaaaagcaa gagaacatag cgttgccttg gtaggtccag    3240
cggcggagga actctttgat ccggttcctg aacaggatct atttgaggcg ctaaatgaaa    3300
ccttaacgct atggaactcg ccgcccgact gggctggcga tgagcgaaat gtagtgctta    3360
cgttgtcccg catttggtac agcgcagtaa ccggcaaaat cgcgccgaag gatgtcgctg    3420
ccgactgggc aatggagcgc ctgccggccc agtatcagcc cgtcatactt gaagctagac    3480
aggcttatct tggacaagaa gaagatcgct tggcctcgcg cgcagatcag ttggaagaat    3540
ttgtccacta cgtgaaaggc gagatcacca aggtagtcgg caaataatgt ctagctagaa    3600
attcgttcaa gccgacgccg cttcgcggcg cggcttaact caagcgttag atgcactaag    3660
cacataattg ctcacagcca aactatcagg tcaagtctgc ttttattatt tttaagcgtg    3720
cataataagc cctacacaaa ttgggagata tatcatgcat gaccaaaatc ccttaacgtg    3780
agttttcgtt ccactgagcg tcagacccg tagaaaagat caaaggatct tcttgagatc    3840
```

```
cttttttttct gcgcgtaatc tgctgcttgc aaacaaaaaa accaccgcta ccagcgtgg    3900 tttgtttgcc ggatcaagag ctaccaactc ttttttccgaa ggtaactggc ttcagcagag   3960
cgcagatacc aaatactgtc cttctagtgt agccgtagtt aggccaccac ttcaagaact    4020
ctgtagcacc gcctacatac ctcgctctgc taatcctgtt accagtggct gctgccagtg    4080
gcgataagtc gtgtcttacc gggttggact caagacgata gttaccggat aaggcgcagc    4140
ggtcgggctg aacgggggt tcgtgcacac agcccagctt ggagcgaacg acctacaccg     4200
aactgagata cctacagcgt gagctatgag aaagcgccac gcttcccgaa gggagaaagg    4260
cggacaggta tccggtaagc ggcagggtcg aacaggaga gcgcacgagg gagcttccag     4320
ggggaaacgc ctggtatctt tatagtcctg tcgggtttcg ccacctctga cttgagcgtc    4380 gattttgtg atgctcgtca gggggcgga gccatggaa aaacgccagc aacgcggcct       4440
ttttacggtt cctggccttt tgctggcctt ttgctcacat gttctttcct gcgttatccc    4500
ctgattctgt ggataaccgt attaccgcct ttgagtgagc tgataccgct cgccgcagcc    4560
gaacgaccga gcgcagcgag tcagtgagcg aggaagcgga agagcgcctg atgcggtatt    4620
ttctccttac gcatctgtgc ggtatttcac accgcatagg ccgcgatagg ccgacgcgaa    4680 gcggcgggc gtagggagcg cagcgaccga agggtaggcg cttttttgcag ctcttcggct    4740 gtgcgctggc cagacagtta tgcacaggcc aggcgggttt taagagtttt aataagtttt    4800
aaagagtttt aggcggaaaa atcgccttt ttctcttta tatcagtcac ttacatgtgt      4860
gaccggttcc caatgtacgg ctttgggttc ccaatgtacg ggttccggtt cccaatgtac    4920
ggctttgggt tcccaatgta cgtgctatcc acaggaaaga ccctttttcg accttttttcc   4980 cctgctaggg caattttgccc tagcatctgc tccgtacatt aggaaccggc ggatgcttcg    5040
ccctcgatca ggttgcggta gcgcatgact aggatcgggc cagcctgccc cgcctcctcc    5100
ttcaaatcgt actccggcag gtcatttgac ccgatcagct tgcgcacggt gaaacagaac    5160
ttcttgaact ctccggcgct gccactgcgt tcgtagatcg tcttgaacaa ccatctggct    5220
tctgccttgc ctgcggcgcg gcgtgccagg cggtagagaa aacggccgat gccgggatcg    5280
atcaaaaagt aatcggggtg aaccgtcagc acgtccgggt tcttgccttc tgtgatctcg    5340
cggtacatcc aatcagctag ctcgatctcg atgtactccg gccgcccggt ttcgctcttt    5400
acgatcttgt agcggctaat caaggcttca ccctcggata ccgtcaccag gcggccgttc    5460 ttggcctttct tcgtacgctg catggcaacg tgcgtggtgt ttaaccgaat gcaggttttct  5520 accaggtcgt ctttctgctt tccgccatcg gctcgccggc agaacttgag tacgtccgca    5580
acgtgtggac ggaacacgcg gccgggcttg tctcccttcc cttcccggta tcggttcatg    5640
gattcggtta gatgggaaac cgccatcagt accaggtcgt aatcccacac actggccatg    5700
ccggccggcc ctgcggaaac ctctacgtgc ccgtctggaa gctcgtagcg gatcacctcg    5760
ccagctcgtc ggtcacgctt cgacagacg aaaacggcca cgtccatgat gctgcgacta    5820
tcgcgggtgc ccacgtcata gagcatcgga acgaaaaaat ctggttgctc gtcgcccttg    5880
ggcggcttcc taatcgacgg cgcaccggct gccggcggtt gccgggattc tttgcggatt    5940
cgatcagcgg ccccttgcca cgattcaccg gggcgtgctt ctgcctcgat gcgttgccgc    6000
tgggcggcct gcgcggcctt caacttctcc accaggtcat cacccagcgc cgcgccgatt    6060
tgtaccgggc cggatggttt gcgaccgctc acgccgattc ctcgggcttg ggggttccag    6120
tgccattgca gggccggcag acaacccagc cgcttacgcc tggccaaccg cccgttcctc    6180
cacacatggg gcattccacg gcgtcggtgc ctggttgttc ttgattttcc atgccgcctc    6240
```

```
ctttagccgc taaaattcat ctactcattt attcatttgc tcatttactc tggtagctgc   6300
gcgatgtatt cagatagcag ctcggtaatg gtcttgcctt ggcgtaccgc gtacatcttc   6360
agcttggtgt gatcctccgc cggcaactga aagttgaccc gcttcatggc tggcgtgtct   6420
gccaggctgg ccaacgttgc agccttgctg ctgcgtgcgc tcggacggcc ggcacttagc   6480
gtgtttgtgt ttttgctcat tttctcttta cctcattaac tcaaatgagt tttgatttaa   6540
tttcagcggc cagcgcctgg acctcgcggg cagcgtcgcc ctcgggttct gattcaagaa   6600
cggttgtgcc ggcggcggca gtgcctgggt agctcacgcg ctgcgtgata cgggactcaa   6660
gaatgggcag ctcgtacccg ccagcgcct cggcaacctc accgccgatg cgcgtgcctt    6720
tgatcgcccg cgacacgaca aaggccgctt gtagccttcc atccgtgacc tcaatgcgct   6780
gcttaaccag ctccaccagg tcggcggtgg cccatatgtc gtaagggctt ggctgcaccg   6840
gaatcagcac gaagtcggct gccttgatcg cggacacagc caagtccgcc gcctggggcg   6900
ctccgtcgat cactacgaag tcgcgccggc cgatggcctt cacgtcgcgg tcaatcgtcg   6960
ggcggtcgat gccgacaacg gttagcggtt gatcttcccg cacggccgcc caatcgcggg   7020
cactgccctg gggatcggaa tcgactaaca gaacatcggc cccggcgagt tgcagggcgc   7080
gggctagatg ggttgcgatg gtcgtcttgc ctgacccgcc tttctggtta agtacagcga   7140
taaccttcat gcgttcccct tgcgtatttg tttatttact catcgcatca tatacgcagc   7200
gaccgcatga cgcaagctgt tttactcaaa tacacatcac cttttagac gcgtggtgat    7260 tttgtgccga gctgccggtc ggggagctgt tggctggctg gtggcaggat atattgtggt   7320
gtaaacaaat tgacgcttag acaacttaat aacacattgc ggacgtcttt aatgtactga   7380
attaacatcc gtttgatact tgtctaaaat tggctgattt cgagtgcatc tatgcataaa   7440
aacaatctaa tgacaattat taccaagcag tgatcctgtc aaacactgat agtttaaact   7500
gaaggcggga aacgacaatc tgatcatgag cggagaatta agggagtcac gttatgaccc   7560
ccgccgatga cgcgggacaa gccgttttac gtttggaact gacagaaccg caacgttgaa   7620
ggagccactc agccgcgggt ttctggagtt taatgagcta agcacatacg tcagaaacca   7680
ttattgcgcg ttcaaaagtc gcctaaggtc actatcagct agcaaatatt tcttgtcaaa   7740
aatgctccac tgacgttcca taaattcccc tcggtatcca attagagtct catattcact   7800
ctcaatccaa ataatctgca ccggatctgg atcgtttcgc atgattgaac aagatggatt   7860
gcacgcaggt tctccggccg cttgggtgga gaggctattc ggctatgact gggcacaaca   7920
gacaatcggc tgctctgatg ccgccgtgtt ccggctgtca gcgcaggggc gcccggttct   7980
ttttgtcaag accgacctgt ccggtgccct gaatgaactg caggacgagg cagcgcggct   8040
atcgtggctg gccacgacgg gcgttccttg cgcagctgtg ctcgacgttg tcactgaagc   8100
gggaagggac tggctgctat tgggcgaagt gccggggcag gatctcctgt catctcacct   8160
tgctcctgcc gagaaagtat ccatcatggc tgatgcaatg cggcggctgc atacgcttga   8220
tccggctacc tgcccattcg accaccaagc gaaacatcgc atcgagcgag cacgtactcg   8280
gatggaagcc ggtcttgtcg atcaggatga tctggacgaa gagcatcagg gctcgcgcc    8340 agccgaactg ttcgccaggc tcaaggcgcg catgcccgac ggcgaggatc tcgtcgtgac   8400
acatggcgat gcctgcttgc cgaatatcat ggtggaaaat ggccgctttt ctggattcat   8460
cgactgtggc cggctgggtg tggcggaccg ctatcaggac atagcgttgg ctacccgtga   8520
tattgctgaa gagcttggcg gcgaatgggc tgaccgcttc ctcgtgcttt acggtatcgc   8580
```

-continued

```
cgctcccgat tcgcagcgca tcgccttcta tcgccttctt gacgagttct tctgagcggg    8640
acccaagctc tagatcttgc tgcgttcgga tattttcgtg gagttcccgc cacagacccg    8700
gatgatcccc gatcgttcaa acatttggca ataaagtttc ttaagattga atcctgttgc    8760
cggtcttgcg atgattatca tataatttct gttgaattac gttaagcatg taataattaa    8820
catgtaatgc atgacgttat ttatgagatg ggttttatg attagagtcc cgcaattata     8880
catttaatac gcgatagaaa acaaaatata gcgcgcaaac taggataaat tatcgcgcgc    8940
ggtgtcatct atgttactag atcgggcctc ctgtcaagct ctgagt                   8986
```